United States Patent
Nozawa et al.

(10) Patent No.: US 7,579,066 B2
(45) Date of Patent: Aug. 25, 2009

(54) ETHYLENICALLY UNSATURATED GROUP-CONTAINING ISOCYANATE COMPOUND AND PROCESS FOR PRODUCING THE SAME, AND REACTIVE MONOMER, REACTIVE (METH) ACRYLATE POLYMER AND ITS USE

(75) Inventors: Kaneo Nozawa, Kawanuma-gun (JP); Katsutoshi Morinaka, Kawanuma-gun (JP); Toru Sasaki, Kawanuma-gun (JP); Katsumi Murofushi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 280 days.

(21) Appl. No.: 11/666,905

(22) PCT Filed: Oct. 31, 2005

(86) PCT No.: PCT/JP2005/020325
§ 371 (c)(1),
(2), (4) Date: May 3, 2007

(87) PCT Pub. No.: WO2006/049264
PCT Pub. Date: May 11, 2006

(65) Prior Publication Data
US 2008/0132597 A1  Jun. 5, 2008

Related U.S. Application Data

(60) Provisional application No. 60/626,497, filed on Nov. 10, 2004, provisional application No. 60/704,431, filed on Aug. 2, 2005, provisional application No. 60/704,892, filed on Aug. 3, 2005.

(30) Foreign Application Priority Data

Nov. 4, 2004 (JP) .............................. 2004-320710
Jul. 28, 2005 (JP) .............................. 2005-219247
Jul. 28, 2005 (JP) .............................. 2005-219249

(51) Int. Cl.
C07C 263/10 (2006.01)
C07C 265/04 (2006.01)
C08F 299/00 (2006.01)

(52) U.S. Cl. .............................. 428/209; 430/7; 522/74; 522/90; 522/96; 522/173; 522/121; 522/141; 522/142; 526/297; 526/301; 526/302; 526/312; 528/65; 528/66; 560/213; 560/330; 560/336; 560/338; 560/340

(58) Field of Classification Search .................. 560/213, 560/330, 336, 338, 340; 522/74, 83, 120, 522/121, 174, 90, 96, 141, 142; 526/297, 526/301, 302, 312; 528/65, 66; 430/7; 428/209
See application file for complete search history.

(56) References Cited

U.S. PATENT DOCUMENTS 2,718,516 A   9/1955   Bortnick (Continued)

FOREIGN PATENT DOCUMENTS

EP   0 184 349 A   6/1986

(Continued)

*Primary Examiner*—Susan W Berman
(74) *Attorney, Agent, or Firm*—Sughrue Mion, PLLC

(57) ABSTRACT

There are provided a novel ethylenically unsaturated group-containing isocyanate compound, a process for producing the same, and a reactive monomer produced from the isocyanate compound, a reactive polymer and its use. The ethylenically unsaturated group-containing isocyanate compound according to the present invention is represented by formula (I).

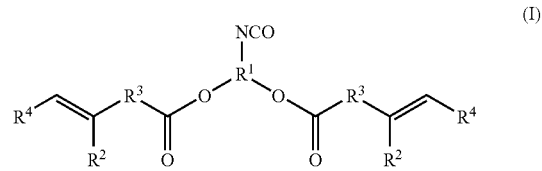

60 Claims, 1 Drawing Sheet

U.S. PATENT DOCUMENTS

| | | | |
|---|---|---|---|
| 2,821,544 A | | 1/1958 | Holtschmidt |
| 4,088,674 A | * | 5/1978 | Emmons et al. ............. 560/154 |
| 6,620,857 B2 | * | 9/2003 | Valet ........................... 522/42 |

FOREIGN PATENT DOCUMENTS

| | | |
|---|---|---|
| EP | 0 240 094 A2 | 10/1987 |
| GB | 1 252 099 | 11/1971 |
| JP | 62-195354 A | 8/1987 |
| JP | 63-010750 A | 1/1988 |
| JP | 63-010771 A | 1/1988 |
| JP | 63-010772 A | 1/1988 |
| JP | 63-010773 A | 1/1988 |
| JP | 63-010774 A | 1/1988 |
| JP | 64-014221 A | 1/1989 |
| JP | 02-129163 A | 5/1990 |
| JP | 09-143220 A | 6/1997 |
| JP | 09-296152 A | 11/1997 |
| JP | 10-104401 A | 4/1998 |
| JP | 10-287718 A | 10/1998 |
| JP | 10-300923 A | 11/1998 |
| JP | 11-228688 A | 8/1999 |
| JP | 2001-048856 A | 2/2001 |
| JP | 2001-200007 A | 7/2001 |
| JP | 2002-229201 A | 8/2002 |
| JP | 2003-226806 A | 8/2003 |
| JP | 2004-043671 A | 2/2004 |
| JP | 2004-333902 A | 11/2004 |
| JP | 2005-104842 A | 4/2005 |

* cited by examiner

ETHYLENICALLY UNSATURATED GROUP-CONTAINING ISOCYANATE COMPOUND AND PROCESS FOR PRODUCING THE SAME, AND REACTIVE MONOMER, REACTIVE (METH) ACRYLATE POLYMER AND ITS USE

CROSS REFERENCES OF RELATED APPLICATION

This application is an application filed under 35 U.S.C. §111(a) claiming benefit pursuant to 35 U.S.C. §119(e)(1) of the filing date of Provision Application 60/626,497 filed on Nov. 10, 2004, 60/704,431 filed on Aug. 2, 2005, and 60/704,892 filed on Aug. 3, 2005 pursuant to 35 U.S.C. §111(b).

TECHNICAL FIELD

The present invention relates to a novel isocyanate compound containing two or more polymerizable functional groups usable, for example, in coating materials, UV- and heat-curable coating materials, molding materials, adhesives, inks, resists, optical materials, stereolithographic materials, printing plate materials, dental materials, and polymer battery materials, and a process for producing the same. Further, the present invention relates to a reactive monomer, which is produced from this isocyanate compound, and is particularly suitable in optical materials, a curable composition comprising the same, and a cured product thereof.

The present invention relates to a reactive polymer, which can provide a curable composition with improved sensitivity and developing properties in the field of a photosensitive composition for color filters used in the production of optical color filters used, for example, in color televisions, liquid crystal display elements, solid state imaging devices, and cameras, and can provide a curable composition with improved flexibility, heat resistance, chemical resistance, plating resistance and the like in the field of a photosensitive composition for solder resists used, for example, in insulating protective films in printed wiring boards, and a process for producing the same and use of said reactive polymer. More particularly, the present invention relates to a reactive polymer, which is obtained by reacting an isocyanate compound with a polyhydroxy compound comprising repeating units and can provide, for example, a curable composition excellent in curing speed and sensitivity in curing upon exposure to ultraviolet light or heat, or a curable composition having high adhesion, high heat resistance temperature, good chemical resistance and the like, a process for producing the same and use of said reactive polymer.

BACKGROUND OF THE INVENTION

Resins which have been rendered reactive have been used in various fields. Ethylenically unsaturated group-containing isocyanate compounds are useful for the production of such resins. For example, an ethylenically unsaturated group or isocyanate group can be introduced into the resin through a reaction with a functional group in the main chain of the resin.

On the other hand, functions such as high curing speed and high crosslinking density in cured products obtained therefrom are required of resins and resin compositions. To impart such functions, ethylenically unsaturated group-containing isocyanate compounds capable of introducing a plurality of ethylenically unsaturated groups into resin molecules and a process for producing the same have been desired. Further, for applications and fields where such compounds are used, typified by optical materials, polyelectrolytes and the like, such compounds should have high purity.

Regarding the production of such ethylenically unsaturated group-containing isocyanate compounds, for example, patent document 1 discloses the following two production processes. The first process comprises reacting an amino alcohol with ethyl chlorocarbonate to give ethyl hydroxycarbamate, then reacting this compound with an unsaturated carboxylic acid chloride to give an urethanoester, and then thermally decomposing the urethanoester in the presence of phosphorus pentachloride or the like to give an unsaturated carboxylic acid isocyanatoalkyl ester.

The second process comprises preparing a chloroalkyl ester by transesterification from a methyl ester of an unsaturated carboxylic acid and chloroalcohol, then reacting this compound with an alkali metal isocyanate and ethanol to give an urethanoester of an unsaturated carboxylic acid, and then thermally decomposing this compound in the presence of phosphorus pentachloride or the like to give an isocyanatoalkyl ester of an unsaturated carboxylic acid.

These processes, however, suffer from a problem that phosphorus and sulfur are present as impurities. Further, the resultant product contains a large amount of by-products which appear to derive from the unsaturated group (for example, HCl adduct of unsaturated group). Therefore, these processes involve problems such as very low reaction yield and the necessity of a large amount of labor for purification.

Patent document 2 discloses a process which comprises reacting an unsaturated carboxylic acid chloride with an amino alcohol hydrochloride to synthesize an aminoalkyl ester hydrochloride of an unsaturated carboxylic acid and then reacting this compound with carbonyl chloride to give an isocyanatoalkyl ester of an unsaturated carboxylic acid.

Patent document 3 discloses a process which comprises reacting an imidazole derivative with carbonyl chloride, reacting the resultant compound with a monoalkanolamine, and then esterifying the resultant compound using an unsaturated carboxylic acid or its chloride or ester to give an isocyanatoalkyl ester of an unsaturated carboxylic acid.

Also in these processes disclosed in patent documents 2 and 3, however, the resultant compounds contain a large amount of by-products which appear to derive from the unsaturated group (for example, HCl adduct of the unsaturated group), posing problems such as low reaction yield and the necessity of a large amount of labor for purification.

Patent document 4 and patent document 5 disclose a process in which a 2-alkenyl-2-oxazoline is reacted with phosgene to give an isocyanatoalkyl ester of an unsaturated carboxylic acid. This process is very advantageous from the viewpoints of energy saving and safety and has been carried out on a commercial scale. Furthermore, patent document 6 to patent document 9 propose production processes of 2-alkenyl-2-oxazolines as a precursor compound.

In these processes, however, expensive oxazoline compounds are used as a starting compound, and, in addition, the process is long. Therefore, these processes are cost-ineffective. Further, since a large amount of HCl adducts of the unsaturated group are contained as by-products, disadvantageously, for example, a large amount of labor is required for purification.

Further, patent document 10 discloses a process which comprises reacting dimethyl carbonate, diethyl carbonate, or dipropyl carbonate with ethanolamine to synthesize hydroxy urethane, reacting this compound with an unsaturated carboxylic acid or its chloride or ester to give a urethanoester, and thermally decomposing this compound to give an isocyanatoalkyl ester of an unsaturated carboxylic acid.

In this process, the thermal decomposition of the urethanoester is difficult, and the percentage decomposition is 50% to 60%, for example, even at a high temperature of 400° C. The unsaturated carboxylic acid isocyanatoalkyl ester contains an ethylenically unsaturated group and thus is polymerized at this high temperature, leading to problems of lowered yield and safety problems such as clogging of the thermal decomposition reactor. Therefore, the practice of this process on a commercial scale is considered difficult.

Further, conventional processes are also disadvantageous in that a large amount of by-produced chlorine compounds and the like stay in the reaction solvent. This is considered to affect, for example, the stability of the contemplated compound at the time of purification. Further, in the prior art documents, there is no description on a technique about a compound containing in its molecule two or more polymerizable functional groups, that is, two or more ethylenically unsaturated groups, and, at the same time, containing an isocyanate group.

On the other hand, monomers, oligomers or polymers containing a urethane bond with a reactive ethylenically unsaturated group-containing isocyanate compound added thereto have hitherto been used in various fields such as coating materials, UV- and heat-curable coating materials, molding materials, adhesives, inks, resists, optical materials, stereolithographic materials, printing plate materials, dental materials, polymer battery materials, and starting materials for polymers. For example, applications of optical materials include optical lenses, films, materials for optical antireflection films such as glass for CRTs, materials for cladding materials for optical fibers, or optical adhesives, for example, for optical fibers and optical lenses.

Urea bond-containing monomers, oligomers, or polymers to which a reactive ethylenically unsaturated group-containing isocyanate compound was added have also been used in the same applications.

Regarding compositions used in optical lenses, comprising a urethane bond-containing compound, patent document 12 discloses a curable composition comprising a compound produced by reacting a diol such as a cycloolefin diol with 2-methacryloyloxyethyl isocyanate.

Patent document 21 discloses a curable composition comprising urethane(meth)acrylate produced by reacting a bisphenol-type diol with a polyisocyanate and a hydroxy-containing (meth)acrylate. In the technique disclosed in this document, an aromatic ring or cycloolefin ring has been introduced to enhance the refractive index or transparency of the lens.

This, however, increases the rigidity of the polymer and, thus the adhesion to a mold base material for providing dimensional accuracy is lowered. Further, upon curing, the crystalline area is increased, leading to lowered transparency.

In patent document 13, a fluorine-containing composition comprising a compound produced by reacting a carboxyl-containing ethylenically unsaturated monomer with a copolymer of a fluoroethylenically unsaturated monomer and glycidyl acrylate is disclosed as a fluorine-containing fluoroethylenically unsaturated compound which is a low-refractive index materials used, for example, in materials for antireflection films, materials for cladding of optical fibers, and optical adhesives.

In patent document 14, a photocurable composition comprising a (meth)acrylate compound containing in its structure a urethane bond-containing fluorine-containing monofunctional(meth)acrylate and a fluorinated polyether is disclosed as a urethane bond-containing polymer or monomer. Patent document 15 discloses a specific fluorine-containing ethylenically unsaturated compound produced by reacting a fluorohydroxy compound with a monofunctional (meth)acrylate group-containing isocyanate compound.

In patent document 13, the reactivity and the adhesion to base materials are enhanced by introducing a reactive group into a polymer side chain by a glycidyl group. In patent document 14, a photocurable composition comprising a fluorine-containing urethane(meth)acrylate and a fluorine-containing polyether realizes a highly transparent, low-refractive index ultraviolet-curable composition. They, however, are monofunctional monomers and suffer from problems of curability and adhesion. Further, crystallization upon curing causes a problem of opacity.

In patent document 15, a fluorine-containing hydroxyl compound is reacted with acrylic acid and a monofunctional (meth)acrylate group-containing isocyanate compound for conversion to a polyfunctional monomer, whereby the reactivity is enhanced and, at the same time, compatibility with other monomer is improved. This technique, however, is disadvantageous, for example, in that the fluorine content is low and a further increase in fluorine content causes a lowering in curability.

In the techniques disclosed in the above patent documents, for the reason that the fluorine content affects the refractive index, transparency, adhesion, heat resistance or the like, a curing composition is produced by mixing or reacting a fluoroethylenically unsaturated monomer with other polymer, particularly a fluoropolymer. However, problems of curability and adhesion remain unsolved. Further, upon curing, a crystalline region is formed, resulting in clouding.

Furthermore, in patent document 16, a polyfunctional urethane acrylate produced by adding a diisocyanate to a bisphenol-type acrylate is disclosed as hardcoat materials for use in the protection of the surface of glass base materials for various displays or the like, or plastic base materials. Patent document 17 discloses a curable composition comprising a urethane acrylate compound produced by reacting a polyester polyol or a polycarbonate polyol with a polyisocyanate and a hydroxyl-containing (meth)acrylate.

In the techniques disclosed in patent document 16 and patent document 17, curability, adhesion and surface hardness are provided by adding a monofunctional isocyanate to a polyol.

Regarding a urethane bond-containing compound, in patent document 18, a photocurable composition comprising an ethylenically unsaturated group-containing oligomer in which bonding has been achieved through a urea bond, and a specific photopolymerization initiator is disclosed as a coating material for optical fibers, which contributes to an improvement in photocurability and heat resistance of the overcoat. In order to enhance the curability and heat resistance, however, specific photopolymerization initiator and composition are required.

In patent document 19, a thermally polymerized material produced by allowing an isocyanate-terminated prepolymer, obtained by reacting an aliphatic diisocyanate with a diol, to react with an aromatic diamine is disclosed as a transparent material suitable for optical applications. In this technique, the transparency and heat resistance are improved by producing a cured product through a reaction between an isocyante group and an amine group.

Patent document 20 discloses a thiourethane having a specific structure formed from an isocyanate group and a thiol compound.

In these prior art techniques as well, however, regarding urethane bond-, urea bond-, or thiourethane bond-containing reactive monomers, oligomers, or polymers for use in optical applications or other fields, problems of curability, adhesion to base materials, transparency, and heat resistance remain unsolved, and any satisfactory material has not been developed.

Monomers, oligomers or polymers containing a urethane bond with the reactive ethylenically unsaturated group-containing isocyanate compound added thereto have hitherto been used in various fields. As a result of detailed review of these prior art techniques, it has been found that, for the field of resist materials, the reactive polymer has the following problems in the field of photosensitive compositions for color filters used in the production of color filters for LCDs. In conventional color filters, a black matrix (K) is formed on a surface of transparent substrate such as glass or a plastic sheet. Subsequently, three or more different hues such as red (R), green (G), and blue (B) are formed successively in a color pattern such as a stripe or mosaic form. The black matrix is disposed in a lattice, stripe or mosaic form between R, G, and B color patterns and functions to suppress color mixing between colors for a contrast improvement or to prevent light leakage-derived malfunction of a thin film transistor (TFT).

Therefore, a high level of light shielding properties are required of the black matrix, and, as disclosed in patent document 22, for example, a method in which the content of light shielding pigments or dyes is increased has been studied. This method, however, suffers from a problem that the sensitivity, developability, resolution, adhesion and the like of the photosensitive composition are deteriorated. Accordingly, the productivity is lowered, and, in addition, the accuracy and reliability required of the color filter cannot be provided. That is, the development of a curable composition which can exhibit good sensitivity (curability), adhesion, developability, and resolution under thin film and high light shielding conditions has been desired.

On the other hand, the same problems are involved in the field of solder resists used in printed wiring boards. Solder resists are used to protect a wiring (circuit) pattern on a substrate against an external environment and to coat a protective layer called a cover coat or a solder mask onto a printed wiring board from the viewpoint of preventing solder from being deposited onto an unnecessary part in the step of soldering in mounting an electronic component on a surface of a printed wiring board.

As disclosed in patent document 23, a polyfuntional epoxy resin system has been mainly used. In this case, the resultant cured film has good heat resistance, but on the other hand, the flexibility is disadvantageously low. Accordingly, the application of the above solder resist is limited to a rigid plate where the flexibility is not required of the cured film, and the use of the cured film in flexible printed wiring boards (FPCs) which have become more and more used in recent years is difficult.

Under these circumstances, in recent years, a number of proposals have been proposed on flexible solder resists. For example, patent document 24 discloses a composition comprising a carboxyl-containing urethane(meth)acrylate compound. The technique disclosed in this patent document 24 can improve flexibility, but on the other hand, due to great influence of crosslinkability and adhesion of the polymer, the chemical resistance, particularly gold plating resistance, is unsatisfactory.

The above properties of the photosensitive composition are mainly derived from the polymer used, and, thus, the structure of the polymer should be improved.

[Patent document 1] U.S. Pat. No. 2,718,516
[Patent document 2] U.S. Pat. No. 2,821,544
[Patent document 3] Japanese Patent Laid-Open No. 129163/1990
[Patent document 4] U.K. Patent No. 1,252,099
[Patent document 5] Japanese Patent Laid-Open No. 010750/1988
[Patent document 6] Japanese Patent Laid-Open No. 010771/1988
[Patent document 7] Japanese Patent Laid-Open No. 010772/1988
[Patent document 8] Japanese Patent Laid-Open No. 010773/1988
[Patent document 9] Japanese Patent Laid-Open No. 010774/1988
[Patent document 10] Japanese Patent Laid-Open No. 195354/1987
[Patent Document 11] Japanese Patent Laid-Open No. 143220/1997
[Patent Document 12] Japanese Patent Laid-Open No. 104401/1998
[Patent Document 13] Japanese Patent Laid-Open No. 14221/1989
[Patent Document 14] Japanese Patent Laid-Open No. 43671/2004
[Patent Document 15] Japanese Patent Laid-Open No. 48856/2001
[Patent Document 16] Japanese Patent Laid-Open No. 296152/1997
[Patent Document 17] Japanese Patent Laid-Open No. 287718/1998
[Patent Document 18] Japanese Patent Laid-Open No. 200007/2001
[Patent Document 19] Japanese Patent Laid-Open No. 226806/2003
[Patent Document 20] Japanese Patent Laid-Open No. 104842/2005
[Patent Document 21] Japanese Patent Laid-Open No. 333902/2004
[Patent document 22] Japanese Patent Laid-Open No. 300923/1998
[Patent document 23] Japanese Patent Laid-Open No. 228688/1999
[Patent document 24] Japanese Patent Laid-Open No. 229201/2002

DISCLOSURE OF THE INVENTION

Problems to be Solved by the Invention

An object of the present invention is to provide a novel ethylenically unsaturated group-containing isocyanate compound and to provide a production process which can suppress the production of by-products and can produce the ethylenically unsaturated group-containing isocyanate compound of high purity in a safe and simple manner.

Another object of the present invention is to provide a reactive monomer, which has excellent curability, adhesion to base materials, and transparency and, at the same time, high hardness, and has a urethane bond, a thiourethane bond, or a urea bond, a curable composition using the reactive monomer, and a cured product produced from the curable composition.

An object of the present invention is to provide a curable composition, which has a satisfactorily high level of curing properties (sensitivity), can form a highly heat resistant and durable cured film while enjoying a high level of light shielding properties, or to provide a reactive polymer, which can provide a curable composition capable of forming a cured film having flexibility and possessing excellent heat resistance and chemical resistance, and a production process and use thereof.

Means for Solving the Problems

The present inventor has noticed that the isocyanate compound used in the prior art has a structure containing one (meth)acryloyl group per isocyanate group. Against this, the present inventor has made studies on the synthesis of a specific isocyanate compound having two ethylenically unsaturated groups in its molecule.

The present inventor has further made studies on the synthesis of reactive urethane compounds, reactive thiourethane compounds, or reactive urea compounds produced by reacting this isocyanate compound with an aliphatic, aromatic, or heterocyclic group containing one or more hydroxyl, mercapto, or amino groups as an active hydrogen-containing functional group. Further, the present inventor has made studies on the synthesis of reactive polymers produced by reacting this isocyanate compound with a polymer compound comprising repeating units with an active hydrogen-containing functional group bonded thereto. As a result, the present inventor has found that the above compound can be actually produced and the above objects can be attained, which has led to the completion of the present invention.

The present invention will be summarized as follows.

[1] An ethylenically unsaturated group-containing isocyanate compound represented by formula (I)

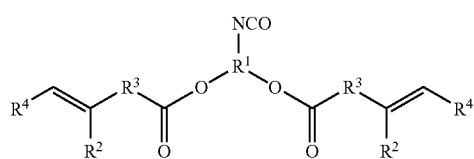

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; and $R^4$ represents a hydrogen atom, a straight-chain or branched-chain alkyl group having 1 to 6 carbon atoms, or an aryl group.

[2] The ethylenically unsaturated group-containing isocyanate compound according to the above item [1], characterized in that $R^1$ in formula (I) is a straight-chain or branched-chain saturated aliphatic group having 1 to 5 carbon atoms.

[3] The ethylenically unsaturated group-containing isocyanate compound according to the above item [1] or [2], characterized in that $R^3$ in formula (I) is a straight-chain or branched-chain alkylene group having 0 to 3 carbon atoms.

[4] The ethylenically unsaturated group-containing isocyanate compound according to any of the above items [1] to [3], characterized in that $R^4$ in formula (I) is a hydrogen atom or a methyl or aryl group.

[5] The ethylenically unsaturated group-containing isocyanate compound according to the above item [1], characterized by being represented by formula (II)

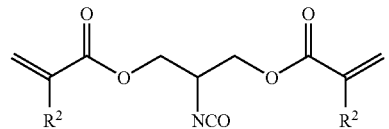

wherein $R^2$ represents a hydrogen atom or a methyl group.

[6] The ethylenically unsaturated group-containing isocyanate compound according to the above item [1], characterized by being represented by formula (III)

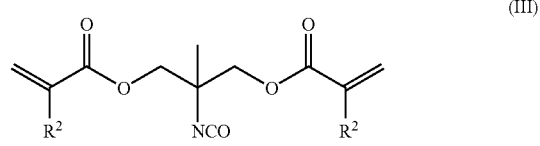

wherein $R^2$ represents a hydrogen atom or a methyl group.

[7] The ethylenically unsaturated group-containing isocyanate compound according to the above item [1], characterized by being represented by formula (IV)

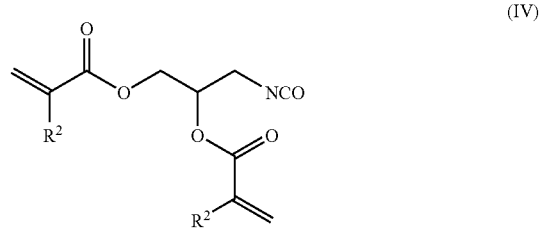

wherein $R^2$ represents a hydrogen atom or a methyl group.

[8] A process for producing an ethylenically unsaturated group-containing isocyanate compound characterized by comprising the steps of:

preparing a dihydroxyamine mineral acid salt compound represented by formula (VI)

wherein $R^1$ is as defined below, and $X^1$ represents a mineral acid, from a dihydroxyamine compound represented by formula (V)

wherein $R^1$ represents a straight-chain or branched-chain saturated aliphatic group having 1 to 10 carbon atoms, and a mineral acid;

preparing an ester compound represented by formula (VIII)

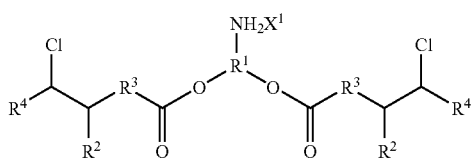
(VIII)

wherein $R^1$ and $X^1$ are as defined above and $R^2$ to $R^4$ are as defined below, from the dihydroxyamine mineral acid salt compound and a compound represented by formula (VII)

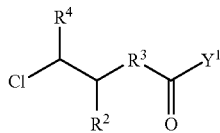
(VII)

wherein $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms;

preparing an isocyanate compound represented by formula (X)

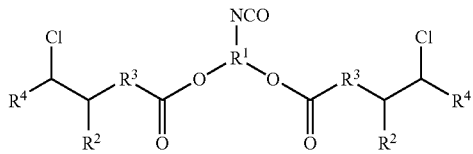
(X)

wherein $R^1$ to $R^4$ are as defined above, from the ester compound and a compound represented by general formula (IX)

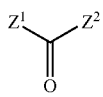
(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles; and dehydrochlorinating the isocyanate compound in the presence of a basic nitrogen compound to give an ethylenically unsaturated group-containing isocyanate compound represented by formula (I)

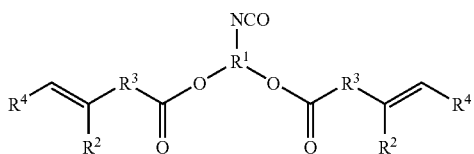
(I)

wherein $R^1$ to $R^4$ are as defined above.

[9] The process for producing the ethylenically unsaturated group-containing isocyanate compound according to the above item [8], characterized in that the mineral acid reacted with the dihydroxyamine compound represented by formula (V) is sulfuric acid, nitric acid, hydrochloric acid, carbonic acid, or phosphoric acid.

[10] The process for producing an ethylenically unsaturated group-containing isocyanate compound according to the above item [8] or [9], characterized in that the reaction in each of the steps is carried out in a solvent.

[11] The process for producing an ethylenically unsaturated group-containing isocyanate compound according to any of the above items [8] to [10], characterized in that the reaction in the step of preparing the dihydroxyamine mineral acid salt compound represented by formula (VI) from the dihydroxyamine compound represented by formula (V) and the mineral acid is carried out in a solvent selected from water, alcohols, esters, ethers, aromatic hydrocarbons, aliphatic hydrocarbons, and halogenated hydrocarbons.

[12] The process for producing an ethylenically unsaturated group-containing isocyanate compound according to any of the above items [8] to [10], characterized in that the reaction in the step of preparing the ester compound represented by formula (VIII), the reaction in the step of preparing the isocyanate compound represented by formula (X), and the reaction in the step of preparing the ethylenically unsaturated group-containing isocyanate compound represented by formula (I) are carried out in a solvent selected from esters, ethers, aromatic hydrocarbons, aliphatic hydrocarbons, and halogenated hydrocarbons.

[13] The process for producing an ethylenically unsaturated group-containing isocyanate compound according to any of the above items [8] to [12], characterized in that, after the dihydroxyamine compound represented by formula (V) is reacted with the mineral acid in the solvent to give the dihydroxyamine mineral acid salt compound represented by formula (VI), the reaction solvent is removed by evaporation and the next step of carrying out the reaction for preparing the ester compound represented by formula (VIII) is carried out.

[14] The process for producing an ethylenically unsaturated group-containing isocyanate compound according to any of the above items [8] to [12], characterized in that the reaction in the step of dehydrochlorinating the isocyanate compound represented by formula (X) in the presence of a basic nitrogen compound to give the ethyleneically unsaturated group-containing isocyanate compound represented by formula (I) is carried out at a temperature of 0° C. to 150° C.

[15] The process for producing an ethylenically unsaturated group-containing isocyanate compound according to any of the above items [8] to [14], characterized in that basic nitrogen compound used in the step of dehydrochlorinating the isocyanate compound represented by formula (X) in the presence of a basic nitrogen compound to give the ethyleneically unsaturated group-containing isocyanate compound represented by formula (I) is triethylamine.

[16] A process for producing an ethylenically unsaturated group-containing isocyanate compound characterized by comprising the steps of:

preparing a dihydroxyamine mineral acid salt compound represented by formula (VI)

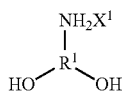
(VI)

wherein $R^1$ is as defined below, and $X^1$ represents a mineral acid, from a dihydroxyamine compound represented by formula (V)

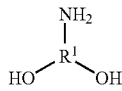
(V)

wherein $R^1$ represents a straight-chain or branched-chain saturated aliphatic group having 1 to 10 carbon atoms, and a mineral acid;

preparing an ester compound represented by formula (XII)

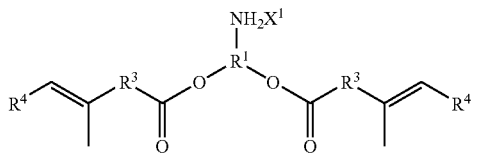
(XII)

wherein $R^1$ and $X^1$ are as defined above and $R^3$ and $R^4$ are as defined below, from the dihydroxyamine mineral acid salt compound and a compound represented by formula (XI)

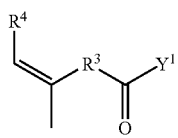
(XI)

wherein $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms; and preparing an ethylenically unsaturated group-containing isocyanate compound represented by formula (XIII)

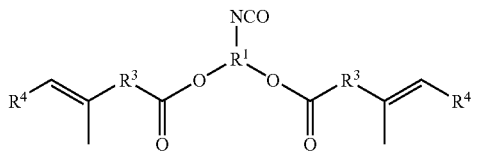
(XIII)

wherein $R^1$, $R^3$, and $R^4$ are as defined above, from the ester compound and a compound represented by general formula (IX)

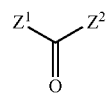
(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles.

[17] The process for producing the ethylenically unsaturated group-containing isocyanate compound according to the above item [16], characterized in that the mineral acid reacted with the dihydroxyamine compound represented by formula (V) is sulfuric acid, nitric acid, hydrochloric acid, carbonic acid, or phosphoric acid.

[18] The process for producing an ethylenically unsaturated group-containing isocyanate compound according to the above item [16] or [17], characterized in that the reaction in each of the steps is carried out in a solvent.

[19] The process for producing an ethylenically unsaturated group-containing isocyanate compound according to any of the above items [16] to [18], characterized in that the reaction in the step of preparing the dihydroxyamine mineral acid salt compound represented by formula (VI) from the dihydroxyamine compound represented by formula (V) and the mineral acid is carried out in a solvent selected from water, alcohols, esters, ethers, aromatic hydrocarbons, aliphatic hydrocarbons, and halogenated hydrocarbons.

[20] The process for producing an ethylenically unsaturated group-containing isocyanate compound according to any of the above items [16] to [19], characterized in that the reaction in the step of preparing the ester compound represented by formula (XII) and the reaction in the step of preparing the ethylenically unsaturated group-containing isocyanate compound represented by formula (XIII) are carried out in a solvent selected from esters, ethers, aromatic hydrocarbons, aliphatic hydrocarbons, and halogenated hydrocarbons.

[21] The process for producing an ethylenically unsaturated group-containing isocyanate compound according to any of the above items [16] to [20], characterized in that, after the dihydroxyamine compound represented by formula (V) is reacted with the mineral acid in the solvent to give the dihydroxyamine mineral acid salt compound represented by formula (VI), the reaction solvent is removed by evaporation and the next step of carrying out the reaction for preparing the ester compound represented by formula (XII) is carried out.

[22] A reactive monomer represented by formula (Ia)

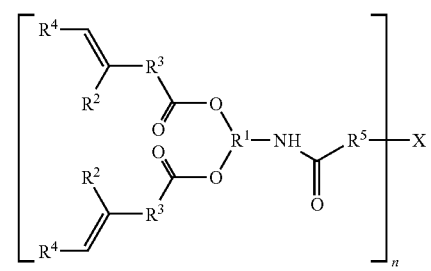
(Ia)

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; R⁴ represents a hydrogen atom, a straight-chain or branched-chain alkyl group having 1 to 6 carbon atoms, or an aryl group; R⁵ represents an ether, thioether, or NH group; X represents an aliphatic, aromatic, or heterocyclic group; and n is an integer of 1 to 4.

[23] The reactive monomer according to the above item [22], characterized by being represented by formula (IIa)

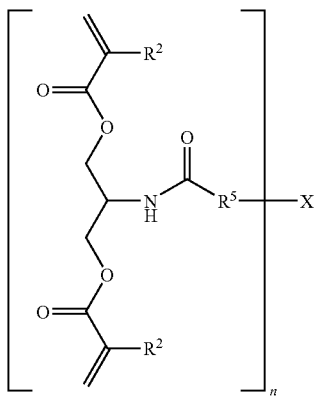

(IIa)

wherein R², R⁵, and X are as defined above.

[24] The reactive monomer according to the above item [22], characterized by being represented by formula (IIIa)

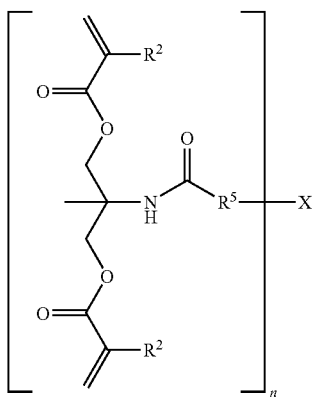

(IIIa)

wherein R², R⁵, and X are as defined above.

[25] The reactive monomer according to the above item [22], characterized by being represented by formula (IVa)

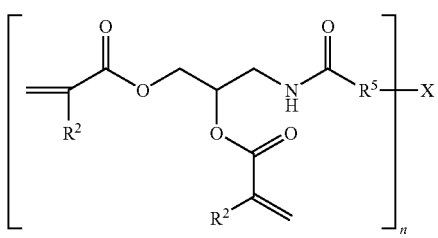

(IVa)

wherein R², R⁵, and X are as defined above.

[26] The reactive monomer according to any of the above items [22] to [25], characterized in that R⁵ in formula (Ia) is an ether group, X represents a fluorine-containing group, and n=1.

[27] The fluorine-containing reactive monomer according to the above item [26], characterized in that X in formula (Ia) is a group represented by —(CH₂)$_m$(CF₂)$_l$F wherein m is an integer of 0 to 2 and l is an integer of 0 to 8, provided that m and l are not simultaneously 0.

[28] The reactive monomer according to any of the above items [22] to [25], characterized in that R⁵ in formula (Ia) is an ether group, X represents a fluorine-containing group, and n=2.

[29] The reactive monomer according to any of the above items [22] to [25], characterized in that R⁵ in formula (Ia) is an ether group, X represents a group having a fluorene skeleton, and n=2.

[30] The reactive monomer according to the above item [29], characterized in that X in formula (Ia) is a group represented by formula (XVI)

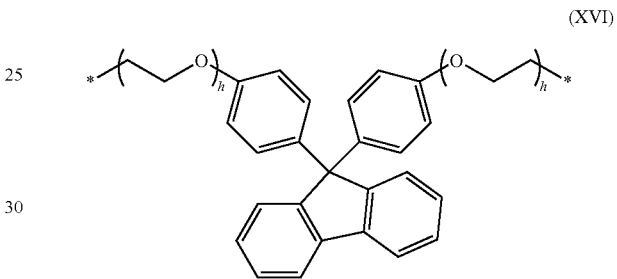

(XVI)

wherein h is an integer of 1 to 4.

[31] The reactive monomer according to any of the above items [22] to [25], characterized in that R⁵ in formula (Ia) is group NH, X represents a fluorine-containing group, and n=1.

[32] The reactive monomer according to the above item [31], characterized in that X in formula (Ia) represents a group represented by F(CF₂)₈CH₂—, or X—R⁵ represents a residue of 2,6-difluoroaniline.

[33] The reactive monomer according to any of the above items [22] to [25], characterized in that R⁵ in formula (Ia) is group NH, X represents an alkyl, xylylene, or norbornane group, and n=2.

[34] The reactive monomer according to the above item [33], characterized in that X—R⁵ in formula (Ia) represents a residue of m-xylylenediamine or a residue of 2,3,5,6-tetrafluoro-1,4-xylylenediamine, or X is represented by formula (XVII)

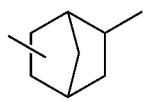

(XVII)

[35] The reactive monomer according to any of the above items [22] to [25], characterized in that R⁵ in formula (Ia) represents a thioether group, X represents a straight-chain or branched-chain saturated aliphatic group, or a phenyl group.

[36] A process for producing a reactive (meth)acrylate polymer, characterized in that an ethylenically unsaturated group-containing isocyanate compound represented by formula (I)

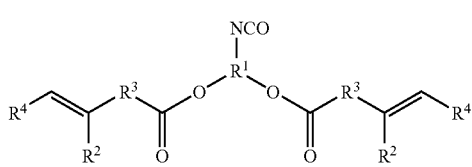

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; and $R^4$ represents a hydrogen atom, a straight-chain or branched-chain alkyl group having 1 to 6 carbon atoms, or an aryl group, is reacted with a polymer compound comprising repeating units to which an active hydrogen-containing functional group is attached.

[37] The process for producing a reactive (meth)acrylate polymer according to the above item [36], characterized in that said polymer compound is a polyhydroxy compound comprising repeating units.

[38] The process for producing a reactive (meth)acrylate polymer according to the above item [36] or [37], characterized in that said ethylenically unsaturated group-containing isocyanate compound is represented by formula (II)

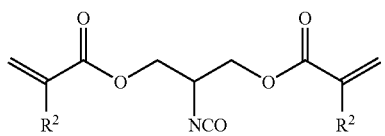

wherein $R^2$ represents a hydrogen atom or a methyl group.

[39] The process for producing a reactive (meth)acrylate polymer according to the above item [36] or [37], characterized in that said ethylenically unsaturated group-containing isocyanate compound is represented by formula (III)

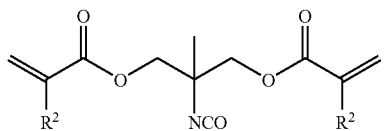

wherein $R^2$ represents a hydrogen atom or a methyl group.

[40] The process for producing a reactive (meth)acrylate polymer according to any of the above items [37] to [39], characterized in that said repeating unit-containing polyhydroxy compound is a polyester polyol compound, a polycarbonate polyol compound, a polyether polyol compound, a polyurethane polyol compound, a homo- or copolymer of hydroxyalkyl(meth)acrylate, or an epoxy(meth)acrylate compound.

[41] The process for producing a reactive (meth)acrylate polymer according to any of the above items [37] to [40], characterized in that said repeating unit-containing polyhydroxy compound contains a carboxyl group.

[42] A reactive (meth)acrylate polymer produced in that an ethylenically unsaturated group-containing isocyanate compound represented by formula (I)

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms, or an aryl group, is reacted with a polymer compound comprising repeating units to which an active hydrogen-containing functional group is attached.

[43] The reactive (meth)acrylate polymer according to the above item [42], characterized in that said polymer compound is a repeating unit-containing polyhydroxy compound.

[44] The reactive (meth)acrylate polymer according to the above item [42] or [43], characterized in that said ethylenically unsaturated group-containing isocyanate compound is represented by formula (II)

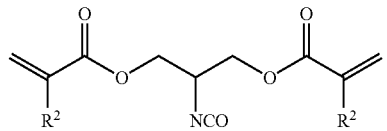

[45] The reactive (meth)acrylate polymer according to the above item [42] or [43], characterized in that said ethylenically unsaturated group-containing isocyanate compound is represented by formula (III)

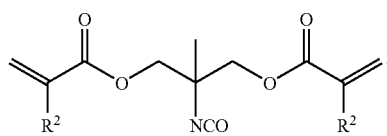

[46] The reactive (meth)acrylate polymer according to any of the above items [43] to [45], characterized in that said repeating unit-containing polyhydroxy compound is a polyester polyol compound, a polycarbonate polyol compound, a polyether polyol compound, a polyurethane polyol compound, a homo- or copolymer of a hydroxyalkyl(meth)acrylate, or an epoxy(meth)acrylate compound.

[47] The reactive (meth)acrylate polymer according to any of the above items [43] to [46], characterized in that said repeating unit-containing polyhydroxy compound contains a carboxyl group.

[48] A curable composition characterized by comprising the reactive monomer according to any of the above items [22] to [35] and a polymerization initiator.

[49] A cured product produced by curing the curable composition according to the above item [48].

[50] A curable composition characterized by comprising a reactive (meth)acrylate polymer (A) according to any of the above items [43] to [47] and a pigment (B).

[51] The curable composition according to the above item [50], characterized by further comprising a photopolymerization initiator (D).

[52] The curable composition according to the above item [51], characterized by further comprising an ethylenically unsaturated monomer (F).

[53] The curable composition according to the above item [52], characterized by comprising 10 to 40% by mass of the reactive (meth)acrylate polymer (A), 25 to 60% by mass of the pigment (B), 2 to 25% by mass of the photopolymerization initiator (D), 5 to 20% by mass of the ethylenically unsaturated monomer (F), and an organic solvent (G).

[54] The curable composition according to the above item [52], characterized by comprising 10 to 40% by mass of the reactive (meth)acrylate polymer (A), 25 to 60% by mass of the pigment (B), 2 to 20% by mass of the photopolymerization initiator (D), 5 to 20% by mass of the ethylenically unsaturated monomer (F), the organic solvent (G), and 2 to 20% by mass of a polyfunctional thiol (H).

[55] The curable composition according to any of the above items [52] to [54], characterized in that said curable composition is used for color filter formation.

[56] The curable composition according to the above item [55], characterized in that the pigment (B) is carbon black.

[57] A curable composition characterized by comprising the reactive (meth)acrylate polymer (A) according to any of the above items [43] to [47], a heat-curable polymer (C), a photopolymerization initiator (D), and a thermal polymerization catalyst (E).

[58] The curable composition according to the above item [57], characterized in that said curable composition is used as a solder resist.

[59] An insulating protective film having been formed using the curable composition according to the above item [58].

[60] A printed wiring board comprising the insulating protective film according to the above item [59].

The isocyanate compound represented by formula (I) containing in its molecule two or more polymerizable functional groups, that is, containing two or more ethylenically unsaturated bonds, is suitable as starting reactive monomers for resins used, for example, in a wide variety of fields such as coating materials, UV- and heat-curable coating materials, molding materials, adhesives, inks, resists, optical materials, stereolithographic materials, printing plate materials, dental materials, and polymer battery materials.

Further, in various fields, the isocyanate compound represented by formula (I) can be used in the production of resins with a reactive functional group, that is, an ethylenically unsaturated group or an isocynate group, introduced thereinto. For example, isocyanate group-containing functional polymer materials can be produced by copolymerizing the isocyanate compound represented by formula (I), for example, with (meth)acrylates such as methyl methacrylate or methylacrylate, or vinyl group-containing compounds such as vinyl ether and styrene. Further, reacting, e.g., monomers, oligomers, or polymers containing active hydrogen such as hydroxyl, amino or carboxyl groups, with an isocyanate group can realize the introduction of a polymerizable unsaturated group into the monomers, oligomers, polymers or the like to produce materials which are curable upon exposure to ultraviolet light, electron beams, heat or the like.

Further, the isocyanate compound represented by formula (I) can provide a curable composition which can realize a high curing speed. Furthermore, a curable composition which can provide a cured product having high crosslinking density can be provided.

On the other hand, the use of the reactive monomer represented by formula (Ia) is advantageous in that, since there are two adjacent reactive ethylenically unsaturated groups, the radical reactivity between the ethylenically unsaturated groups is high, and, at the same time, the adhesive strength to the base material is excellent. This increase in adhesive strength is considered attributable to a high level of reactivity and a high level of crosslinkability.

Since the ethylenically unsaturated groups are adjacent to each other, upon exposure to light or heat, curing proceeds in an amorphous manner and the proportion of the crystalline region is reduced. As a result, good transparency can be realized.

Further, because of polyfunctionality, the compound functions as a crosslinking component to provide a heat-curable or photocurable curing composition. This curable composition can be cured at a high curing speed. Further, this curing composition can provide a cured product having high crosslinking density.

The two reactive ethylenically unsaturated groups can be copolymerized, for example, with (meth)acrylates such as methyl methacrylate and methyl acrylate, or ethylenically unsaturated group-containing compounds such as vinyl ether and styrene and can also be used as monomers for polymer production.

The reactive monomer represented by formula (Ia) is suitable for use in a wide variety of fields such as coating materials, UV- and heat-curable coating materials, molding materials, adhesives, inks, resists, optical materials, stereolithographic materials, printing plate materials, dental materials, and polymer battery materials. In particular, by virtue of features such as curing reactivity, adhesion to base materials, and transparency, the reactive monomer represented by formula (Ia) is suitable for use, for example, in optical materials, coating materials, resists, and UV curing coating materials.

Effect of the Invention

The present invention provides a novel isocyanate compound containing in its molecule two or more polymerizable functional groups, that is, two or more ethylenically unsaturated groups.

In the production of the ethylenically unsaturated group-containing isocyanate compound, the production process of the present invention can suppress the production of by-products and, at the same time, can produce a high-purity ethylenically unsaturated group-containing isocyanate compound in a safe and simple manner.

The present invention can provide a reactive monomer containing a urethane bond, a thiourethane bond, or a urea bond, which is excellent in curability, adhesion to base materials, and transparency, and, at the same time, has high hardness, a curable composition using the reactive monomer, and a cured product produced from the curable composition.

The production process of the present invention using an ethylenically unsaturated group-containing isocyanate can provide a curable composition, which has a satisfactorily high level of curing properties (sensitivity), can form a highly heat resistant and durable cured film while enjoying a high level of light shielding properties, or can provide a reactive (meth)acrylate polymer which can provide a curable composition capable of forming a cured film having flexibility and possessing excellent heat resistance and chemical resistance.

The reactive (meth)acrylate polymer according to the present invention can provide a curable composition which has a satisfactorily high level of curing properties (sensitivity), can form a highly heat resistant and durable cured film while enjoying a high level of light shielding properties, or a curable composition capable of forming a cured film having flexibility and possessing excellent heat resistance and chemical resistance.

The curable composition comprising a reactive (meth) acrylate polymer according to the present invention has a satisfactorily high level of curing properties (sensitivity) and can form a cured film which has high heat resistance and durability while enjoying a high level of light shielding properties and is suitable for use in a color filter.

Further, the curable composition can form a cured film which is flexible and, at the same time, possesses excellent heat resistance and chemical resistance, and is suitable for a solder resist.

BRIEF DESCRIPTION OF THE DRAWING

FIG. 1 is an X-ray analysis chart for Example 7 and Comparative Example 8.

BEST MODE FOR CARRYING OUT THE INVENTION

Figure 1:
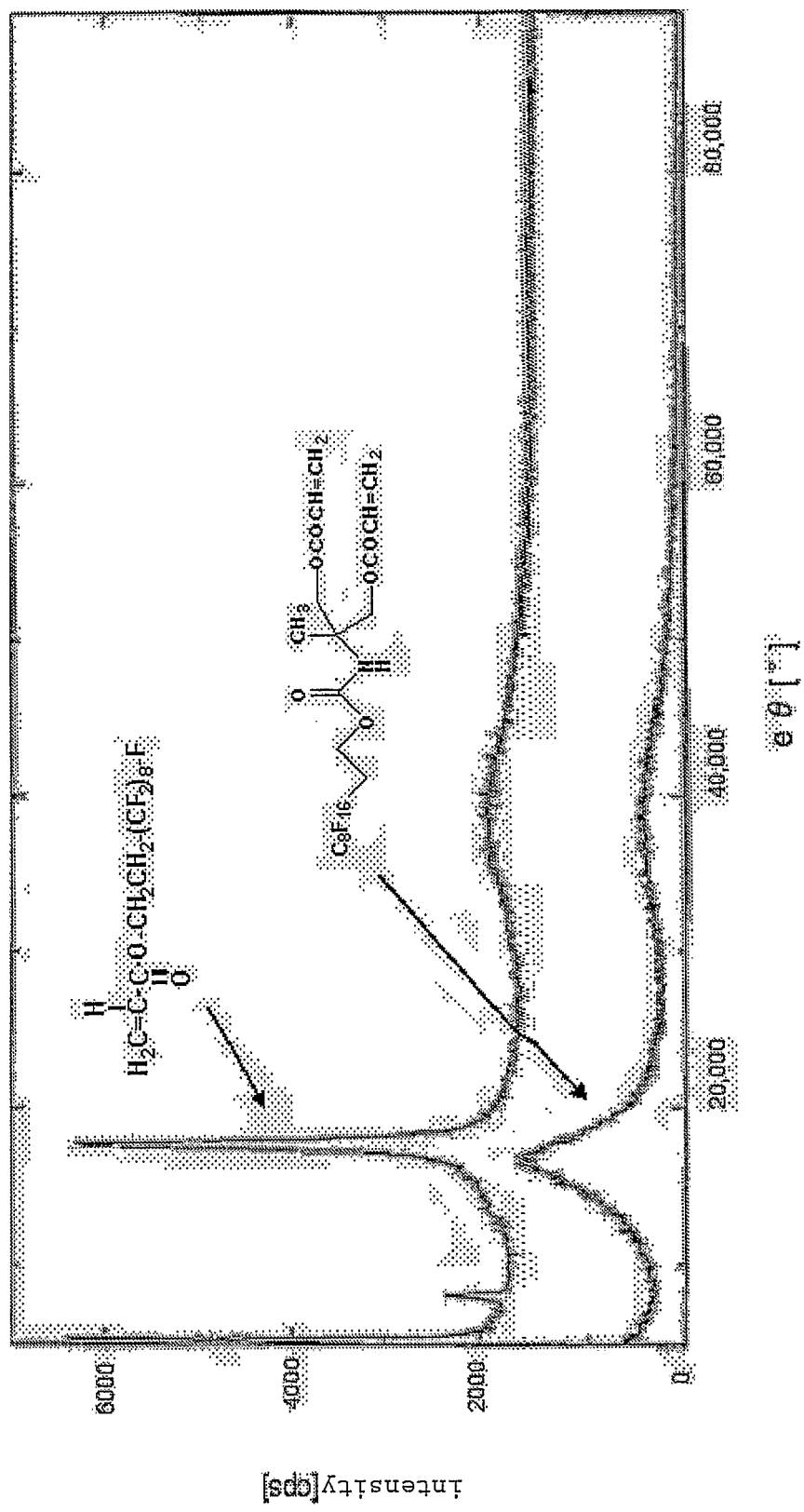
[FIG. 1]

The present invention will be described in more detail.

(i) Ethylenically Unsaturated Group-containing Isocyanate Compound

The ethylenically unsaturated group-containing isocyanate compound according to the present invention is represented by formula (I). All general formulae in the present specification embrace all stereoisomers such as cis and trans isomers.

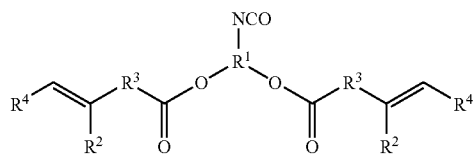

(I)

wherein $R^1$ represents a straight-chain or branched-chain saturated aliphatic group having 1 to 10 carbon atoms, preferably 1 to 5 carbon atoms, and $R^2$ represents a hydrogen atom or a methyl group. More preferably, $R^1$ represents a branched saturated aliphatic group having 3 or 4 carbon atoms from the viewpoint of easiness in synthesizing the isocyanate group. $R^3$ represents a straight-chain or branched-chain alkylene group having 0 to 5 carbon atoms, preferably 0 to 3 carbon atoms. $R^4$ represents a hydrogen atom, a straight-chain or branched-chain alkyl group having 1 to 6 carbon atoms, or an aryl group. Preferably, $R^4$ represents a hydrogen atom, a methyl group, or an aryl group.

Specific examples of preferred ethylenically unsaturated group-containing isocyanate compounds according to the present invention include compounds represented by formulae (II) to (IV).

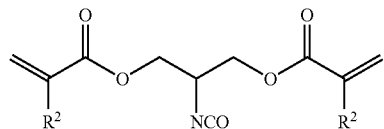

(II)

-continued

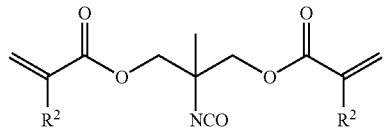

(III)

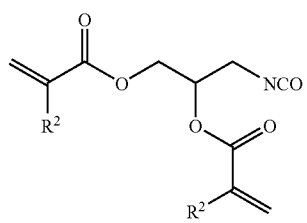

(IV)

In formulae (II) to (IV), $R^2$ represents a hydrogen atom or a methyl group.

The production process of an ethylenically unsaturated group-containing isocyanate compound according to the present invention will be described.

(ii) First Production Process of the Ethylenically Unsaturated Group-containing Isocyanate Compound The first production process of the ethylenically unsaturated group-containing isocyanate compound according to the present invention comprises the following first to fourth steps.

[First Step]

A step of preparing a dihydroxyamine mineral acid salt compound represented by formula (VI)

$$\underset{HO}{\overset{NH_2X^1}{\underset{|}{R^1}}}\overset{}{\underset{OH}{}}$$

(VI)

wherein $R^1$ is as defined below, and $X^1$ represents a mineral acid, from a dihydroxyamine compound represented by formula (V)

$$\underset{HO}{\overset{NH_2}{\underset{|}{R^1}}}\overset{}{\underset{OH}{}}$$

(V)

wherein $R^1$ represents a straight-chain or branched-chain saturated aliphatic group having 1 to 10 carbon atoms, and a mineral acid.

[Second Step]

A step of preparing an ester compound represented by formula (VIII)

$$\underset{R^4}{\overset{Cl}{\underset{|}{\phantom{x}}}}\overset{}{\underset{R^2}{\underset{|}{R^3}}}\overset{}{\underset{O}{\overset{}{\underset{||}{C}}}}\overset{}{\underset{O}{\underset{|}{R^1}}}\overset{NH_2X^1}{\underset{|}{}}\overset{}{\underset{O}{\underset{|}{}}}\overset{}{\underset{}{\underset{||}{C}}}\overset{}{\underset{R^2}{\underset{|}{R^3}}}\overset{Cl}{\underset{|}{R^4}}$$

(VIII)

wherein $R^1$ and $X^1$ are as defined above and $R^2$ to $R^4$ are as defined below, from the dihydroxyamine mineral acid salt compound and a compound represented by formula (VII)

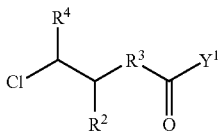

(VII)

wherein $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms.

[Third Step]

A step of preparing an isocyanate compound represented by formula (X)

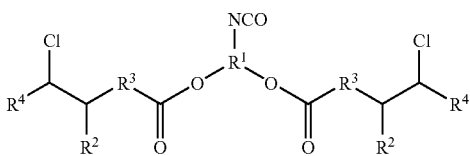

(X)

wherein $R^1$ to $R^4$ are as defined above, from the ester compound and a compound represented by general formula (IX)

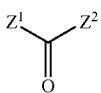

(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles.

[Fourth Step]

A step of dehydrochlorinating the isocyanate compound in the presence of a basic nitrogen compound to give an ethylenically unsaturated group-containing isocyanate compound represented by formula (I)

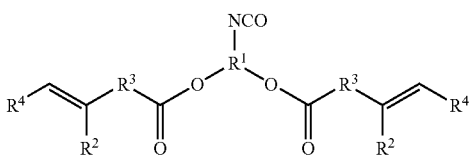

(I)

wherein $R^1$ to $R^4$ are as defined above.

(ii-a) First Step

Mineral acids usable in the first step include, for example, sulfuric acid, nitric acid, hydrochloric acid, phosphoric acid, and carbonic acid. Among them, hydrochloric acid and carbonic acid are preferred. More preferred is hydrochloric acid. The use of dry hydrogen chloride gas is particularly preferred.

Dihydroxyamine compounds represented by formula (V) used in the first step are easily commercially available. Specific examples of dihydroxyamine compounds represented by formula (V) include aminomethanediol, 2-amino-1,1-ethanediol, 1-amino-1,2-ethanediol, 1-amino-1,1-propanediol, 1-amino-1,2-propanediol, 1-amino-1,3-propanediol, 2-amino-1,2-propanediol, 2-amino-1,3-propanediol, 3-amino-1,1-propanediol, 3-amino-1,2-propanediol, 1-amino-1,4-butanediol, 1-amino-2,3-butanediol, 2-amino-1,3-butanediol, 2-amino-1,4-butanediol, 3-amino-1,2-butanediol, 4-amino-1,2-butanediol, 4-amino-1,3-butanediol, 1-amino-2-methyl-1,3-propanediol, 3-amino-2-methyl-1,2-propanediol, 2-aminomethyl-1,3-propanediol, 2-amino-2-methyl-1,3-propanediol, 2-aminomethyl-1,2-butanediol, 2-amino-1,3-pentanediol, 2-amino-1,4-pentanediol, 2-amino-1,5-pentanediol, 3-amino-1,2-pentanediol, 3-amino-1,5-pentanediol, 3-amino-2,4-pentanediol, 4-amino-1,2-pentanediol, 5-amino-1,2-pentanediol, 5-amino-1,3-pentanediol, 2-aminomethyl-2-methyl-1,3-propanediol, 2-amino-2-methyl-1,3-butanediol, 2-amino-2-ethyl-1,3-propanediol, 2-amino-2-methyl-1,4-butanediol, 2-amino-3-methyl-1,3-butanediol, 2-amino-3-methyl-1,4-butanediol, 2-[hydroxy(1-methylethyl)amino]-ethanol, 2-(2-aminoethyl)-1,3-propanediol, 3-amino-2,2-dimethyl-1,4-butanediol, 2-(aminomethyl)-2-ethyl-1,3-propanediol, 2-amino-3-ethyl-1,4-butanediol, 2-amino-2-ethyl-1,4-butanediol, 3-(aminomethyl)-1,5-pentanediol, 2-(2-amino-1-methylethyl)-1,3-propanediol, 3-amino-3-methyl-2,4-pentanediol, 2-amino-1,3-hexanediol, 2-amino-1,6-hexanediol, 2-amino-3,4-hexanediol, 3-amino-1,2-hexanediol, 4-amino-2,3-hexanediol, 6-amino-1,2-hexanediol, 6-amino-1,3-hexanediol, 6-amino-1,4-hexanediol, 1-amino-4-methyl-2,4-pentanediol, 3-amino-2-methyl-2,4-pentanediol, 4-amino-2-methyl-2,3-pentanediol, 4-amino-4-methyl-2,3-pentanediol, 2-amino-4-methyl-1,3-pentanediol, 3-amino-3-methyl-2,4-pentanediol, 3-amino-4-methyl-1,2-pentanediol, 2-amino-2-hydroxymethyl-3-methylbutanol, 5-amino-2-hydroxymethylpentanol, 2-amino-2-isopropyl-1,3-propanediol, 3-(2-aminomethyl)-1,5-pentanediol, 5-(dimethylamino)-1,2-pentanediol, 2-(dimethylamino)-1,5-pentanediol, 2-amino-3-ethyl-1,5-pentanediol, 4-amino-3,5-heptanediol, 2-amino-2-ethyl-1,5-pentanediol, 2-(3-amino-2-methylpropyl)-1,3-propanediol, 2-(4-aminobutyl)-1,3-propanediol, 2-amino-1,7-heptanediol, 3-amino-5-methyl-1,2-hexanediol, 2-aminobutyl-1,3-propanediol, 3-amino-3-ethyl-2,4-pentanediol, 1-amino-4-methyl-2,4-hexanediol, 2-amino-4,4-dimethyl-1,3-pentanediol, 2-amino-5-methyl-1,3-hexanediol, 2-amino-5-methyl-3,4-hexanediol, 4-amino-1,7-heptanediol, 2-amino-1,3-heptanediol, 5-amino-2-methyl-3,4-heptanediol, 3-amino-1,2-octanediol, 2-amino-6-methyl-3,4-heptanediol, 2-(2-amino-1-methylethyl)-1,5-pentanediol, 3-(2-aminopropyl)-1,5-pentanediol, 2-amino-2-pentyl-1,3-propanediol, 6-amino-2-methyl-1,2-heptanediol, 2-amino-1,3-octanediol, 2-amino-3,4-octanediol, 2-amino-1,8-octanediol, 4-(aminomethyl)-2,6-heptanediol, 2-amino-2-hexyl-1,3-propanediol, 5-(aminomethyl)-2-methyl-3,5-heptanediol, 1-amino-4,5,5-trimethyl-2,4-hexanediol, 2-amino-1,3-nonanediol, 2-amino-7-methyl-3,4-octanediol, 2-amino-3,4-nonanediol, 8-amino-2,5-nonanediol, 3-(2-aminopropyl)-2-methyl-1,5-pentanediol, 3-amino-1,2-decanediol, 5-(aminomethyl)-2-methyl-3,5-octanediol, 3-(aminomethyl)-2,2-dimethyl-3,5-heptanediol, 2-amino-3,7-dimethyl-1,3-octanediol, 1-amino-3,7-dimethyl-2,3- octanediol, 2-amino-1,10-decanediol, 2-amino-1,3-decanediol, 8-amino-2,3-dimethyl-2,3-octanediol, 2-amino-1,3-decanediol.

The reaction temperature in the first step may vary depending upon the type of the compound used. The reaction temperature is generally 0 to 150° C., preferably 15 to 120° C., more preferably 30 to 100° C. When the reaction temperature is excessively low, the reaction rate is likely to be lowered. On the other hand, when the reaction temperature is excessively high, the produced salt is likely to be thermally decomposed.

Whether or not the solvent is to be used in the first step depends upon the type of the compound used or the like. When the amine compound represented by formula (V) and/or the amine mineral acid salt compound represented by formula (VI) is liquid or melts, the reaction may be carried out in the absence of a solvent. On the other hand, when the amine compound represented by formula (V) and/or the amine mineral acid salt compound represented by formula (VI) is solid or does not melt, the reaction is preferably carried out in the presence of a solvent.

Specific examples of solvents usable herein include water; alcohols such as methanol, ethanol, n-propanol, isopropanol, n-butanol and n-hexanol; esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the amine compound represented by formula (V) based on the total amount of the amine compound of formula (V), the mineral acid and the solvent is generally 1 to 50% by weight, preferably 5 to 30% by weight, more preferably 10 to 20% by weight. When the amount of the solvent used is excessively small, stirring in the reaction cannot be successfully carried out and, in this case, the use of an excessive amount of mineral acid is sometimes necessary. On the other hand, when the amount of the solvent used is excessively large, the reaction rate is likely to be significantly lowered and, in this case, the use of an excessive amount of mineral acid is sometimes necessary for accelerating the reaction rate. The use of the excessive amount of mineral acid is likely to cause a load on wastewater treatment. Further, when the mineral acid is volatile, disadvantageously, a special removal apparatus or the like is sometimes necessary.

The amount of the mineral acid used may vary depending upon the type of the compound used. Generally, the amount of the mineral acid may be 1 to 5 times by mole, preferably 1 to 1.2 times by mole, the amount of the amine compound represented by formula (V). When the amount of the mineral acid used is excessively small, the yield is likely to be lowered. Further, this is likely to affect the next second step. Specifically, there is a possibility that the amino group which does not form any salt of the amine compound represented by formula (V) remains and is reacted with the compound represented by formula (VII) used in the next second step to give impurities. On the other hand, when the amount of the mineral acid used is excessively large, in some cases, a load is applied to wastewater treatment. Further, when the mineral acid is volatile, disadvantageously, a special removal apparatus or the like is possibly necessary.

The amine mineral acid salt compound represented by formula (VI) obtained in the first step may be purified by a conventional procedure, for example, by extraction and recrystallization, or alternatively as such may be used in the reaction in the next second step without any purification.

(ii-b) Second Step

The compounds represented by formula (VII) used in the second step are easily commercially available. Specific examples of the compounds represented by formula (VII) include 3-chloropropionic acid, 3-chlorobutyric acid, 4-chlorobutyric acid, 3-chloro-2-methylpropionic acid, 5-chlorovaleric acid, 4-chlorovaleric acid, 3-chlorovaleric acid, 4-chloro-3-methylbutyric acid, 3-chloro-3-methylbutyric acid, 6-chlorohexanoic acid, 5-chlorohexanoic acid, 4-chlorohexanoic acid, 3-chlorohexanoic acid, 5-chloro-4-methylvaleric acid, 4-chloro-4-methylvaleric acid, 5-chloro-3-methylvaleric acid, 4-chloro-3-methylvaleric acid, 5-chloro-2-methylvaleric acid, 4-chloro-2-methylvaleric acid, 3-chloro-2-methylvaleric acid, 4-chloro-2,3-dimethylbutyric acid, 3-chloro-2,3-dimethylbutyric acid, 4-chloro-3-ethylbutyric acid, 3-chloro-3-ethylbutyric acid, 4-chloro-2-ethylbutyric acid, 3-chloro-2-ethylbutyric acid, 7-chloroenanic acid, 6-chloroenanic acid, 5-chloroenanic acid, 4-chloroenanic acid, 3-chloroenanic acid, 6-chloro-5-methylhexanoic acid, 5-chloro-5-methylhexanoic acid, 4-chloro-5-methylhexanoic acid, 3-chloro-5-methylhexanoic acid, 6-chloro-4-methylhexanoic acid, 5-chloro-4-methylhexanoic acid, 4-chloro-4-methylhexanoic acid, 3-chloro-4-methylhexanoic acid, 6-chloro-3-methylhexanoic acid, 5-chloro-3-methylhexanoic acid, 4-chloro-3-methylhexanoic acid, 3-chloro-3-methylhexanoic acid, 6-chloro-2-methylhexanoic acid, 5-chloro-2-methylhexanoic acid, 4-chloro-2-methylhexanoic acid, 3-chloro-2-methylhexanoic acid, 5-chloro-3,4-dimethylvaleric acid, 4-chloro-3,4-dimethylvaleric acid, 3-chloro-3,4-dimethylvaleric acid, 3-chloro-4,4-dimethylvaleric acid, 5-chloro-2,4-dimethylvaleric acid, 4-chloro-2,4-dimethylvaleric acid, 3-chloro-2,4-dimethylvaleric acid, 5-chloro-2,3-dimethylvaleric acid, 4-chloro-2,3-dimethylvaleric acid, 5-chloro-3,3-dimethylvaleric acid, 5-chloro-2,2-dimethylvaleric acid, 4-chloro-2,2-dimethylvaleric acid, 4-chloro-2,2,3-trimethylbutyric acid, 5-chloro-3-ethylvaleric acid, 4-chloro-3-ethylvaleric acid, 3-chloro-3-ethylvaleric acid, 5-chloro-2-ethylvaleric acid, 4-chloro-2-ethylvaleric acid, 3-chloro-2-ethylvaleric acid, 4-chloro-2-ethyl-3-methylvaleric acid, 3-chloro-2-ethyl-3-methylvaleric acid, 4-chloro-2-ethyl-2-methylvaleric acid, 4-chloro-2-propylbutyric acid, 3-chloro-2-propylbutyric acid, 3-chloro-3-phenylpropionic acid, 3-chloro-3-phenyl-2-methylpropionic acid, 4-chloro-4-phenylbutyric acid, 4-chloro-4-phenyl-3-methylbutyric acid, and acid chloride compounds of the above carboxylic acids, or ester compounds of the above carboxylic acids with straight-chain or branched-chain alcohol compounds having 1 to 6 carbon atoms, for example, methyl esters, ethyl esters, propyl esters, isopropyl esters, butyl esters, isobutyl esters, pentyl esters, hexyl esters, and cyclohexyl esters.

Regarding the compounds represented by formula (VII), before use, the above carboxylic acids may be converted to carboxylic acid chloride compounds. Methods for converting carboxylic acids to carboxylic acid chloride compounds are generally known, and, for example, Japanese Patent Publication No. 026497/1982, Japanese Patent Laid-Open Nos. 089617/1977 and 199540/1999 disclose methods for producing carboxylic acid chloride compounds from carboxylic acids and thionyl chloride, phosphorus pentachloride, phosgene or the like.

The reaction temperature in the second step may vary depending upon the type of the compound used. The reaction temperature is generally 30 to 150° C., preferably 50 to 120°

C. When the reaction temperature is excessively low, the reaction rate is likely to be lowered. On the other hand, when the reaction temperature is excessively high, the salt produced in the first step is likely to be thermally decomposed.

Whether or not the solvent is to be used in the second step depends upon the type of the compound used or the like. When the amine mineral acid salt compound of formula (VI) and/or the compound of formula (VII) and/or the ester compound of formula (VIII) are liquid or melt, the reaction may be carried out in the absence of a solvent. On the other hand, when the amine mineral acid salt compound of formula (VI) and/or the compound of formula (VII) and/or the ester compound of formula (VIII) are solid or do not melt, the reaction is preferably carried out in the presence of a solvent.

Specific examples of solvents usable herein include esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the amine mineral acid salt compound of formula (VI) based on the total amount of the amine mineral acid salt compound of formula (VI), the compound of formula (VII), and the solvent is generally 1 to 50% by weight, preferably 5 to 30% by weight, more preferably 10 to 20% by weight. When the amount of the solvent used is excessively small, stirring in the reaction cannot be successfully carried out and the reaction rate is likely to be lowered. On the other hand, when the amount of the solvent used is excessively large, this does not affect the reaction. In this case, however, the amount of the solvent to be discarded is increased, and a load on environment is likely to be enhanced.

The amount of the compound represented by formula (VII) based on the amine mineral acid salt compound represented by formula (VI) may vary depending upon the type of the compound used. Generally, the amount of the compound represented by formula (VII) may be 2 to 10 times by mole, preferably 2 to 5 times by mole, the amount of the amine mineral acid salt compound represented by formula (VI). When the amount of the compound represented by formula (VII) used is excessively small, the yield is likely to be lowered and, in addition, the amount of impurities is likely to be increased. On the other hand, when the amount of the compound represented by formula (VII) used is excessively large, this does not affect the reaction at all. In this case, however, since the amount of waste is increased, disadvantageously, the load on environment is likely to be increased.

The ester compound represented by formula (VIII) obtained in the second step may be purified by a conventional procedure, for example, by extraction, recrystallization or distillation, or alternatively as such may be used in the reaction in the next third step without any purification.

(ii-c) Third Step

The reaction temperature in the third step may vary depending upon the type of the compound used. The reaction temperature is generally 30 to 150° C., preferably 50 to 120° C. When the reaction temperature is excessively low, the reaction rate is likely to be lowered. On the other hand, when the reaction temperature is excessively high, the amount of impurities is likely to be increased. Further, in this case, dehydrochlorination proceeds due to the heat, possibly leading to, polymerization of the formed unsaturated bond.

Whether or not the solvent is to be used in the third step depends upon the type of the compound used or the like. When the ester compound of formula (VIII) is liquid or melts, the reaction may be carried out in the absence of a solvent. On the other hand, when the ester compound of formula (VIII) is solid or does not melt, the reaction is preferably carried out in the presence of a solvent.

Specific examples of solvents usable herein include esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the ester compound of formula (VIII) based on the total amount of the ester compound of formula (VIII), the compound of formula (IX), and the solvent is generally 0.5 to 80% by weight, preferably 5 to 50% by weight. When the amount of the solvent used is excessively small, stirring in the reaction cannot be successfully carried out and the reaction rate is likely to be lowered. On the other hand, when the amount of the solvent used is excessively large, this does not affect the reaction. In this case, however, the amount of the solvent to be discarded is increased, and a load on environment is likely to be enhanced.

Specific examples of $Z^1$ and $Z^2$ in the compounds represented by formula (IX) used in the third step include a chlorine atom; a bromine atom; alkyloxy groups such as methoxy, ethoxy, propyoxy, iso-propyoxy, butoxy, pentaoxy, hexaoxy, and cyclohexaoxy groups; alkenyloxy groups such as vinyloxy and allyloxy groups; aryloxy groups such as phenyloxy, tolyloxy, xylyloxy, biphenyloxy, naphthyloxy, anthryloxy, and phenanthryloxy groups; residues of imidazoles such as imidazole, 2-imidazoline, 3-imidazoline, 4-imidazoline, imidazolidine, imidazolidone, ethyleneurea, and ethylenethiourea; residues of pyrazoles such as pyrazole, 1-pyrazoline, 2-pyrazoline, 3-pyrazoline, and pyrazolidone.

Dimers or trimers of the above compounds may also be used. The dimer referred to herein is a compound comprising two molecules of a compound represented by formula (IX). For example, when $Z^1$ and $Z^2$ represent a chlorine atom, the dimer is a compound represented by formula (XIV)

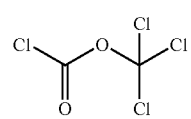

(XIV)

Further, the trimer referred to herein is a compound comprising three molecules of a compound represented by formula (IX). For example, when $Z^1$ and $Z^2$ represent a chlorine atom, the trimer is a compound represented by formula (XV)

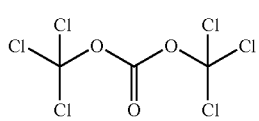
(XV)

The amount of the compound represented by formula (IX) based on the ester compound represented by formula (VIII) may vary depending upon the type of the compound used. Theoretically, the reaction between the ester compound represented by formula (VIII) and the compound represented by formula (IX) proceeds in a molar ratio of 1:1. In order to allow the reaction to proceed smoothly, however, the use of an excessive amount of the compound represented by formula (IX) is preferred. Generally, the amount of the compound represented by formula (IX) used may be 1 to 10 times by mole, preferably 1 to 5 times by mole, the amount of the ester compound represented by formula (VIII) used. When the amount of the compound represented by formula (IX) used is excessively small, a part of the ester compound represented by formula (VIII) remains unreacted. This is likely to lower the yield, and the amount of impurities is likely to be increased. On the other hand, when the amount of the compound represented by formula (IX) used is excessively large, this does not affect the reaction. In this case, however, disadvantageously, a special removal apparatus or the like is possibly necessary, and the load on environment is likely to be increased.

The isocyanate compound represented by formula (X) obtained in the third step may be purified by a conventional procedure, that is, for example, by extraction, recrystallization or distillation, or alternatively as such may be used in the reaction in the next fourth step without any purification.

(ii-d) Fourth Step

The reaction temperature in the fourth step may vary depending upon the type of the compound used. However, the reaction may be generally carried out at 0° C. to 150° C., preferably 20° C. to 100° C. When the reaction temperature is excessively low, the reaction rate is likely to be lowered. On the other hand, when the reaction temperature is excessively high, disadvantageously, the unsaturated bond produced by the dehydrochlorination is likely to be polymerized.

Whether or not the solvent is to be used in the fourth step depends upon the type of the compound used or the like. When the isocyanate compound of formula (X) is liquid or melts, the reaction may be carried out in the absence of a solvent. On the other hand, when the isocyanate compound of formula (X) is solid or does not melt, the reaction is preferably carried out in the presence of a solvent.

Specific examples of solvents usable herein include esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the isocyanate compound of formula (X) based on the total amount of the isocyanate compound of formula (X), the ethylenically unsaturated group-containing isocyanate compound of formula (I), and the solvent is generally 0.5 to 80% by weight, preferably 5 to 50% by weight. When the amount of the solvent used is excessively small, stirring in the reaction cannot be successfully carried out and the reaction rate is likely to be lowered. Further, in this case, the formed salt could not be removed without difficulties. On the other hand, when the amount of the solvent used is excessively large, this does not affect the reaction. In this case, however, the amount of the solvent to be discarded is increased, and a load on environment is likely to be enhanced.

Conventional basic nitrogen-containing compounds are usable as the basic nitrogen compound used in the fourth step. In this case, when a hydrogen atom stays on the basic nitrogen, disadvantageously, this is likely to be reacted with the isocyanate group in the isocyanate compound represented by formula (X), possibly leading to lowered yield.

Accordingly, the basic nitrogen compound is preferably a tertiary nitrogen-containing basic nitrogen compound. Further, in order to efficiently carry out the dehydrochlorination, weakly basic nitrogen compounds in which an aromatic ring is attached directly to the nitrogen atom, such as quinoline, are unsatisfactory, and the basic nitrogen compound should have a certain level of basicity. That is, preferably, the basic nitrogen compound contains a tertiary nitrogen atom which contains at least one substituent other than aromatic ring, for example, alkyl group. Further, the number of aromatic rings substituted by the tertiary nitrogen atom is preferably one or less.

Specific examples of basic nitrogen compounds used in the fourth step include trimethylamine, triethylamine, tripropylamine, dimethylethylamine, dimethylisopropylamine, diethylmethylamine, dimethylbutylamine, dimethylhexylamine, diisopropylethylamine, dimethylcyclohexylamine, tetramethyldiaminomethane, dimethylbenzylamine, tetramethylethylenediamine, tetramethyl-1,4-diaminobutane, tetramethyl-1,3-diaminobutane, tetramethyl-1,6-diaminohexane, pentamethyldiethylenetriamine, 1-methylpiperidine, 1-ethylpiperidine, N,N-methylpiperazine, N-methylmorpholine, 1,8-diazabicyclo[5.4.0.]-7-undecene (DBU), 1,5-diazabicyclo[4.3.0]-5-nonene (DBN), 2,4-diazabicyclo[2.2.2]octane (DABCO), N,N-dimethylaniline, N,N-diethylaniline, and ion exchange resins containing tertiary nitrogen.

Among them, trimethylamine, triethylamine, tripropylamine, and tetramethylenediamine are preferred. The above basic nitrogen compounds may be used solely or in a combination of two or more compounds.

The amount of the basic nitrogen compound used in the fourth step may vary depending upon the type of the compound used. In general, a method may be adopted in which the reaction solution after the completion of the reaction in the third step is measured for alkali decomposable chlorine and the basic nitrogen compound is used in such an amount so as to be 0.5 to 10 times by mole, preferably 0.8 to 5.0 times by mole, more preferably 0.9 to 2.0 times by mole, the amount of the alkali decomposable chlorine. When the amount of the basic nitrogen compound used is excessively small, disadvantageously, the yield is likely to be lowered. On the other hand, when the amount of the basic nitrogen compound used is excessively large, the stability of the resultant ethylenically unsaturated group-containing isocyanate compound represented by formula (I) is possibly deteriorated and, further, the cost required for production on a commercial scale is increased.

The amount of the alkali decomposable chlorine referred to herein is one as measured by a method which comprises diluting the reaction solution obtained in the third step with a methanol/water mixed solvent, further adding an aqueous sodium hydroxide solution to the diluted solution, then heating the mixture, and then subjecting the mixture to potentiometric titration with a silver nitrate solution to determine the amount of the alkali decomposable chlorine.

The ethylenically unsaturated group-containing isocyanate compound represented by formula (I) obtained in the fourth step may be purified by a conventional procedure, for example, filtration, extraction, recrystallization, or distillation.

(iii) Second Production Process of Ethylenically Unsaturated Group-containing Isocyanate Compound The second production process of the ethylenically unsaturated group-containing isocyanate compound according to the present invention comprises the following first to third steps.

[First Step]

A step of preparing a dihydroxyamine mineral acid salt compound represented by formula (VI)

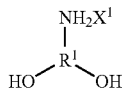

(VI)

wherein $R^1$ is as defined below, and $X^1$ represents a mineral acid, from a dihydroxyamine compound represented by formula (V)

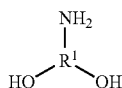

(V)

wherein $R^1$ represents a straight-chain or branched-chain saturated aliphatic group having 1 to 10 carbon atoms, and a mineral acid.

[Second Step]

A step of preparing an ester compound represented by formula (XII)

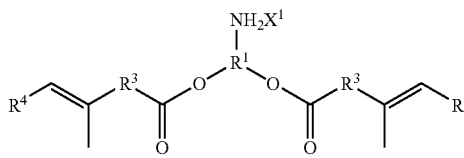

(XII)

wherein $R^1$ and $X^1$ are as defined above and $R^3$ and $R^4$ are as defined below, from the dihydroxyamine mineral acid salt compound and a compound represented by formula (XI)

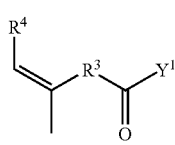

(XI)

wherein $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms.

[Third Step]

A step of preparing an ethylenically unsaturated group-containing isocyanate compound represented by formula (XIII)

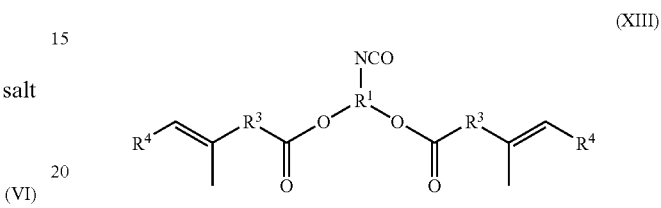

(XIII)

wherein $R^1$, $R^3$, and $R^4$ are as defined above, from the ester compound and a compound represented by general formula (IX)

(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles.

(iii-a) First Step

Details of the first step are as described in (ii-a).

(iii-b) Second Step

The compound of formula (XI) used in the second step may be commercially available one and is easily available. Specific examples of compounds represented by formula (XI) include methacrylic acid, 3-methyl-3-butenoic acid, tiglic acid, 4-methyl-4-pentenoic acid, α-methylcinnamic acid, and acid chloride compounds of the above carboxylic acids, or ester compounds of the above carboxylic acids with linear or branched alcohol compounds having 1 to 6 carbon atoms, for example, methyl esters, ethyl esters, propyl esters, isopropyl esters, butyl esters, isobutyl esters, pentyl esters, hexyl esters, and cyclohexyl esters.

The compounds represented by formula (XI) may be used after the carboxylic acid is converted to a carboxylic acid chloride compound. Methods for converting carboxylic acids to carboxylic acid chloride compounds are generally known, and, for example, Japanese Patent Publication No. 026497/1982 and Japanese Patent Laid-Open Nos. 089617/1977 and 199540/1999 disclose methods for producing carboxylic acid chloride compounds from carboxylic acids and thionyl chloride, phosphorus pentachloride, phosgene or the like.

The reaction temperature in the second step may vary depending upon the type of the compound used. Generally, the reaction may be carried out at 30° C. to 150° C., preferably 50° C. to 120° C. When the reaction temperature is excessively low, the reaction rate is likely to be lowered. On the other hand, when the reaction temperature is excessively high, disadvantageously, the amount of impurities is likely to be increased, and, further, the unsaturated bond is likely to be polymerized.

Whether or not the solvent is to be used in the second step depends upon the type of the compound used or the like. When the amine mineral acid salt compound of formula (VI) and/or the compound of formula (XI) and/or the ester compound of formula (XII) are liquid or melt, the reaction may be carried out in the absence of a solvent. On the other hand, when the amine mineral acid salt compound of formula (VI) and/or the compound of formula (XI) and/or the ester compound of formula (XII) are solid or do not melt, the reaction is preferably carried out in the presence of a solvent.

Specific examples of solvents usable herein include esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the amine mineral acid salt compound of formula (VI) based on the total amount of the amine mineral acid salt compound of formula (VI), the compound of formula (XI), and the solvent is generally 1 to 50% by weight, preferably 5 to 30% by weight, more preferably 10 to 20% by weight. When the amount of the solvent used is excessively small, stirring in the reaction cannot be successfully carried out and the reaction rate is likely to be lowered. On the other hand, when the amount of the solvent used is excessively large, this does not affect the reaction. In this case, however, the amount of the solvent to be discarded is increased, and a load on environment is likely to be enhanced.

The amount of the compound represented by formula (XI) based on the amine mineral acid salt compound represented by formula (VI) may vary depending upon the type of the compound used. Generally, the amount of the compound represented by formula (XI) may be 2 to 10 times by mole, preferably 2 to 5 times by mole, the amount of the amine mineral acid salt compound represented by formula (VI). When the amount of the compound represented by formula (XI) used is excessively small, the yield is likely to be lowered and, in addition, the amount of impurities is likely to be increased. On the other hand, when the amount of the compound represented by formula (XI) used is excessively large, this does not affect the reaction at all. In this case, however, since the amount of waste is increased, disadvantageously, the load on environment is likely to be increased.

The ester compound represented by formula (VIII) obtained in the second step may be purified by a conventional procedure, for example, by extraction, recrystallization or distillation, or alternatively as such may be used in the reaction in the next third step without any purification.

(iii-c) Third Step

The reaction temperature in the third step may vary depending upon the type of the compound used. The reaction temperature is generally 30 to 150° C., preferably 50 to 120° C. When the reaction temperature is excessively low, the reaction rate is likely to be lowered. On the other hand, when the reaction temperature is excessively high, the amount of impurities is likely to be increased. Further, in this case, polymerization of the formed unsaturated bond is likely to take place.

Whether or not the solvent is to be used in the third step depends upon the type of the compound used or the like. When the ester compound of formula (XII) is liquid or melts, the reaction may be carried out in the absence of a solvent. On the other hand, when the ester compound of formula (XII) is solid or does not melt, the reaction is preferably carried out in the presence of a solvent.

Specific examples of solvents usable herein include esters such as methyl acetate, ethyl acetate, propyl acetate, isopropyl acetate and butyl acetate; chain ethers such as diethyl ether, dipropyl ether, and dibutyl ether; cyclic ethers such as dioxane, dioxolane and tetrahydrofuran; aromatic hydrocarbons such as toluene, xylene, ethylbenzene, mesitylene, and cumene; aliphatic hydrocarbons such as propane, hexane, heptane, and cyclohexane; and halogenated hydrocarbons such as methylene chloride, 1,2-dichloroethane and 1,2-dichlorobenzene.

When the solvent is used, the amount of the solvent used is such that the concentration of the ester compound of formula (VIII) based on the total amount of the ester compound of formula (XII), the compound of formula (IX), and the solvent is generally 0.5 to 80% by weight, preferably 5 to 50% by weight. When the amount of the solvent used is excessively small, stirring in the reaction cannot be successfully carried out and the reaction rate is likely to be lowered. On the other hand, when the amount of the solvent used is excessively large, this does not affect the reaction. In this case, however, the amount of the solvent to be discarded is increased, and a load on environment is likely to be enhanced.

Specific examples of $Z^1$ and $Z^2$ in compounds represented by formula (IX) used in the third step are as described above. Further, as described above, a dimer or trimer of the compound of formula (IX) may also be used.

The amount of the compound represented by formula (IX) based on the ester compound represented by formula (XII) used may vary depending upon the type of the compound used. Theoretically, the reaction between the ester compound represented by formula (XII) and the compound represented by formula (IX) proceeds in a molar ratio of 1:1. In order to allow the reaction to proceed smoothly, however, the use of an excessive amount of the compound represented by formula (IX) is preferred. Generally, the amount of the compound represented by formula (IX) used may be 1 to 10 times by mole, preferably 1 to 5 times by mole, the amount of the ester compound represented by formula (XII) used. When the amount of the compound represented by formula (IX) used is excessively small, a part of the ester compound represented by formula (XII) remains unreacted. This is likely to lower the yield, and the amount of impurities is likely to be increased. On the other hand, when the amount of the compound represented by formula (IX) used is excessively large, this does not affect the reaction at all. In this case, however, disadvantageously, a special removal apparatus or the Like is possibly necessary, and the load on environment is likely to be increased.

The ethylenically unsaturated group-containing isocyanate compound represented by formula (XIII) obtained in the third step may be purified by a conventional procedure, that is, for example, by extraction, recrystallization or distillation, or alternatively as such may be used in the reaction in the next fourth step without any purification.

(iv) Reactive Monomer

The reactive monomer according to the present invention is produced using the above ethylenically unsaturated group-containing isocyanate compound as a starting compound and is represented by formula (Ia). In this reactive monomer, two ethylenically unsaturated groups are bonded to one urethane, thiourethane, or urea group. At least one urethane, thiourethane, or urea bond is contained in the molecule.

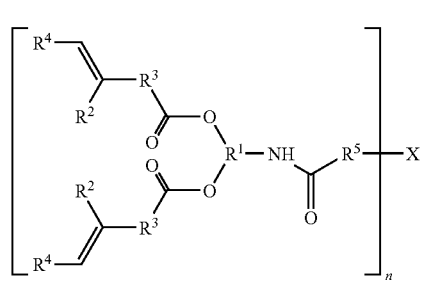
(Ia)

In the formula, $R^1$ represents a straight-chain or branched saturated aliphatic group having 1 to 10 carbon atoms, preferably 1 to 5 carbon atoms. Specific examples of preferred substituents include those obtained from the dihydroxyamine compound of formula (V) in the production process of the ethylenically unsaturated group-containing isocyanate compound. Examples thereof include those prepared from 2-amino-1,3-propanediol, 1-amino-2,3-butanediol, and 2-amino-2-methyl-1,3-butanediol.

$R^2$ represents a hydrogen atom or a methyl group.

$R^3$ represents a straight-chain or branched-chain alkylene group having 0 to 5 carbon atoms.

$R^4$ represents a hydrogen atom, a straight-chain or branched-chain alkyl group having 1 to 6 carbon atoms, or an aryl group. $R^4$ preferably represents a hydrogen atom or a methyl group from the viewpoint of the reactivity of the ethylenically unsaturated group.

Specific examples of preferred substituents include those obtained from the compound of formula (VII) or formula (XI) in the production process of the ethylenically unsaturated group-containing isocynate compound. Examples thereof include those prepared from (meth)acrylic acid chloride, crotonic acid chloride, 3-chloropropionic acid chloride, and 3-chlorobutanoic acid chloride.

$R^5$ represents an ether, thioether, or NH group, X represents an aliphatic, aromatic, or heterocyclic group bonded thereto, and n is an integer of 1 to 4. The molecular weight of X is generally less than 2000, preferably 300 to 1000.

The aliphatic group as the substitutent X is a group which comprises a straight-chain, branched-chain or cyclic carbon chain and has 1 to 4 positions which can be substituted. Specific examples thereof include straight-chain or branched-chain alkyl groups, straight-chain or branched alkylene groups, and cyclic alkyl groups.

The aliphatic group as the substituent X further may have a substituent. Specific examples of such substituents include alkyl groups such as ethyl, n-butyl, and n-hexyl groups, $-CH_2CH_2(CF_2)_8F$, and $-CH_2CF_2CF_2CF_2CF_2CF_2CF_2CH_2-$; and cyclic alkyl groups such as cyclohexyl, cycloalkenyl, and norbornyl groups.

The aromatic group as the substituent X is an aromatic group having 1 to 4 positions which can be substituted. Specific examples thereof include phenyl, xylylene, bisphenol, and fluorene groups.

The heterocyclic group as the substituent X is a heterocyclic group having 1 to 4 positions which can be substituted. Specific examples thereof include pyridyl, thienyl, furyl, piperidyl, imidazolyl, and quinolyl groups.

Specific examples of preferred reactive monomers according to the present invention include compounds represented by formulae (IIa) to (IVa).

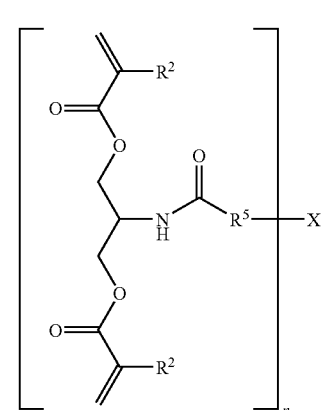
(IIa)

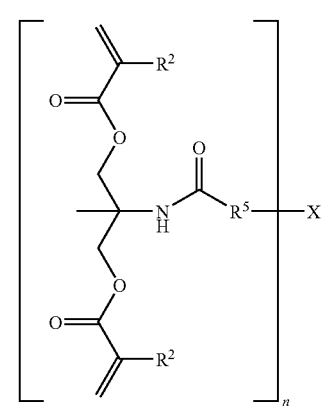
(IIIa)

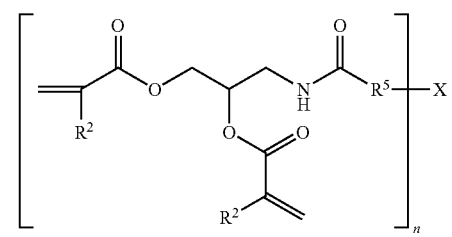
(IVa)

In formulae (IIa) to (IVa), $R^2$, $R^5$ and X are as defined above.

In the reactive monomer according to the present invention, the ethylenically unsaturated group can be photocured or heat-cured, for example, by radical or cation polymerization. In this case, as in the present invention, when a structure containing adjacent reactive ethylenically unsaturated groups is adopted, high reactivity and increased degree of crosslinking can be mentioned as the effect attained by the presence of the ethylenically unsaturated group in the adjacent position. As a result, when the reactive monomer has been brought to a curable composition, the gelation speed becomes high. When the curable composition is coated onto a reactive base material followed by curing, the adhesive strength to the base material is good. Further, the crosslinked structure is so dense that the heat resistant temperature is good.

Further, the unfavorable phenomenon that the ethylenically unsaturated group is sometimes crystallized upon curing can be suppressed. At the same time, the optical effect of good transparency can be attained. This is considered attributable to the fact that, due to the presence of adjacent ethylenically unsaturated groups, crosslinking proceeds in an amorphous manner, making it difficult to form a crystalline region upon curing. This is a critical property for applications as optical materials.

Specific examples of preferred reactive monomers in the present invention will be described for a case where $R^5$ represents an ether group, a case where $R^5$ represents a thioether group, and a case where $R^5$ represents an NH group. It should be noted that the essential feature of the present invention is that the effect is attained by the fact that two adjacent reactive ethylenically unsaturated groups are bonded to one urethane bond, thiourethane bond, or urea bond, and at least one urethane bond, thiourethane bond, or urea bond of this type is contained in its molecule, and the substituent X is not limited to the following exemplification.

Reactive Monomer in which $R^5$ Represents an Ether Group

In the reactive monomer in the first example, in formula (Ia), $R^5$ represents an ether group, X represents fluorine-containing group, and n=1. Specific examples of the fluorine-containing group having one position which can be substituted include fluoroalkyl groups. The fluoroalkyl group preferably has 1 to 20 carbon atoms, more preferably 1 to 10 carbon atoms, and may have a straight-chain structure (for example, $-CF_2CF_3$, $-CH_2(CF_2)_4H$, $-CH_2(CF_2)_8CF_3$, $-CH_2CH_2(CF_2)_4H$, or $-CH_2CH_2(CF_2)_8F$), a branched-chain structure (for example, $-CH(CF_3)_2$, $-CH_2CF(CF_3)_2$, $-CH(CH_3)CF_2CF_3$, or $-CH(CH_3)(CF_2)_5CF_2H$), an alicyclic structure (preferably a five-membered or six-membered ring, for example, a perfluorocyclohexyl group, a perfluorocyclopentyl group, or an alkyl group substituted by the above group), or may have an ether bond. Specific examples of ether bond-containing fluoroalkyl groups include $-CH_2OCH_2CF_2CF_3$, $-CH_2CH_2OCH_2C_4F_8H$, $-CH_2CH_2OCH_2CH_2C_8F_{17}$, and $-CH_2CH_2OCF_2CF_2OCF_2CF_2H$.

A plurality of fluoroalkyl groups described above may be contained in the same molecule.

An example of preferred X in formula (Ia) is a group represented by $-(CH_2)_m(CF_2)_lF$ wherein m is an integer of 0 to 2 and l is an integer of 0 to 8, provided that m and l do not simultaneously represent 0.

The fluorine content is preferably not less than 30% by weight based on the total amount of the reactive monomer, more preferably not less than 40% by weight, still more preferably not less than 50% by weight. When the fluorine content is excessively low, the refractive index value is increased. In this case, in some cases, properties as a low-refractive index material cannot be provided when the product is used as an antireflection film or a cladding material. For example, when the fluorine content is less than 40% by weight, in some cases, the refractive index is not less than 1.45. This refractive index is not appropriate as a low-refractive index material. The fluorine content based on the total amount of the composition can be brought to not less than 50% by weight by preparing the composition using the reactive monomer as one component.

In the reactive monomer in the second example, in formula (Ia), $R^5$ represents an ether group, X represents a fluorine-containing group, and n=2. The fluorine-containing group having two positions which can be substituted is preferably a group obtained from a fluorine-containing diol. Specific examples of fluorine-containing diols include perfluoroalkyl diols such as 2,2,3,3,4,4-hexafluoro-1,5-pentanediol, 2,2,3,3,4,4,5,5-octafluoro-1,6-hexanediol, and 2,2,3,3,4,4,5,5,6,6,7,7-dodecafluoro-1,8-octanediol; perfluoroalkylene glycols such as perfluorotriethylene glycol and perfluorotetraethylene glycol; polyperfluoroalkylene ether diols such as α-(1,1-difluoro-2-hydroxyethyl)-ω-(2,2-difluoroethanol)poly(oxy-1,1,2,2-tetrafluoroethylene), α-(1,1-difluoro-2-hydroxyethyl)-ω-(2,2-difluoroethanol)poly(oxy-difluoromethylene), and α-(1,1-difluoro-2-hydroxyethyl)-ω-(2,2-difluoroethanol)poly(oxy-difluoromethylene) (oxy-1,1,2,2-tetrafluoroethylene); ring-opened diols of fluoroalkyl epoxides such as 3-perfluorobutyl-1,2-epoxypropane, 3-perfluorooctyl-1,2-epoxypropane, and 3-perfluorobutyl-1,2-epoxypropane; and 2,2-bis(4-hydroxycyclohexyl)hexafluoropropane. A group obtained from a diol comprising an alkylene oxide such as ethylene oxide or propylene oxide added to the fluorine-containing diol may also be used.

The preferred fluorine content range based on the total amount of the reactive monomer is the same as described above in connection with the first example.

In the reactive monomer in the third example, in formula (Ia), $R^5$ represents an ether group, X represents a group having a fluorene skeleton, and n=2. A group represented by formula (XVI) may be mentioned as the fluorene skeleton-containing group.

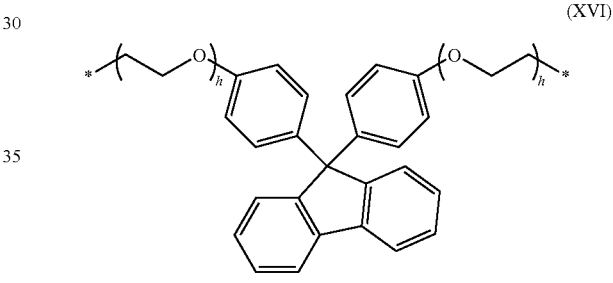
(XVI)

In formula (XVI), h is preferably 1 to 4, more preferably 1 or 2.

Reactive Monomer in which $R^5$ Represents NH Group

In the reactive monomer in the first example, $R^5$ in formula (Ia) represents NH group, X represents a fluorine-containing group, and n=1. The same group as in the case where $R^5$ represents an ether group may be mentioned as the fluorine-containing group having one position which can be substituted. Specific examples of preferred fluorine-containing groups include aromatic groups such as $F(CF_2)_3CH_2-$, $F(CF_2)_6CH_2-$, $F(CF_2)_7CH_2-$, $F(CF_2)_8CH_2-$, and a residue of 2,6-difluoroaniline.

In the reactive monomer in the second example, in formula (Ia), $R^5$ represents NH group, X represents a saturated aliphatic group or aromatic group, and n=2. Saturated aliphatic groups include, for example, groups of straight-chain, branched-chain or cyclic carbon chains having two positions which can be substituted. Specific examples thereof include groups having an alkylene straight-chain structure such as ethylene, propylene, butylene, hexamethylene, and polyoxyalkylene, and groups having an alicyclic structure such as cyclohexyl and norbornane.

Aromatic groups include phenylene, xylylene, 4,4'-methylenebis(phenylamine), 2,3,5,6-tetrafluoro-phenyl, and 2,3,5,6-tetrafluoro-1,4-xylylenyl groups.

Reactive Monomer in which $R^5$ Represents Thioether Group

The substituent X in the case where $R^5$ represents a thioether group may be the same group as described above in connection with the case where $R^5$ represents an ether group or NH group. Specific examples of the substituent X include those obtained by adding an isocyanate group in the ethylenically unsaturated group-containing isocyanate compound of formula (I) to the following compound containing one or more mercapto group. Specific examples of compounds containing one or more mercapto groups include methyl mercaptan, ethyl mercaptan, propyl mercaptan, butyl mercaptan, amyl mercaptan, hexyl mercaptan, heptyl mercaptan, octyl mercaptan, nonyl mercaptan, cyclopentyl mercaptan, cyclohexyl mercaptan, furfuryl mercaptan, thiophenol, thiocresol, ethylthiophenol, benzyl mercaptan, 1,2-ethanedithiol, 1,2-propanedithiol, 1,3-propanedithiol, 1,4-butanedithiol, 1,6-hexanedithiol, 1,2,3-propanetrithiol, 1,1-cyclohexanedithiol, 1,2-cyclohexanedithiol, bicyclo[2,2,1]hepta-exo-cis-2,3-dithiol, 1,1-bis(mercaptomethyl)cyclohexane, bis(2-mercaptoethyl)ether, ethyleneglycol bis(2-mercaptoacetate), ethyleneglycol bis(3-mercaptopropionate), trimethylolpropanebis(2-mercaptoacetate), trimethylolpropanebis(3-mercaptopropionate), pentaerythritol tetrakis(2-mercaptoacetate), pentaerythritol tetrakis(3-mercaptopropionate), 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(2-mercaptoethyl)benzene, 1,3-bis(2-mercaptoethyl)benzene, 1,4-bis(2-mercaptoethyl)benzene, 1,2-bis(2-mercaptoethyleneoxy)benzene, 1,3-bis(2-mercaptoethyleneoxy)benzene, 1,4-bis(2-mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(2-mercaptoethyl)benzene, 1,2,4-tris(2-mercaptoethyl)benzene, 1,3,5-tris(2-mercaptoethyl)benzene, 1,2,3-tris(2-mercaptoethyleneoxy)benzene, 1,2,4-tris(2-mercaptoethyleneoxy)benzene, 1,3,5-tris(2-mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(2-mercaptoethyl)benzene, 1,2,3,5-tetrakis(2-mercaptoethyl)benzene, 1,2,4,5-tetrakis(2-mercaptoethyl)benzene, 1,2,3,4-tetrakis(2-mercaptoethyleneoxy)benzene, 1,2,3,5-tetrakis(2-mercaptoethyleneoxy)benzene, 1,2,4,5-tetrakis(2-mercaptoethyleneoxy)benzene, 2,2'-dimercaptobiphenyl, 4,4'-thiobis-benzenethiol, 4,4'-dimercaptobiphenyl, 4,4'-dimercaptobibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-bis(2-mercaptoethylthio)benzene, 1,4-bis(2-mercaptoethylthio)benzene, 1,2-bis(2-mercaptoethylthiomethyl)benzene, 1,3-bis(2-mercaptoethylthiomethyl)benzene, 1,4-bis(2-mercaptoethylthiomethyl)benzene, 1,2,3-tris(2-mercaptoethylthio)benzene, 1,2,4-tris(2-mercaptoethylthio)benzene, 1,3,5-tris(2-mercaptoethylthio)benzene, 1,2,3,4-tetrakis(2-mercaptoethylthio)benzene, 1,2,3,5-tetrakis(2-mercaptoethylthio)benzene, 1,2,4,5-tetrakis(2-mercaptoethylthio)benzene, bis(2-mercaptoethyl)sulfide, bis(2-mercaptoethylthio)methane, 1,2-bis(2-mercaptoethylthio)ethane, 1,3-bis(2-mercaptoethylthio)propane, 1,2,3-tris(2-mercaptoethylthio)propane, tetrakis(2-mercaptoethylthiomethyl)methane, 1,2-bis(2-mercaptoethylthio)propanethiol, 2,5-dimercapto-1,4-dithiane, bis(2-mercaptoethyl)disulfide, 3,4-thiophenedithiol, 1,2-bis(2-mercaptoethyl)thio-3-mercaptopropane, and bis-(2-mercaptoethylthio-3-mercaptopropane) sulfide. Among them, octyl mercaptan, 1,6-hexanedithiol, 2-mercaptoethyl sulfide, and 1,4-dimercaptobenzene are preferred.

(v) Production Process of Reactive Monomer

The reactive monomer of formula (Ia) in the present invention can be prepared by reacting the isocyanate compound containing two reactive ethylenically unsaturated groups represented by formula (I) with a compound containing a hydroxyl, amino or mercapto group. In this case, the reaction method is not particularly limited, and, for example, the reactive monomer of formula (I) may be produced by mere mixing.

In reacting the ethylenically unsaturated group-containing isocyanate compound of formula (I) with the hydroxyl group-containing compound, the use of a urethanation catalyst is preferred. The use of this catalyst can significantly accelerate the reaction.

Specific examples of urethanation catalysts include dibutyltin dilaurate, copper naphthenate, cobalt naphthenate, zinc naphthenate, triethylamine, 1,4-diazabicyclo[2.2.2]octane, and 2,6,7-trimethyl-1,4-diazabicyclo[2.2.2]octane. These urethanation catalyst may be used either solely or in a combination of two or more.

The amount of the urethanation catalyst added is preferably 0.01 to 5 parts by weight, more preferably 0.1 to 1 part by weight, based on 100 parts by weight of the isocyanate compound. When the amount of the urethanation catalyst added is less than 0.01 part by weight, the reactivity is sometimes significantly lowered. On the other hand, when the amount of the urethanation catalyst added exceeds 5 parts by weight, in some cases, a side reaction takes place in the reaction.

The reaction temperature in the reaction between the ethylenically unsaturated group-containing isocyanate compound of formula (I) and the compound containing a hydroxyl, amino, or mercapto group is preferably −10 to 100° C., more preferably 0 to 80° C. In the reaction with the amino group, the reaction rate is so high that mere mixing can achieve a contemplated synthesis even in the absence of a catalyst. When the reaction temperature is excessively high, there is a fear that by-products are produced as a result of a further reaction of the formed urea bond with the isocyanate.

It is known that the above reaction proceeds even in the case of groups other than the hydroxyl, amino, and mercapto groups. For example, since the isocyanate group can also be reacted with a carboxyl group or the like, the reactive ethylenically unsaturated group can be introduced by an addition reaction.

Further, the ethylenically unsaturated group-containing isocyanate compound of formula (I) may be used with an isocyanate compound containing one reactive ethylenically unsaturated group for a reaction with a hydroxyl-, amino-, or mercapto-containing compound. Specific examples of isocyanate compounds containing one reactive ethylenically unsaturated group include 2-methacryloyloxyethylisocyanate, 2-acryloyloxyethylisocyanate, 2-(2-ethylbutenoyloxy)-ethylisocyanate, 2-(2-propylbutenoyloxy)ethylisocyanate, methacryloyloxymethylisocyanate, acryloyloxymethyl-isocyanate, (2-ethylbutenoyloxy)methylisocyanate, (2-propylbutenoyloxy)methylisocyanate, 3-methacryloyloxy-propylisocyanate, 3-acryloyloxypropylisocyanate, 3-(2-ethylbutenoyloxy)propylisocyanate, 3-(2-propylbutenoyloxy)-propylisocyanate, 4-methacryloyloxybutylisocyanate, 4-acryloyloxybutylisocyanate, 4-(2-ethylbutenoyloxy)-butylisocyanate, and 4-(2-propylbutenoyloxy)butylisocyanate.

(vi) Curable Composition

The curable composition according to the present invention comprises a reactive monomer of formula (Ia) and a polymerization initiator. Photopolymerization initiators may be used as the polymerization initiator. The application of an actinic radiation such as ultraviolet light or visible light can induce a polymerization reaction of the reactive monomer to prepare a cured product. Specific examples of such photopolymerization initiators include 1-hydroxycyclohexyl phenyl ketone, 2,2'-dimethoxy-2-phenylacetophenone, xanthone, fluorene, fluorenone, benzaldehyde, anthraquinone, triphenyl amine, carbazole, 3-methylacetophenone, 4-chlorobenzophenone, 4,41-dimethoxybenzophenone, 4,4'-diaminobenzophenone, Michler's ketone, benzoylpropyl ether, benzoin ethyl ether, benzyldimethylketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholinopropan-1-one, 2,4,6-trimethylbenzoyldiphenylphosphine oxide, 2-benzyl-2-dimethylamino-1-(4-morpholinophenyl)butan-1-one, and 1-[4-(2-hydroxyethoxy)-phenyl]-2-hydroxy-2-methyl-propan-1-one.

Among them, 2,4,6-trimethylbenzoyldiphenylphosphine oxide and 1-hydroxycyclohexyl phenyl ketone are preferred.

These photopolymerization initiators may be used either solely or in a combination of two or more of them.

Further, the application of heat can induce a polymerization reaction of the reactive monomer to prepare a cured product. Specifically, a heat curable composition can be produced by adding a thermal polymerization initiator to a reactive monomer. Examples of such thermal polymerization initiators include diacyl peroxides, ketone peroxides, hydroperoxides, dialkyl peroxides, peroxy esters, azo compounds, and persulfates. They may be used either solely or in a combination of two or more of them.

The amount of the polymerization initiator used is preferably 0.1 to 20 parts by weight, more preferably 0.5 to 10 parts by weight, based on 100 parts by weight of the reactive monomer. When the amount of the polymerization initiator used is less than 0.1 part by weight, in some cases, the rate of polymerization of the reactive monomer is lowered. Further, in this case, the reactive monomer is sometimes likely to undergo inhibition of polymerization by oxygen or the like. On the other hand, when the amount of the polymerization initiator used exceeds 20 parts by weight, the polymerization reaction is suppressed, often resulting in lowered strength, adhesive strength and heat resistance of the cured film. Further, this is causative of coloring.

The curable composition according to the present invention may contain a reactive monomer other than the reactive monomer of formula (Ia). The incorporation of this reactive monomer can modify the viscosity of the composition and, at the same time, can regulate properties of the cured product, for example, mechanical properties such as reactivity, hardness, elasticity, and adhesion, and optical properties such as transparency.

Specific examples of such reactive monomers include ethylenically unsaturated aromatic compounds such as styrene, α-methylstyrene, o-methylstyrene, m-methylstyrene, p-methylstyrene, p-tert-butylstyrene, diisopropenyl benzene, o-chlorostyrene, m-chlorostyrene, p-chlorostyrene, 1,1-diphenylethylene, p-methoxystyrene, N,N-dimethyl-p-aminostyrene, N,N-diethyl-p-aminostyrene, ethylenically unsaturated pyridine, and ethylenically unsaturated imidazole; carboxyl group-containing compounds such as (meth)acrylic acid, crotonic acid, maleic acid, fumaric acid, and itaconic acid; alkyl(meth)acrylates such as methyl(meth)acrylate, ethyl(meth)acrylate, propyl(meth)acrylate, isopropyl(meth)acrylate, butyl(meth)acrylate, isobutyl(meth)acrylate, tert-butyl(meth)acrylate, pentyl(meth)acrylate, amyl(meth)acrylate, isoamyl(meth)acrylate, hexyl(meth)acrylate, heptyl(meth)acrylate, octyl(meth)acrylate, isooctyl(meth)acrylate, 2-ethylhexyl(meth)acrylate, nonyl(meth)acrylate, decyl(meth)acrylate, isodecyl(meth)acrylate, undecyl(meth)acrylate, dodecyl(meth)acrylate, lauryl(meth)acrylate, stearyl(meth)acrylate, and isostearyl(meth)acrylate; fluoroalkyl(meth)acrylates such as trifluoroethyl(meth)acrylate, tetrafluoropropyl(meth)acrylate, hexafluoroisopropyl(meth)acrylate, octafluoropentyl(meth)acrylate, and heptadecafluorodecyl(meth)acrylate; hydroxyalkyl(meth)acrylates such as hydroxyethyl(meth)acrylate, hydroxypropyl(meth)acrylate, and hydroxybutyl(meth)acrylate; phenoxyalkyl(meth)acrylates such as phenoxyethyl(meth)acrylate, and 2-hydroxy-3-phenoxypropyl(meth)acrylate; alkoxyalkyl(meth)acrylates such as methoxyethyl(meth)acrylate, ethoxyethyl(meth)acrylate, propoxyethyl(meth)acrylate, butoxyethyl(meth)acrylate, and methoxybutyl(meth)acrylate; polyethylene glycol(meth)acrylates such as polyethylene glycol mono(meth)acrylate, ethoxydiethylene glycol(meth)acrylate, methoxypolyethylene glycol(meth)acrylate, phenoxypolyethylene glycol(meth)acrylate, and nonylphenoxypolyethylene glycol(meth)acrylate; polypropylene glycol(meth)acrylates such as polypropylene glycol mono(meth)acrylate, methoxypolypropylene glycol(meth)acrylate, ethoxypolypropylene glycol(meth)acrylate, and nonylphenoxypolypropylene glycol(meth)acrylate; cycloalkyl(meth)acrylates such as cyclohexyl(meth)acrylate, 4-butylcyclohexyl(meth)acrylate, dicyclopentanyl(meth)acrylate, dicyclopentenyl(meth)acrylate, dicyclopentadienyl(meth)acrylate, bornyl(meth)acrylate, isobornyl(meth)acrylate, and tricyclodecanyl(meth)acrylate; benzyl(meth)acrylate, tetrahydrofurfuryl(meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, tripropylene glycol di(meth)acrylate, polypropylene glycol di(meth)acrylate, neopentyl glycol di(meth)acrylate, 1,3-propanediol di(meth)acrylate, 1,4-butanediol di(meth)acrylate, 1,6-hexanediol di(meth)acrylate, hydroxy pivalic acid ester neopentyl glycol di(meth)acrylate, bisphenol A di(meth)acrylate, trimethylolpropane tri(meth)acrylate, pentaerythritol tri(meth)acrylate, trimethylolpropane trioxyethyl(meth)acrylate, tris(2-hydroxyethyl)isocyanurate tri(meth)acrylate, and dipentaerythritol hexa(meth)acrylate. These reactive monomers may be used either solely or in a combination of two or more of them.

In the production of the curable composition according to the present invention, mixing and regulation may be carried out by mixing the reactive monomer of formula (Ia) with a polymerization initiator at room temperature or with heating in a mixing machine such as a mixer, a ball mill or triple roll, or by adding and dissolving a reactive monomer, a solvent or the like as a diluent in the reaction system. Specific examples of reactive monomers usable as the diluent include the above-described reactive monomers. Specific examples of solvents include esters such as ethyl acetate, butyl acetate and isopropyl acetate; ketones such as acetone, methyl ethyl ketone, methyl isobutyl ketone and cyclohexanone; cyclic ethers such as tetrahydrofuran and dioxane; amides such as N,N-dimethylformamide; aromatic hydrocarbons such as toluene; and halogenated hydrocarbons such as methylene chloride.

The curable composition according to the present invention can be cured, for example, by coating a curable composition onto a base material to form a coating film and then applying a radiation or heat to the coating film. Both the radiation and heat may also be simultaneously applied for curing purposes.

The thickness of the coating film is preferably 1 to 200 μm for evaluation purposes but may be properly determined depending upon applications.

Coating methods usable herein include, for example, coating by a die coater, a spin coater, a spray coater, a curtain coater, or a roll coater, coating by screen printing, or coating by dipping.

An electron beam or light in the wavelength range of ultraviolet light to infrared light is preferred as the radiation for curing. For example, use may be made of ultrahigh pressure mercury light sources or metal halide light sources for ultraviolet light; metal halide light sources or halogen light sources for visual light sources; and halogen light sources for infrared light. In addition to the above light sources, light sources such as laser or LEDs may be used. The dose of the radiation may be properly determined depending upon the type of the light source, the thickness of the coating film and the like.

The curable composition according to the present invention can be used in applications such as resists (for example, solder resists, etching resists, color filter resists, and spacers), sealing (for example, waterproof sealing), paints (for example, antifouling paints, fluoropaints, and water-based paints), pressure-sensitive adhesives and adhesives (for example, adhesives and dicing tapes), printing plates (for example, CTP plates and offset plates), printing proofreading (for example, colorproof), lenses (for example, contact lenses, microlenses, and optical waveguides), dental materials, surface treatment (for example, optical fiber coating and disk coating), and battery materials (for example, solid electrolytes).

(vii) Reactive (meth)acrylate Polymer (A)

The reactive (meth)acrylate polymer (A) according to the present invention is a compound produced by reacting an isocyanate compound represented by formula (I) containing two adjacent ethylenically unsaturated groups in its molecule with a polymer compound comprising repeating units to which an active hydrogen-containing functional group is attached. All general formulae in the present specification embrace all stereoisomers such as cis and trans isomers.

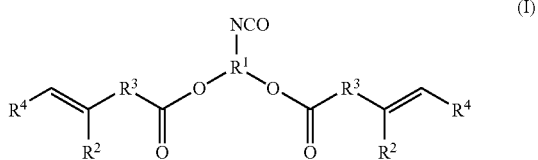

wherein $R^1$ represents a straight-chain or branched-chain saturated aliphatic group having 1 to 10, preferably 1 to 5 carbon atoms, and $R^2$ represents a hydrogen atom or a methyl group. More preferably, $R^1$ represents a branched saturated aliphatic group having 3 or 4 carbon atoms from the viewpoint of easiness in synthesizing the isocyanate group. $R^3$ represents a straight-chain or branched-chain alkylene group having 0 to 5 carbon atoms, preferably 0 to 3 carbon atoms. $R^4$ represents a hydrogen atom, a straight-chain or branched-chain alkyl group having 1 to 6 carbon atoms, or an aryl group. Preferably, $R^4$ represents a hydrogen atom, a methyl group, or an aryl group.

Specific examples of preferred isocyanate compounds include compounds represented by formulae (II) and (III).

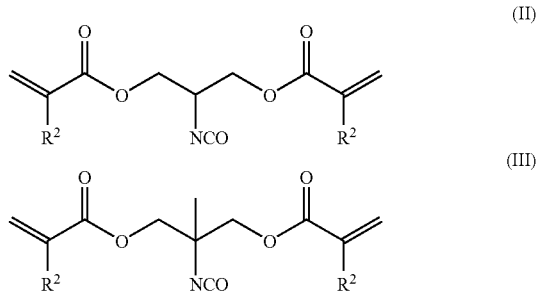

In formulae (II) and (III), $R^2$ represents a hydrogen atom or a methyl group.

Here the polymer compound which is reacted with the isocyanate compound of formula (I) comprises repeating units to which an active hydrogen-containing functional group such as a hydroxyl, amino, or mercapto group is attached. The hydroxyl, amino, or mercapto group is reacted with the isocyanate group in the isocyanate compound of formula (I) to form a urethane, urea, or thiourethane bond.

The repeating units to which an active hydrogen-containing functional group is attached refer to repeating units based on a monomer(s) containing this functional group or capable of forming the functional group through a polymerization reaction. The above polymer compound is obtained by polymerizing the monomer(s). The polymer compound may be a homopolymer prepared from an identical type of monomer or a copolymer prepared from mutually different monomers.

The above polymer compound is preferably a polyhydroxy compound comprising repeating units.

The number average molecular weight (a value determined in terms of polystyrene by gel permeation chromatography (parts by mass; PC)) of the reactive (meth)acrylate polymer (A) according to the present invention is generally 500 to 100,000, preferably 8,000 to 40,000.

(viii) Production Process of Reactive (meth)acrylate Polymer (A)

The reactive (meth)acrylate polymer (A) is prepared by reacting the isocyanate compound of formula (I) with a polymer compound comprising repeating units to which an active hydrogen-containing functional group is attached. The reaction method is not particularly limited, and, for example, the reactive (meth)acrylate polymer (A) may be prepared by merely mixing these compounds together.

In reacting the isocyanate group in the isocyanate compound of formula (I) with the hydroxyl group in the polyhydroxy compound, the use of a urethanation catalyst is preferred. The use of this catalyst can significantly accelerate the reaction.

Specific examples of urethanation catalysts include dibutyltin dilaurate, copper naphthenate, cobalt naphthenate, zinc naphthenate, triethylamine, 1,4-diazabicyclo[2.2.2]octane, and 2,6,7-trimethyl-1,4-diazabicyclo[2.2.2]octane. These urethanation catalyst may be used either solely or in a combination of two or more.

The amount of the urethanation catalyst added is preferably 0.01 to 5 parts by weight, more preferably 0.1 to 1 part by weight, based on 100 parts by weight of the isocyanate compound of formula (I). When the amount of the urethanation catalyst added is less than 0.01 part by weight, the reactivity is sometimes significantly lowered. On the other hand, when the amount of the urethanation catalyst added exceeds 5 parts by weight, in some cases, a side reaction takes place in the reaction.

The reaction temperature in the reaction between the isocyanate compound of formula (I) and the polyhydroxy compound comprising repeating units is preferably −10 to 100° C., more preferably 0 to 80° C.

(ix) Polyhydroxy Compound Comprising Repeating Units

Polyhydroxy compounds comprising repeating units usable in the present invention include polyester polyol compounds, polycarbonate polyol compounds, polyether polyol compounds, polyurethane polyol compounds, homo- or copolymers of hydroxyalkyl(meth)acrylate, or epoxy (meth) acrylate compounds.

(ix-a) Polyester Polyol Compound

The polyester polyol compound used in the present invention is a compound having two or more hydroxyl groups and one or more ester bonds per molecule, and specific examples thereof include polyester polyols prepared from polyhydric alcohols and esters of polybasic acids, and polylactonediols such as polycaprolactonediols and polybutyrolactonediols. Further, polyester polyol compounds which have been synthesized so that the carboxyl group remains unchanged may also be used.

(ix-b) Polycarbonate Polyol Compound

The polycarbonate polyol used in the present invention is a compound having two or more hydroxyl groups and one or more carbonate bonds per molecule. Among others, compounds represented by formula (XVIII) are preferred:

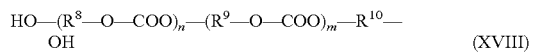

(XVIII)

wherein $R^8$, $R^9$, and $R^{10}$ each independently represent a straight-chain, branched-chain or cyclic hydrocarbon group which may contain a hydroxyl group and/or a carboxyl group and have 2 to 30 carbon atoms; and m and n are each independently an integer of 0 to 100.

$R^8$, $R^9$, and $R^{10}$ preferably represent an alkylene group having 2 to 12 carbon atoms, and specific examples thereof include ethylene, trimethylene, tetramethylene, pentamethylene, hexamethylene, propylene, 2,2-dimethyl-1,3-propylen, 1,2-cyclohexylene, 1,3-cyclohexylene, and 1,4-cyclohexylene groups.

The polycarbonate polyol compound may be prepared, for example, by reacting a diaryl carbonate such as diphenyl carbonate with a polyol such as ethylene glycol, tetramethylene glycol, hexamethylene glycol, trimethylolethane, trimethylolpropane, glycerin, or sorbitol.

(ix-c) Polyether Polyol Compound

The polyether polyol compound used in the present invention is preferably a compound having a structure formed by dehydrocondensation of two or more alkylene glycols. This compound is produced, for example, by condensation of an alkylene glycol or ring-opening polymerization of an alkylene oxide.

Specific examples of alkylene glycols include ethylene glycol, propylene glycol, 1,4-butanediol, 1,3-butanediol, 1,5-pentanediol, neopentylglycol, 3-methyl-1,5-pentanediol, 1,6-hexanediol, and 1,4-cyclohexanedimethanol.

Specific examples of alkylene oxides include ethylene oxide, propylene oxide, tetrahydrofuran, styrene oxide, and phenyl glycidyl ether.

Specific examples of polyether polyol compounds include polyethylene glycol, polypropylene glycol, ethylene oxide/propylene oxide copolymer, polytetramethylene glycol, and polyhexamethylene glycol.

(ix-d) Polyurethane Polyol Compound

The polyurethane polyol compound used in the present invention has two or more hydroxyl groups and one or more urethane bonds per molecule. They may be produced by reacting a polyisocyanate with a polyol by any proper method. In this reaction, the isocyanate compound of formula (I) may also be charged into the reaction system to produce the reactive (meth)acrylate polymer (A).

Specific examples of polyisocyanates include diisocyanates such as 2,4-toluene diisocyanate, 2,6-toluene diisocyanate, isophorone diisocyanate, hexamethylene diisocyanate, diphenylmethylene diisocyanate (o, m, or p)-xylene diisocyanate, methylenebis(cyclohexylisocyanate), trimethylhexamethylene diisocyanate, cyclohexane-1,3-dimethylene diisocyanate, cyclohexane-1,4-dimethylene diisocyanate, and 1,5-naphthalene diisocyanate. These polyisocyanates may be used either solely or in a combination of two or more of them.

Specific examples of polyols include ethylene glycol, propylene glycol, diol compounds such as 1,4-butanediol, 1,3-butanediol, 1,5-pentanediol, neopentylglycol, 3-methyl-1,5-pentanediol, 1,6-hexanediol, 1,4-cyclohexanedimethanol, glycerin, triol compounds such as trimethylol propane, pentaerythritol, dipentaerythritol, and diglycerin.

Polyol compounds usable herein include carboxyl-containing polyol compounds such as dihydroxy aliphatic carboxylic acids. These compounds are preferred because an alkali developing property can be imparted by introducing a carboxyl group into the reactive (meth)acrylate polymer (A).

Such carboxyl-containing polyol compounds include dimethyolpropionic acid and dimethylolbutanoic acid. They may be used either solely or in a combination of two or more of them.

Polyester polyol compounds in the above (ix-a), polycarbonate polyol compounds in the above (ix-b), and polyether polyol compounds in the above (ix-c) may be used as the polyol.

(ix-e) Homo- or Copolymer of hydroxyalkyl(meth)acrylate

The homo- or copolymer of the hydroxyalkyl(meth)acrylate used in the present invention is a polymer produced by homopolymerizing or copolymerizing one or more hydroxyalkyl(meth)acrylates by any proper method. Specific examples of hydroxyalkyl(meth)acrylates usable herein include 2-hydroxyethyl(meth)acrylate, hydroxypropyl (meth)acrylate, hydroxybutyl(meth)acrylate, glycerin mono (meth)acrylate, glycerin di(meth)acrylate, trimethylol propane mono(meth)acrylate, pentaerythritol mono(meth) acrylate, dipentaerythritol mono(meth)acrylate, ditrimethylol propane mono(meth)acrylate, trimethylolpropane-alkylene oxide adduct-mono(meth)acrylate, 2-hydroxy-3-phenoxypropylacrylate, polyethylene glycol(meth) acrylate, and 6-hydroxyhexanoyloxyethyl(meth)acrylate.

Among them, 2-hydroxyethyl(meth)acrylate, hydroxypropyl(meth)acrylate, and hydroxybutyl(meth)acrylate are preferred, and 2-hydroxyethyl(meth)acrylate is more preferred. These hydroxyl-containing (meth)acrylates may be used either solely or in a combination of two or more of them.

The constituent(s) other than the hydroxyalkyl(meth)acrylate constituting the copolymer is an unsaturated compound copolymerizable therewith, and specific examples thereof include alkyl(meth)acrylates such as methyl(meth)acrylate, ethyl(meth)acrylate, propyl(meth)acrylate, butyl(meth)acrylate, isobutyl(meth)acrylate, sec-butyl(meth)acrylate, tert-butyl(meth)acrylate, hexyl(meth)acrylate, octyl(meth)acrylate, isooctyl(meth)acrylate, 2-ethylhexyl(meth)acrylate, decyl(meth)acrylate, lauryl(meth)acrylate, and stearyl(meth)acrylate; alicyclic(meth)acrylates such as cyclohexyl(meth)acrylate, bornyl(meth)acrylate, isobornyl(meth)acrylate, dicyclopentenyl(meth)acrylate, and dicyclopentenyloxyethyl(meth)acrylate; aromatic(meth)acrylates such as benzyl(meth)acrylate, phenyl(meth)acrylate, phenyl carbitol(meth)acrylate, nonylphenyl(meth)acrylate, nonylphenyl carbitol(meth)acrylate, and nonylphenoxy(meth)acrylate; amino group-containing (meth)acrylates such as 2-dimethylaminoethyl(meth)acrylate, 2-diethylaminoethyl(meth)acrylate, and 2-tert-butylaminoethyl(meth)acrylate; phosphorus-containing methacrylates such as methacryloxy ethylphospliate, bis-methacryloxy ethylphosphate, and methacryloxy ethyl phenyl acid phosphate (phenyl P); glycidyl(meth)acrylates; allyl(meth)acrylates; and phenoxyethyl acrylates.

Other unsaturated compounds usable herein include carboxyl- or acid anhydride-containing unsaturated compounds such as (meth)acrylic acid, itaconic acid, maleic anhydride, itaconic anhydride, polycaprolactone(meth)acrylate, (meth)acryloyloxyethyl phthalate, and (meth)acryloyloxyethyl succinate.

The expression "(meth)acrylate" or the like as used herein refers to methacrylate and/or acrylate.

Further, N-vinyl compounds such as N-vinylpyrrolidone, N-vinylformamide, N-vinylacetamide, and vinyl aromatic compounds such as styrene and vinyltoluene are also preferred.

(ix-f) Epoxy(meth)acrylate Compound

The epoxy(meth)acrylate compound is a compound comprising an unsaturated monocarboxylic acid added to an epoxy group in an epoxy resin. In some cases, a polybasic acid anhydride is further reacted. Specific examples of epoxy resins usable herein include bisphenol A-type epoxy resins, bisphenol F-type epoxy resins, bisphenol S-type epoxy resins, novolac epoxy resins, (o-, m-, or p-)cresol novolac epoxy resins, phenol novolac epoxy resins, naphthol modified novolac epoxy resins, and halogenated phenol novolac epoxy resins.

Among them, carboxylic acid group-containing epoxy (meth)acrylate resins prepared using, as a starting material, novolac-type epoxy resins such as novolac epoxy resins, (o-, m-, or p-) cresol novolac epoxy resins, phenol novolac epoxy resins, naphthol modified novolac epoxy resins, and halogenated phenol novolac epoxy resins are preferred from the viewpoint of photosensitivity.

The number average molecular weight (a value determined in terms of polystyrene as determined by gel permeation chromatography (parts by mass; PC)) of the reactive (meth)acrylate polymer (A) according to the present invention is generally 500 to 100,000, preferably 8,000 to 40,000. When the number average molecular weight is less than 500, the film strength is significantly lowered. On the other hand, when the number average molecular weight exceeds 40,000, the developing property and flexibility are deteriorated.

When the reactive (meth)acrylate polymer (A) according to the present invention is used in the resist, the acid value is preferably 5 to 150 mgKOH/g, more preferably 30 to 120 mgKOH/g. When the acid value is less than 5 mgKOH/g, the alkali developing property is sometimes deteriorated. On the other hand, when the acid value exceeds 150 mgKOH/g, the alkali resistance, electrical characteristics and the like of the cured film are sometimes deteriorated.

For the carboxyl-containing compounds among the polyhydroxy compounds comprising repeating units, the isocyanate of formula (I) is reacted with the carboxyl group under certain reaction conditions to form an amide bond. The compound of formula (I) may also be added through this reaction.

Further, the isocyanate compound of formula (I) may be used with an isocyanate compound containing one reactive ethylenically unsaturated group for a reaction with a hydroxyl-(or amino- or mercapto-)containing polymer compound. Specific examples of isocyanate compounds containing one reactive ethylenically unsaturated group include 2-methacryloyloxyethylisocyanate, 2-acryloyloxyethylisocyanate, 2-(2-ethylbutenoyloxy)-ethylisocianate, 2-(2-propylbutenoyloxy)ethylisocyanate, methacryloyloxymethylisocyanate, acryloyloxymethyl-isocyanate, (2-ethylbutenoyloxy)methylisocyanate, (2-propylbutenoyloxy)methylisocyanate, 3-methacryloyloxy-propylisocyanate, 3-acryloyloxypropylisocyanate, 3-(2-ethylbutenoyloxy)propylisocyanate, 3-(2-propylbutenoyloxy)-propylisocyanate, 4-methacryloyloxybutylisocyanate, 4-acryloyloxybutylisocyanate, 4-(2-ethylbutenoyloxy)-butylisocyanate, and 4-(2-propylbutenoyloxy)butylisocyanate.

(x) Curable Composition

The curable composition is prepared by incorporating other components in addition to the reactive (meth)acrylate polymer (A) according to the present invention. This curable composition can be used in applications such as resists (for example, solder resists, etching resists, color filter resists, and spacers), sealing (for example, waterproof sealing), paints (for example, antifouling paints, fluoropaints, and water-based paints), pressure-sensitive adhesives and adhesives (for example, adhesives and dicing tapes), printing plates (for example, CTP plates and offset plates), printing proofreading (for example, colorproof), lenses (for example, contact lenses, microlenses, and optical waveguides), dental materials, surface treatment (for example, optical fiber coating and disk coating), and battery materials (for example, solid electrolytes).

Specific examples of curable compositions suitable for color filters and curable compositions suitable for solder resists are as follows. The reactive (meth)acrylate polymer (A) which is particularly preferred for use in the curable composition is a urethane(meth)acrylate polymer prepared by reacting a polyhydroxy compound with an isocyanate compound of formula (I).

(x-a) Curable Composition Suitable for Color Filter

This curable composition contains a reactive (meth)acrylate polymer (A), a pigment (B), a photopolymerization initiator (D), an ethylenically unsaturated monomer (F), and an organic solvent (G).

(x-a-a) Reactive (meth)acrylate Polymer (A)

The content of the reactive (meth)acrylate polymer (A) in the curable composition is generally not less than 10% by mass, preferably not less than 20% by mass, more preferably 30 to 90% by mass. The mass ratio of reactive (meth)acrylate polymer (A)/other curable component such as ethylenically unsaturated monomer (F) is preferably 30/70 to 90/10, more preferably 40/60 to 85/15, from the viewpoints of balance between strength and photosensitivity. When the mass ratio of the reactive (meth)acrylate polymer (A) is smaller than 30/70, the film strength is lowered. On the other hand, when the mass ratio of the reactive (meth)acrylate polymer (A) is larger than 90/10, the cure shrinkage is increased.

(x-a-b) Pigment (B)

Red, green, and blue pigments may be used as the pigment (B). Black pigments may be mentioned as pigments which exhibits the maximum level of radiation shielding. Such black pigments may be conventional black pigments, and specific examples thereof include carbon black, acetylene black, lamp black, carbon nanotubes, graphite, iron black, iron oxide black pigments, aniline black, cyanine black, and titanium black. Black-based pigments prepared by mixing three organic pigments of red, green, and blue together may also be used.

Among them, carbon black and titanium black are preferred. Carbon black is particularly preferred from the viewpoints of light shielding and image properties.

The carbon black may be commercially available one, and the particle diameter of the carbon black is preferably 5 to 200 nm, more preferably 10 to 100 nm, from the viewpoints of dispersibility and resolution. When the particle diameter is less than 5 nm, homogeneous dispersion is difficult. On the other hand, when the particle diameter exceeds 200 nm, the resolution is lowered.

Specific examples of carbon blacks include Special Black 550, Special Black 350, Special Black 250, Special Black 100, Special Black 4 manufactured by Degussa, MA 100, MA 220, MA 230 manufactured by Mitsubishi Chemical Corporation, BLACKPEARLS 480 manufactured by Cabot Corporation, and RAVEN 410, RAVEN 420, RAVEN 450, and RAVEN 500 manufactured by Columbian Carbon.

(x-a-c) Photopolymerization Initiator (D)

The photopolymerization initiator (D) is a compound that, upon excitation by an actinic radiation, generates radicals which induce polymerization of the ethylenically unsaturated bond. Such photopolymerization initiators are required to generate radicals under high light shielding conditions. Therefore, high-sensitivity photopolymerization initiators are preferred. Specific examples of photopolymerization initiators include hexaarylbiimidazole compounds, triazine compounds, aminoacetophenone compounds, a combination of a sensitizing dye with an organic boron salt compound, titanocene compounds, and oxadiazole compounds.

Among them, hexaarylbiimidazole compounds, triazine compounds, aminoacetophenone compounds, glyoxy ester compounds, bisacylphosphine oxide compounds, and combinations thereof are preferred.

Specific examples of hexaarylbiimidazole compounds include 2,2'-bis(o-chlorophenyl)-4,4',5,5'-tetraphenyl-1,2'-biimidazole, 2,2'-bis(o-bromophenyl)-4,4',5,5'-tetraphenyl-1,2'-biimidazole, 2,2'-bis(o-chlorophenyl)-4,4',5,5'-tetra(o,p-dichlorophenyl)-1,2'-biimidazole, 2,2'-bis(o,p-dichlorophenyl)-4,4',5,5'-tetra(o,p-dichlorophenyl)-1,2'-biimidazole, 2,2'-bis(o-chlorophenyl)-4,4',5,5'-tetra(m-methoxyphenyl)-1,2'-biimidazole, and 2,2'-bis(o-methylphenyl)-4,4', 5,5'-tetraphenyl-1,2'-biimidazole.

In order to further enhance the sensitivity, for example, benzophenone compounds such as benzophenone, 2,4,6-trimethylbenzophenone, 4-phenylbenzophenone, 4,4'-bis(dimethylamino)benzophenone, and 4,4'-bis(diethylamino) benzophenone, and thioxanthone compounds such as 2,4-diethylthioxanthone, isopropylthioxanthone, 2,4-diisopropylthioxanthone, and 2-chlorothioxanthone may be added as sensitizers.

Specific examples of triazine compounds include 2,4,6-tris(trichloromethyl)-s-triazine, 2,4,6-tris(tribromomethyl)-s-triazine, 2-propionyl-4,6-bis(trichloromethyl)-s-triazine, 2-benzoyl-4,6-bis(trichloromethyl)-s-triazine, 2-(4-chlorophenyl)-4,6-bis(trichloromethyl)-s-triazine, 2,4-bis(4-methoxyphenyl)-6-trichloromethyl-s-triazine, 2-(4-methoxyphenyl)-2,6-bis(trichloromethyl)-s-triazine, 2-(4-methoxystyryl)-4,6-bis(trichloromethyl)-s-triazine, 2-(4-chlorostyryl)-4,6-bis(trichloromethyl)-s-triazine, 2-(4-aminophenyl)-4,6-bis(trichloromethyl)-s-triazine, 2,4-bis(3-chlorophenyl)-6-trichloromethyl-s-triazine, and 2-(4-aminostyryl)-4,6-bis(dichloromethyl)-s-triazine.

Specific examples of aminoacetophenone compounds include 2-methyl-1-[4-(methylthio)phenyl]-2-morpholinopropan-1-one, and 2-benzyl-2-dimethylamino-1-(4-morpholinophenyl)-butanone-1.

Specific examples of benzophenone compounds include benzophenone, 4-methylbenzophenone, 2,4,6-trimethylbenzophenone, benzoylbenzoic acid, 4-phenylbenzophenone, 3,3'-dimethyl-4-methoxybenzophenone, 4-benzoyl-4'-methyldiphenylsulfide, 4,4'-bis(dimethylamino)benzophenone, 4,4'-bis(diethylamino)benzophenone, (2-acryloyloxyethyl) (4-benzoylbenzyl)dimethylammoniumbromide, 4-(3-dimethylamino-2-hydroxypropoxy)-benzophenonemethochloride monohydrate, and (4-benzoylbenzyl) trimethylammoniumchloride.

Specific examples of thioxanthone compounds include thioxanthone, 2,4-diethylthioxanthone, isopropylthioxanthone, 2,4-diisopropylthioxanthone, 2-chlorothioxanthone, 1-chloro-4-propoxythioxanthone, and 2-(3-dimethylamimo-2-hydroxypropoxy)-3,4-dimethyl-9H-thioxanthen-9-one methochloride.

Specific examples of quinone compounds include 2-ethylanthraquinone and 9,10-phenanthrenequinone.

Specific examples of titanocene compounds include those described, for example, in Japanese Patent Laid-Open Nos. 152396/1984, 151197/1986, 10602/1988, 41484/1988, 291/1990, 12403/1991, 20293/1991, 27393/1991, 52050/1991, 221958/1992, and 21975/1992. Specific examples thereof include dicyclopentadienyl-Ti-dichloride, dicyclopentadienyl-Ti-diphenyl, dicyclopentadienyl-Ti-bis(2,3,4,5,6-pentafluorophenyl), dicyclopentadienyl-Ti-bis(2,3,5,6-tetrafluorophenyl), dicyclopentadienyl-Ti-bis(2,4,6-trifluorophenyl), dicyclopentadienyl-Ti-bis(2,6-difluorophenyl), dicyclopentadienyl-Ti-bis(2,4-difluorophenyl), bis(methylcyclopentadienyl)-Ti-bis(2,3,4,5,6-pentafluorophenyl), bis(methylcyclopentadienyl)-Ti-bis(2,3,5,6-tetrafluorophenyl), and bis(methylcyclopentadienyl)-Ti-bis(2,6-difluorophenyl)

Specific examples of oxadiazole compounds include halomethyl-containing 2-phenyl-5-trichloromethyl-1,3,4-oxadiazole, 2-(p-methylphenyl)-5-trichloromethyl-1,3,4-oxadiazole, 2-(p-methoxyphenyl)-5-trichloromethyl-1,3,4-oxadiazole, 2-styryl-5-trichloromethyl-1,3,4-oxadiazole, 2-(p-methoxystyryl)-5-trichloromethyl-1,3,4-oxadiazole, and 2-(p-butoxystyryl)-5-trichloromethyl-1,3,4-oxadiazole.

Specific examples of glyoxy ester compounds include benzyldimethylketal, benzomethyl ether, and benzoin isopropyl ether.

Specific examples of bisacylphosphirie oxide compounds include bis(2,6-dimethoxybenzoyl)-2,4,4-trimethylpentyl phosphineoxide, bis(2,6-dichlorobenzoyl)-phenylphosphineoxide, bis(2,6-dichlorobenzoyl)-2,5-dimethylphenylphosphineoxide, and bis(2,4,6-trimethylbenzoyl)phenylphosphineoxide.

(x-a-d) Ethylenically Unsaturated Monomer (F)

The ethylenically unsaturated monomer (F) is a compound that causes crosslinking by radicals generated from the photopolymerization initiator (D) upon exposure to an actinic radiation and functions, for example, to modify the viscosity of the composition. Specifically, (meth)acrylic esters are preferred.

Specific examples of (meth)acrylic esters include alkyl (meth)acrylates such as methyl(meth)acrylate, ethyl(meth)acrylate, propyl(meth)acrylate, butyl(meth)acrylate, isobutyl (meth)acrylate, sec-butyl(meth)acrylate, tert-butyl(meth)acrylate hexyl(meth)acrylate, octyl(meth)acrylate, isooctyl (meth)acrylate, 2-ethylhexyl(meth)acrylate, decyl(meth)acrylate, lauryl(meth)acrylate, and stearyl(meth)acrylate; alicyclic(meth)acrylates such as cyclohexyl(meth)acrylate, bornyl(meth)acrylate, isobornyl(meth)acrylate, dicyclopentenyl(meth)acrylate, and dicyclopentenyloxyethyl(meth)acrylate; aromatic(meth)acrylates such as benzyl(meth)acrylate, phenyl(meth)acrylate, phenylcarbitol(meth)acrylate, nonylphenyl(meth)acrylate, nonylphenylcarbitol(meth)acrylate, and nonylphenoxy(meth)acrylate; hydroxyl group-containing (meth)acrylates such as 2-hydroxyethyl(meth)acrylate, hydroxypropyl(meth)acrylate, hydroxybutyl(meth)acrylate, butanediol mono(meth)acrylate, glycerol (mete)acrylate, phenoxyhydroxypropyl(meth)acrylate, polyethylene glycol(meth)acrylate, and glycerol di(meth)acrylate; amino group-containing (meth)acrylates such as 2-dimethylaminoethyl(meth)acrylate, 2-diethylaminoethyl(meth)acrylate, and 2-tert-butylaminoethyl(meth)acrylate; phosphorus atom-containing methacrylates such as methacryloxyethyl phosphate, bis-methacryloxyethyl phosphate, and methacryloxyethylphenyl acid phosphate (phenyl-P); diacrylates such as ethylene grycol di(meth)acrylate, diethylene grycol di(meth)acrylate, triethylene grycol di(meth)acrylate, tetraethylene di(meth)acrylate, polyethylene glycol di(meth)acrylate, propylene glycol di(meth)acrylate, dipropylene glycol di(meth)acrylate, tripropylene glycol di(meth)acrylate, 1,4-butanediol di(meth)acrylate, 1,3-butanediol di(meth)acrylate, neopentyl glycol di(meth)acrylate, 1,6-hexanediol di(meth)acrylate, and bis-glycidyl(meth)acrylate; polyacrylates such as trimethylolpropane tri(meth)acrylate, pentaerythritol tri(meth)acrylate, and dipentaerythritol hexa(meth)acrylate; modified polyol polyacrylates such as ethylene oxide (4 mol)-modified diacrylate of bisphenol S, ethylene oxide (4 mol)-modified diacrylate of bisphenol A, fatty acid-modified pentaerythritol diacrylate, propylene oxide (3 mol)-modified triacrylate of trimethylolpropane, and propylene oxide (6 mol)-modified triacrylate of trimethylolpropane; polyacrylates having an isocyanuric acid skeleton, such as bis(acryloyloxyethyl)monohydroxyethyl isocyanurate, tris(acryloyloxyethyl)isocyanurate, and ε-caprolactone-modified tris(acryloyloxyethyl)isocyanurate; polyester acrylates such as α,ω-diacryloyl-(bisethylene glycol)-phthalate, or α,ω-tetraacryloyl-(bistrimethylolpropane)-tetrahydrophthalate; glycidyl(meth)acrylate; allyl(meth)acrylate; ω-hydroxyhexanoyloxyethyl(meth)acrylate; polycaprolactone (meth)acrylate; (meth)acryloyloxyethyl phthalate; (meth)acryloyloxyethyl succinate; 2-hydroxy-3-phenoxypropyl acrylate; and phenoxyethyl acrylate. Further, for example, N-vinyl compounds such as N-vinyl pyrrolidone, N-vinylformamide, or N-vinylacetamide, and polyester acrylate, urethane acrylate or epoxy acrylate may also be used as the ethylenically unsaturated monomer (F).

Among these compounds, hydroxyl-containing (meth)acrylate, glycidyl(meth)acrylate, and urethane acrylate are preferred. From the viewpoint of increased curability and heat resistance, the above compounds containing three or more ethylenically unsaturated groups are preferred.

(x-a-e) Organic Solvent (G)

Specific examples of the organic solvent (G) include ethers such as diisopropyl ether, ethyl isobutyl ether, and butyl ether; esters such as ethyl acetate, isopropyl acetate, butyl acetate (m, sec, tert), amyl acetate, 3-ethoxy ethyl propionate, 3-methoxy methyl propionate, 3-methoxy ethyl propionate, 3-methoxy propyl propionate, and 3-methoxy butyl propionate; ketones such as methyl ethyl ketone, isobutyl ketone, diisopropyl ketone, ethylamyl ketone, methyl butyl ketone, methyl hexyl ketone, methyl isoamyl ketone, methyl isobutyl ketone, and cyclohexanone; and glycols such as ethylene glycol monomethyl ether, ethylene glycol monoethyl ether, ethylene glycol diethyl ether, ethylene glycol monomethyl ether acetate, ethylene glycol monoethyl ether acetate, diethylene glycol monomethyl ether acetate, propylene glycol mono-t-butyl ether, propylene glycol monomethyl ether, propylene glycol monoethyl ether, propylene glycol monomethyl ether acetate, propylene glycol monoethyl ether acetate, dipropylene glycol monoethyl ether, dipropylene glycol monomethyl ether, dipropylene glycol monomethyl ether acetate, dipropylene glycol monoethyl ether acetate, ethylene glycol monobutyl ether, and tripropylene glycol methyl ether; and mixtures of the above compounds.

The organic solvent (G) can dissolve or disperse other components and has a boiling point of preferably 100 to 200° C., more preferably 120 to 170° C. The amount of the organic solvent (G) used is such that the solid content of the curable composition is brought to 5 to 50% by mass, preferably 10 to 30% by mass.

(x-a-f) Polyfunctional thiol (H)

The curable composition may contain a polyfunctional thiol (H). The polyfunctioinal thiol (H) is a compound containing two or more thiol groups, and specific examples thereof include hexanedithiol, decanedithiol, butanediol bisthiopropionate, butanediol bisthioglycolate, ethylene glycol bisthioglycolate, ethylene glycol bisthiopropionate, trimethylolpropane tristhioglycolate, trimethylolpropane tristhiopropionate, pentaerythritol tetrakisthioglycolate, pentaerythritol tetrakisthiopropionate, trimercaptopropionate tris(2-hydroxyethyl)isocyanurate, 1,4-dimethylmercaptobenzene, 2,4,6-trimercapto-s-triazine, and 2-(N,N-dibutylamino)-4,6-dimercapto-s-triazine.

(x-a-g) Content of Each Component

Preferably, in the curable composition, the components other than the organic solvent (G) have the following respective contents.

The content of the reactive (meth)acrylate polymer (A) is preferably 10 to 40% by mass, more preferably 15 to 35% by mass based on the total amount of the composition. When the content is less than 10% by mass, the film strength is sometimes lowered. On the other hand, when the content exceeds 40% by mass, in some cases, the optical density is unsatisfactory.

The content of the pigment (B) is preferably 25 to 60% by mass, more preferably 30 to 55% by mass, based on the total amount of the composition. When the content is less than 25% by mass, the optical density is sometimes unsatisfactory. On the other hand, when the content exceeds 60% by mass, in some cases, the film strength is lowered.

The content of the photopolymerization initiator (D) is preferably 2 to 25% by mass, more preferably 5 to 20% by mass, based on the total amount of the composition. When the content is less than 2% by mass, the photosensitivity is sometimes unsatisfactory. On the other hand, when the content exceeds 25% by mass, the photosensitivity is so high that the resolution is disadvantageously sometimes lowered.

The content of the ethylenically unsaturated monomer (F) is preferably 5 to 20% by mass, more preferably 8 to 18% by mass, based on the total amount of the composition. When the content is less than 5% by mass, the photosensitivity is sometimes unsatisfactory. On the other hand, when the content exceeds 20% by mass, in some cases, the optical density is unsatisfactory.

When the polyfuntional thiol (H) is added, the content of the photopolymerization initiator (D) is preferably 2 to 20% by mass, more preferably 3 to 15% by mass, based on the total amount of the composition. When the content is less than 2% by mass, the photosensitivity is sometimes unsatisfactory. On the other hand, when the content exceeds 20% by mass, in some cases, the photosensitivity is so high that the resolution is disadvantageously lowered. The content of the polyfunctional thiol (F) is preferably 2 to 20% by mass, more preferably 3 to 15% by mass, based on the total amount of the composition. When the content is less than 2% by mass, the effect of the polyfunctional thiol does not sometimes occur. On the other hand, when the content exceeds 20% by mass, in some cases, the photosensitivity is so high that the resolution is disadvantageously lowered.

In addition to the above components, for example, pigment dispersants, adhesion improvers, leveling agents, development improvers, antioxidants, and thermal polymerization inhibitors may be added to the curable composition. In particular, since what is important for quality stabilization is to finely disperse the coloring material and to stabilize the dispersion state, preferably, the pigment dispersant is incorporated according to need.

(x-a-h) Production Process of Curable Composition

The curable composition may be produced by mixing the components together by any proper method. The mixing may be carried by either a method in which the components are simultaneously mixed together or a method in which the components are successively mixed.

Mixing of all the formulating components together at a time followed by dispersion treatment leads to a fear of causing denaturation of highly reactive components due to heat generation during dispersion treatment. To avoid this unfavorable phenomenon, mixing is preferably carried out by a method in which the pigment (B) such as a black pigment, either together with the solvent (G) and the pigment dispersant, or together with a mixture of the solvent (G) and the pigment dispersant with the reactive (meth)acrylate polymer (A), is previously dispersed and the remaining components are then mixed.

The dispersion treatment may be carried out with a paint conditioner, a bead mill, a ball mill, a triple roll mill, a stone mill, a jet mill, a homogenizer or the like.

When the dispersion is carried out with a bead mill, glass beads or zirconia beads having a diameter of 0.1 to several millimeters are preferred. The dispersion is generally carried out at a temperature of 0 to 100° C., preferably room temperature to 80° C. A proper dispersion time is determined by taking into consideration, for example, the formulation of the colored composition (coloring materials, solvents, dispersant, and binder polymer), and apparatus size of the bead mill.

When the dispersion is carried out with a triple roll mill, the dispersion temperature is generally 0 to 60° C. When the frictional heat of the rolls is so large that the temperature exceeds 60° C., the inside of the roll is cooled with circulating water. The number of times of passage of the ink through the triple roll mill depends upon conditions such as linear velocity of rolls, pressure between rolls, and the viscosity of the materials and may be, for example, 2 to 10 times.

The composition prepared by the dispersion treatment is mixed with the remaining components by any proper method to produce the curable composition.

(x-a-i) Production Process of Color Filter

A color filter is produced by coating the curable composition onto a transparent substrate, drying the solvent in an oven or the like, then exposing and developing the dried coating to form a pattern, and then postbaking the patterned coating.

Specific examples of the transparent substrate include films or sheets of inorganic glasses such as quartz glass, borosilicate glass, and lime-soda glass with a silica-coated surface; thermoplastics, for example, polyesters such as polyethylene terephthalate, polyolefins such as polypropylene and polyethylene, polycarbonate, polymethyl methacrylate, and polysulfone; and thermosetting plastics such as epoxy polymers and polyester polymers. In order to improve properties such as surface adhesion, such transparent substrates may be previously subjected to corona discharge treatment, ozone treatment, and thin film treatment with silane coupling agents, urethane polymers or other various polymers.

The curable composition may be coated onto the transparent substrate with a coater such as a dip coater, a roll coater, a wire bar, a flow coater, a die coater, a spray coater, or a spin coater.

After coating, the coating may be dried by any proper method to remove the solvent. A drying device such as a hot plate, an IR oven, or a convection oven may be used for drying. The drying temperature is preferably 40 to 150° C., and the drying time is preferably 10 sec to 60 min. The solvent may be removed by drying in vacuum.

The exposure is carried out by placing a photomask on a sample and then exposing the dried coating image-wise through the photomask. Specific examples of light sources usable in the exposure include lamp light sources such as xenon lamps, high-pressure mercury lamps, ultrahigh-pressure mercury lamps, metal halide lamps, medium-pressure mercury lamps, and low-pressure mercury lamps, and laser beam sources such as argon ion lasers, YAG lasers, excimer lasers, and nitrogen lasers. When only irradiating light with a specific wavelength is used, an optical filter may be utilized.

The development treatment is carried out with a developing solution, and the resist is developed, for example, by a dipping, shower or paddle method. The developing solution may be a solvent that can dissolve the resist film in its unexposed areas, and specific examples thereof include organic solvents such as acetone, methylene chloride, trichlene, and cyclohexanone.

Further, an alkali developing solution may be used as the developing solution. Specific examples of such alkali developing solutions include aqueous solutions containing inorganic alkali chemicals such as sodium carbonate, potassium carbonate, sodium silicate, potassium silicate, sodium hydroxide, and potassium hydroxide, or organic alkali chemicals such as diethanolamine, triethanolamine, and tetraalkylammonium hydroxide. The alkali developing solution may if necessary contain, for example, surfactants, water soluble organic solvents, hydroxyl- or carboxyl-containing low-molecular compounds. In particular, a number of surfactants have the effect of improving developing properties, resolution, smudge and the like, and, thus, the addition of such surfactants is preferred.

Specific examples of surfactants usable for the developing solution include anionic surfactants containing sodium naphthalenesulfonate, sodium benzenesulfonate or other groups, nonionic surfactants containing polyalkyleneoxy groups, and cationic surfactants containing tetraalkylammonium groups.

The development treatment is generally carried out at a development temperature of 10 to 50° C., preferably 15 to 45° C., for example, by dip development, spray development, brush development, or ultrasonic development.

Postbaking is generally carried out with the same apparatus as drying for solvent removal at a temperature of 150 to 300° C. for 1 to 120 min. The film thickness of the matrix thus obtained is preferably 0.1 to 2 µm, more preferably 0.1 to 1.5 µm, still more preferably 0.1 to 1 µm. In order that the film functions as the matrix, the optical density in the above thickness range is preferably not less than 3.

In the black matrix pattern produced by the above method, in general, an opening having a size of about 20 to 200 µm is provided between patterns. In the post-process, pixels of R, G, and B are formed in this space. In general, the pixels are of three colors of R, G, and B and may be formed using a curable composition comprising a reactive (meth)acrylate polymer (A) and colored with the above pigment or dye in the same manner as in the formation of the black matrix.

(x-b) Curable Composition Suitable for Solder Resist

This curable composition comprises a reactive (meth)acrylate polymer (A), a thermosetting polymer (C), a photopolymerization initiator (D), an ethylenically unsaturated monomer (F), and a thermal polymerization catalyst (E).

(x-b-a) Heat-Curable Polymer (C)

The heat-curable polymer (C) is incorporated as a thermosetting component in the composition. The heat-curable polymer (C) per se may be cured by heating, or alternatively may be thermally reacted with the carboxyl group in the reactive (meth)acrylate polymer (A).

Specific examples of the heat-curable polymer (C) include epoxy polymers; phenol polymers; silicone polymers; melamine derivatives such as hexamethoxymelamine, hexabutoxymelamine, and condensed hexamethoxymelamine; urea compounds such as dimethylolurea; bisphenol A compounds such as tetramthylol-bisphenol A; oxazoline compounds; and oxetane compounds. They may be used either alone or in a combination of two or more of them.

Among them, epoxy polymers are preferred. Specific examples of epoxy polymers include epoxy compounds containing two or more epoxy groups per molecule such as bisphenol A epoxy polymers, hydrogenated bisphenol A epoxy polymers, brominated bisphenol A epoxy polymers, bisphenol F epoxy polymers, novolak epoxy polymers, phenol novolak epoxy polymers, cresol novolak epoxy polymers, N-glycidyl epoxy polymers, bisphenol A novolak epoxy polymers, chelate epoxy polymers, glyoxal epoxy polymers, amino-containing epoxy polymers, rubber-modified epoxy polymers, dicyclopentadiene phenolic epoxy polymers, silicone-modified epoxy polymers, and ε-caprolactone-modified epoxy polymers; and bisphenol S epoxy polymers, diglycidyl phthalate polymers, heterocyclic epoxy polymers, bixylenol epoxy polymers, biphenyl epoxy polymers, and tetraglycidylxylenoylethane polymers.

In order to impart flame retardancy, use may be made of epoxy polymers in which a halogen such as chlorine or bromine, phosphorus or other atom has been introduced into the structure in such a bound state that is less likely to be decomposed by heat or water. These epoxy polymers may be used either solely or in a combination of two or more of them.

The content of the heat-curable polymer (C) is preferably 10 to 150 parts by mass, more preferably 10 to 50 parts by mass, based on 100 parts by mass in total of the photocurable components. When the content of the heat-curable polymer (C) is less than 10 parts by mass, soldering heat resistance of the cured film is sometimes unsatisfactory. On the other hand, when the content of the heat-curable polymer (C) exceeds 150 parts by mass, the shrinkage of the cured film is increased. In this case, when the cured film is used in an insulating protective film in an FPC substrate, the warpage is likely to be increased.

(x-b-b) Photopolymerization Initiator (D)

The same photopolymerization initiators as used in the curable composition suitable for color filters may be used as the photopolymerization initiator (D)

The content of the photopolymerization initiator (D) is preferably 0.1 to 20 parts by mass, more preferably 0.2 to 10 parts by mass, based on 100 parts by mass in total of the urethane(meth)acrylate polymer (A), the ethylenically unsaturated monomer (F), and the carboxyl-containing epoxy (meth)acrylate compound which is optionally incorporated. When the content of the photopolymerization initiator (D) is less than 0.1 part by mass, in some cases, the curing of the composition is unsatisfactory.

(x-b-c) Thermal Polymerization Catalyst (E)

The thermal polymerization catalyst (E) functions to thermally cure the heat-curable polymer (C), and specific examples thereof include amines; amine salts or quaternary ammonium salts such as chlorides of the amines; acid anhydrides such as cyclic aliphatic acid anhydrides, aliphatic acid anhydrides, and aromatic acid anhydrides; nitrogen-containing heterocyclic compounds such as polyamides, imidazoles, and triazine compounds; and organometal compounds. They may be used either solely or in a combination of two or more of them.

Specific examples of amines include aliphatic or aromatic primary, secondary, and tertiary amines.

Specific examples of aliphatic amines include polymethylenediamine, polyetherdiamine, diethylenetriamine, triethylenetriamine, tetraethylenepentamine, triethylenetetramine, dimethylaminopropylamine, menthenediamine, aminoethylethanolamine, bis(hexamethylene)triamine, 1,3,6-trisaminomethylhexane, tributylamine, 1,4-diazabicyclo[2,2,2]octane, and 1,8-diazabicyclo[5,4,0]undecen-7-ene.

Specific examples of aromatic amines include metaphenylenediamine, diaminodiphenylmethane, and diaminodiphenylsulfone.

Specific examples of acid anhydrides include aromatic acid anhydrides such as phthalic anhydride, trimellitic anhydride, benzophenone tetracarboxylic acid anhydride, ethylene glycol bis(anhydro trimellitate), and glycerol tris(anhydro trimellitate), and maleic anhydride, succinic acid anhydride, methylnadic anhydride, hexahydrophthalic anhydride, tetrahydrophthalic anhydride, polyadipic acid anhydride, chlorendic anhydride, and tetrabromophthalic anhydride.

Specific examples of polyamides include primary amino- or secondary amino-containing polyaminoamides produced by condensing a dimeric acid with a polyamine such as diethylenetriamine or triethylenetetramine.

Specific examples of imidazoles include imidazole, 2-ethyl-4-methylimidazole, N-benzyl-2-methylimidazole, 1-cyanoethyl-2-undecylimidazolium-trimellitate, and 2-methylimidazolium-isocyamurate.

The triazine compound is a compound with a six-membered ring containing three nitrogen atoms, and specific examples thereof include melamine compounds such as melamine, N-ethylenemelamine, and N,N',N''-triphenylmelamine; cyanuric acid compounds such as cyanuric acid, isocyanuric acid, trimethyl cyanurate, isocyanurate, triethyl cyanurate, trisethyl isocyanurate, tri(n-propyl)cyanurate, tris(n-propyl)isocyanurate, diethyl cyanurate, N,N'-diethyl isocyanurate, methyl cyanurate, and methyl isocyanurate; and cyanuric acid melamine compounds such as a reaction product between equimolar amounts of a melamine compound and a cyanuric acid compound.

Specific examples of organometallic compounds include metal salts of organic acids such as dibutyltin-dilaurate, dibutyltin maleate, and zinc 2-ethylhexanoate; 1,3-diketone metal complex salts such as nickel acetyl acetonate, zinc acetylacetonate; and metal alkoxides such as titanium tetrabutoxide, zirconium tetrabutoxide, and aluminum butoxide.

The amount of the thermal polymerization catalyst (E) used is preferably 0.5 to 20 parts by mass, more preferably 1 to 10 parts by mass, based on 100 parts by mass of the heat-curable polymer (C). When the amount of the thermal polymerization catalyst (E) used is less than 0.5 part by mass, the curing reaction does not proceed satisfactorily. In this case, in some cases, the heat resistance is deteriorated. Further, curing at an elevated temperature for a long period of time is necessary, and this is sometimes causative of lowered working efficiency. On the other hand, when the amount of the thermal polymerization catalyst (E) used exceeds 20 parts by mass, the thermal polymerization catalyst (E) is likely to react with the carboxyl group in the composition to cause gelation, often leading to a problem of deteriorated storage stability.

(x-b-d) Ethylenically Unsaturated Monomer (F)

The same ethylenically unsaturated monomer as used in the curable composition suitable for color filters may be used as the ethylenically unsaturated monomer (F).

The mixing ratio of the reactive (meth)acrylate polymer (A) to other ethylenically unsaturated monomer (F) is preferably 95:5 to 50:50, more preferably 90:10 to 60 to 40, still more preferably 85:15 to 70:30, in terms of mass ratio. When the mixing ratio of the reactive (meth)acrylate polymer (A) exceeds 95, the heat resistance of the cured film formed of the composition is sometimes deteriorated. On the other hand, when the mixing ratio of the reactive (meth)acrylate polymer (A) is less than 5, the solubility of the composition in alkali is likely to be lowered.

If necessary, carboxyl-containing epoxy(meth)acrylate compounds may be used as the curable component. Such carboxyl-containing epoxy(meth)acrylate compounds include, for example, those described in the above (iv-f). The acid value of these carboxyl-containing epoxy(meth)acrylate compounds is preferably not less than 10 mgKOH/g, more preferably 45 to 160 mgKOH/g, still more preferably 50 to 140 mgKOH/g. The use of the epoxy(meth)acrylate compounds having the above acid value can improve balance between the alkali solubility of the composition and the alkali resistance of the cured film. When the acid value is less than 10 mgKOH/g, the alkali solubility is deteriorated. On the other hand, when the acid value is excessively large, in some cases, for some formulation of the composition, the alkali resistance of the cured film and properties as a resist such as electrical characteristics are deteriorated. When the carboxyl-containing epoxy(meth)acrylate compound is used, preferably, this compound is used in an amount of not more than 100 parts by mass based on 100 parts by mass of the carboxyl-containing reactive (meth)acrylate polymer (A).

(x-b-e) Production Process of Curable Composition

As with the curable composition suitable for color filters, the above curable composition may be produced by mixing the above-described components together by a conventional method. The mixing method is not particularly limited, and examples thereof include a method in which a part of the components is mixed and the remaining components are then mixed and a method in which all the components are mixed at a time.

An organic solvent may be if necessary added to the composition for viscosity modification purposes or the like. The viscosity modification facilitates coating or printing onto an object, for example, by roller coating, spin coating, screen coating, or curtain coating. Organic solvents usable herein include ketone solvents such as ethyl methyl ketone, methyl isobutyl ketone, and cyclohexanone; ester solvents such as ethyl acetoacetate, γ-butyrolactone, and butyl acetate; alcohol solvents such as butanol and benzyl alcohol; cellosolve solvents and carbitol solvents such as carbitol acetate and methylcellosolve acetate, and their ester and ether derivative solvents; amide solvents such as N,N-dimethylformamide, N,N-dimethylacetamide, N,N-dimethylformamide, and N-methyl-2-pyrrolidone; dimethyl sulfoxide; phenol solvents such as phenol and cresol; nitro compound solvents; and aromatic or alicyclic solvents of hydrocarbons such as toluene, xylene, hexamethylbenzene, cumene aromatic solvents, tetralin, decalin and dipentene. They may be used either solely or in a combination of two or more of them.

The amount of the organic solvent used is preferably such that the viscosity of the composition is 500 to 500,000 mPa·s, more preferably 1,000 to 500,000 mPa·s (as measured at 25° C. with Brookfield viscometer). When the viscosity of the composition is in the above-defined range, the composition is more suitable and easier to use for coating or printing on an object. The amount of the organic solvent used for bringing the viscosity to fall within the above-defined range is preferably not more than 1.5 times by mass the amount of the solid matter other than the organic solvent. When the amount of the organic solvent exceeds 1.5 times by mass, the solid content is lowered. In this case, when the composition is printed on a substrate or the like, a satisfactory film thickness cannot be provided by single printing and, thus, in some cases, printing should be carried out a plurality of times.

Further, a colorant may be added to the composition for use of the composition as ink. Specific examples of colorants usable herein include phthalocyanine blue, phthalocyanine green, iodine green, disazo yellow, crystal violet, titanium oxide, carbon black, and naphthalene black. Also when the composition is used as ink, the viscosity is preferably 500 to 500,000 mPa·s.

A flow modifier may be further added to the composition for flow modification purposes. The addition of the flow modifier can realize proper modification of the fluidity of the composition, for example, in the case where the composition is coated onto an object by roller coating, spin coating, screen coating, curtain coating or the like.

Specific examples of flow modifiers include inorganic or organic fillers, waxes, and surfactants. Specific examples of inorganic fillers include talc, barium sulfate, barium titanate, silica, alumina, clay, magnesium carbonate, calcium carbonate, aluminum hydroxide, and silicate compounds. Specific examples of organic fillers include silicone resins, silicone rubbers, and fluororesins. Specific examples of waxes include polyamide wax and polyethylene oxide wax. Specific examples of surfactants include silicone oils, higher fatty acid esters, and anides. These flow modifiers may be used either solely or in a combination of two or more.

If necessary, additives such as thermal polymerization inhibitors, thickeners, defoamers, leveling agents, and tackifiers can be added to the composition. Specific examples of thermal polymerization inhibitors include hydroquinone, hydroquinone monomethyl ether, tert-butyl catechol, pyrogallol, and phenothiazine. Specific examples of thickeners include asbestos, orben, bentone, and montmorillonite. The antifoamer is used to remove foam formed during printing, coating or curing, and specific examples thereof include surfactants such as acrylic and silicone surfactants. The leveling agent is used to render a film surface with concaves and convexes formed by printing or coating even, and specific examples thereof include surfactants such as acrylic and silicone surfactants. Specific examples of tackifiers include imidazole, thiazole, and triazole tackifiers and silane coupling agents.

Other additives usable herein include, for example, ultraviolet absorbers and plasticizers for storage stabilization purposes.

A coating film may be formed by coating the above curable composition onto a substrate or the like by screen printing to a suitable thickness and heat drying the coating. Thereafter, the coating film can be brought to a cured product by exposing and developing the coating film and heat curing the developed coating film.

The above curable composition can be used in various applications. In particular, the curable composition is excellent in photosensitivity and developing properties. Further, the curable composition can be cured to form a thin film which is also excellent in adhesion to substrate, insulating properties, heat resistance, warpage deformation, flexibility and appearance and thus is suitable for use as an insulating protective film in printed wiring boards. The insulating protective film may be formed by coating the composition or ink onto a substrate with a circuit formed thereon to a thickness of 10 to 100 μm and then heat treating the coating at a temperature of 60 to 100° C. for about 5 to 30 min to dry the coating and thus to bring the thickness to 5 to 70 μm. Next, the dried coating is exposed through a negative mask having a desired exposure pattern and is then developed with a developing solution to remove unexposed areas, followed by heat curing at a temperature of 100 to 180° C. for about 10 to 40 min.

This curable composition can be cured to form a cured product which is excellent particularly in flexibility. By virtue of excellent flexibility, the cured product is particularly suitable for use as an insulating protective film in an FPC substrate and can provide an FPC substrate which is less likely to curl and has good handleability. Further, the cured product may also be used as an insulating resin layer between layers, for example, in a multilayer printed wiring board.

Actinic light generated, for example, from conventional actinic light sources, for example, carbon arc, mercury vapor arc, and xenon arc may be used as an actinic light source used in the exposure.

Developing solutions usable herein include aqueous solutions of alkalis such as potassium hydroxide, sodium hydroxide, sodium carbonate, potassium carbonate, sodium phosphate, sodium silicate, ammonia, and amines.

Further, the curable composition may be used in a photosensitive layer in a dry film resist. The dry film resist comprises a photosensitive layer formed of the composition on a support formed of a polymer film or the like. The thickness of the photosensitive layer is preferably 10 to 70 μm. Specific examples of polymer films suitable as the support include films of polyester resins such as polyethylene terephthalate and aliphatic polyesters and polyolefin resins such as polypropylene and low-density polyethylene.

The dry film resist may be formed by coating the curable composition onto a support and then drying the coating to form a photosensitive layer. Further, a dry film resist, which comprises a support, a photosensitive layer, and a cover film stacked on top of one another, that is, which has films provided respectively on both sides of the photosensitive layer, may be formed by providing a cover film on the formed photosensitive layer. In use of the dry film resist, the cover film is peeled off. Until use of the dry film resist, the cover film provided on the photosensitive layer can protect the photosensitive layer, that is, the dry film resist has an excellent pot life.

In the formation of an insulating protective film on a printed wiring board using the dry film resist, the dry film resist is first laminated onto a substrate so that the photosensitive layer faces the substrate. Here when the dry film resist provided with the cover film is used, the cover film is removed to expose the photosensitive layer before contact with the substrate.

Next, the photosensitive layer and the substrate are thermocompression bonded to each other through a pressure roller or the like at about 40 to 120° C. to stack the photosensitive layer onto the substrate. Thereafter, the photosensitive layer is exposed through a negative mask having a desired exposure pattern, and the support is removed from the photosensitive layer. Development is carried out with a developing solution to remove the unexposed areas, and the photosensitive layer is then heat cured to prepare a printed wiring board comprising an insulating protective film provided on the surface of the substrate. Further, the above dry film resist may be used to form an insulating resin layer between layers in a multilayer printed wiring board.

EXAMPLES

The following Examples further illustrate the present invention. However, it should be noted that the present invention is not limited to these Examples only.

Analytical instruments and analytical conditions used in Examples 1 to 6 were as follows.

Gas Chromatography (GC)

Analytical instrument: GC 14A, manufactured by Shimadzu Seisakusho Ltd.

Column: DB-1, manufactured by J & W, 30 m×0.53 mm×1.5 μm

Column temperature: 70° C., temperature rise at 10° C./min to 250° C., holding for 18 min Integrator: CR7A, manufactured by Shimadzu Seisakusho Ltd.

Injection temperature: 220° C.

Detector temperature: 270° C. FID

Detector: FID, $H_2$ 40 ml/min, Air 400 ml/min

Carrier gas: He 10 ml/min

Automatic Titrator

Analytical equipment: COM-550, manufactured by HIRANUMA SANGYO Co., Ltd.

Example 1

First Step

2-Amino-1,3-propanediol (20.0 g, 0.22 mol) and 200 ml of toluene were charged into a 500-ml four-necked flask equipped with a stirrer, a thermometer, a dropping funnel, and a reflux condenser under a nitrogen atmosphere. The contents of the flask were heated to 50° C., and 2-amino-1,3-propanediol was dissolved, and hydrogen chloride gas was fed into the flask at a flow rate of 100 ml/min over a period of one hr.

Second Step

The solution prepared in the first step was heated to 90° C. 3-Chloropropionic acid chloride (62.6 g, 0.49 mol) was fed to the solution over a period of 1.5 hr, and heating was continued at 90° C. for additional one hr.

Third Step

Carbonyl chloride (47.5 g, 0.48 mol) was fed to the solution prepared in the second step over a period of 4 hr while maintaining the temperature of the solution at 90° C., and heating was continued at 90° C. for additional one hr. Thereafter, carbonyl chloride remaining dissolved in the reaction solution was removed by introducing nitrogen. The solution was then analyzed by gas chromatography. As a result, it was found that 1,3-bis-3-chloropropionyloxypropane-2-isocyanate was obtained (59.0 g, 0.20 mol, yield 90%).

Fourth Step

The solution obtained in the third step was analyzed for alkali decomposable chlorine by the following method. About 0.5 g of a sample was accurately weighed into a 300-ml stoppered conical flask, and 100 ml of a mixed liquid composed of methanol and purified water at 70:30 volume ratio was added to the sample. Next, 10 ml of a 30% aqueous sodium hydroxide solution was added thereto. A cooling pipe was attached to the flask, and the contents of the flask were heated on a water bath of 80° C. under reflux for one hr. After cooling, the solution in the flask was transferred to a 200-ml measuring flask and was measured up with purified water. Next, 10 ml of the solution was accurately placed in a 200-ml beaker, 100 ml of purified water was added, 1 ml of (1+1) nitric acid was added thereto, and potentiometric titration was carried out with a 1/50 N silver nitrate solution.

As a result, it was found that the concentration of the alkali decomposable chlorine in the solution obtained in the third step was 8.7% and 220 g of the solution contained 19.1 g (0.54 mol) of alkali decomposable chlorine. This solution was charged into a 500-ml flask, and 0.05 g of phenothiazine and 0.05 g of 2,6-bis-t-butylhydroxy toluene were added to the solution. Thereafter, 57.6 g (0.52 mol) of triethylamine was added dropwise thereto over a period of one hr. When the dropwise addition was initiated, the temperature of the solution was 25° C. The dropwise addition caused heat generation of the solution, resulting in a temperature rise to 60° C. The solution was stirred with heating at 60° C. for 4 hr and was then cooled to room temperature. The resultant solid matter was collected by filtration and was washed with toluene. The weight of the filtrate thus obtained was 230 g. The filtrate was analyzed by gas chromatography. As a result, it was found that 1,3-bisacryloyloxypropane-2-isocyanate was obtained (36.8 g, 0.16 mol, yield 73%).

Purification Step

To the filtrate were added 0.05 g of phenothiazine and 0.05 g of 2,6-bis-t-butylhydroxy toluene. The pressure was reduced by a vacuum pump to 10 kPa, and the solvent was removed by evaporation. The resultant concentrate was charged into a 100-ml flask, and 0.05 g of phenothiazine and 0.05 g of 2,6-bis-t-butylhydroxy toluene were added thereto. The pressure was reduced to 0.5 kPa, followed by distillation to collect a distillate of 120 to 123° C. As a result, it was found that 1,3-acryloyloxypropane-2-isocyanate was obtained (30.2 g, 0.13 mol, yield 61%).

Example 2

First Step

2-Amino-2-methyl-1,3-propanediol (20.0 g, 0.19 mol) and 200 ml of toluene were charged into a 500-ml four-necked flask equipped with a stirrer, a thermometer, a dropping funnel, and a reflux condenser under a nitrogen atmosphere. Hydrogen chloride gas was fed into the flask at a flow rate of 100 ml/min over a period of one hr.

Second Step

The solution prepared in the first step was heated to 95° C. 3-Chloropropionic acid chloride (54.3 g, 0.43 mol) was fed to the solution over a period of one hr, and heating was continued at 95° C. for additional one hr.

Third Step

Carbonyl chloride (43.0 g, 0.43 mol) was fed to the solution prepared in the second step over a period of 4 hr while maintaining the temperature of the solution at 90° C., and heating was continued at 90° C. for additional one hr. Thereafter, carbonyl chloride remaining dissolved in the reaction solution was removed by introducing nitrogen.

Fourth Step

The concentration of the alkali decomposable chlorine in the solution obtained in the third step was 7.9%, and 200 g of the solution contained 15.8 g (0.45 mol) of alkali decomposable chlorine. This solution was charged into a 500-ml flask, and 0.05 g of phenothiazine and 0.05 g of 2,6-bis-t-butylhydroxy toluene were added as a polymerization inhibitor to the solution. Thereafter, 45.0 g (0.45 mol) of triethylamine was added dropwise thereto over a period of one hr. When the dropwise addition was initiated, the temperature of the solution was 25° C. The dropwise addition caused heat generation of the solution, resulting in a temperature rise to 60° C. The reaction solution was heated to 70° C., and stirring was continued at that temperature for 5 hr, followed by cooling to room temperature. The solid matter thus obtained was collected by filtration and was washed with toluene to give 200 g of the filtrate. The filtrate was analyzed by gas chromatography. As a result, it was found that 1,3-bisacryloyloxy-2-methyl-propane-2-isocyanate was obtained (32.2 g, 0.13 mol, yield 71%).

Purification Step

To the filtrate were added 0.05 g of phenothiazine and 0.05 g of 2,6-bis-t-butylhydroxy toluene. The pressure was reduced by a vacuum pump to 0.7 kPa, and the solvent was removed by evaporation. The pressure was then reduced to 0.3 kPa, followed by distillation to collect a distillate of 105 to 110° C. As a result, it was found that 1,3-bisacryloyloxy-2-methyl-propane-2-isocyanate was obtained (26.2 g, 0.11 mol, yield 58%).

Example 3

First Step

2-Amino-2-methyl-1,3-propanediol (20.0 g, 0.19 mol) and 40 ml of methanol were charged into a 200-ml four-necked flask equipped with a stirrer, a thermometer, and a reflux condenser under a nitrogen atmosphere. Hydrogen chloride gas was fed into the flask at a flow rate of 100 ml/min over a period of one hr. Methanol was removed by evaporation under reduced pressure to give a white crystal of 2-amino-2-methyl-1,3-propanediol hydrochloride (27.0 g, 0.19 mol).

Second Step

2-Amino-2-methyl-1,3-propanediol hydrochloride (27.0 g) prepared above and 200 ml of toluene were charged into a 200-ml four-necked flask equipped with a stirrer, a thermometer, a dropping funnel, and a reflux condenser under a nitrogen atmosphere. The contents of the flask were heated to 95° C. 3-Chloropropionic acid chloride (54.3 g, 0.43 mol) was fed to the solution over a period of one hr, and heating was then continued at 95° C. for additional one hr.

Third Step

Carbonyl chloride (43.0 g, 0.43 mol) was fed to the solution prepared in the second step over a period of 4 hr while maintaining the temperature of the solution at 90° C. and heating was continued at 90° C. for one hr. Thereafter, carbonyl chloride remaining dissolved in the reaction solution was removed by introducing nitrogen. The solution was then analyzed by gas chromatography. As a result, it was found that 1,3-bis-3-chloropropionyloxy-2-methylpropane-2-isocyanate was obtained (52.2 g, 0.17 mol, yield 88%).

Fourth Step

The solution obtained in the third step was analyzed for alkali decomposable chlorine. As a result, it was found that the concentration of the alkali decomposable chlorine in the solution obtained in the third step was 7.9% and 200 g of the solution contained 15.8 g (0.45 mol) of alkali decomposable chlorine. This solution was charged into a 500-ml flask, and 0.05 g of phenothiazine and 0.05 g of 2,6-bis-t-butylhydroxy toluene were added to the solution. Thereafter, 45.0 g (0.45 mmol) of triethylamine was added thereto over a period of one hr. When the dropwise addition was initiated, the temperature of the solution was 25° C. The dropwise addition caused heat generation of the solution, resulting in a temperature rise to 60° C. Stirring of the solution was continued with heating at 60° C. for 5 hr and was then cooled to room temperature. The resultant solid matter was collected by filtration and was washed with toluene. The weight of the filtrate thus obtained was 200 g. The filtrate was analyzed by gas chromatography. As a result, it was found that 1,3-bisacryloyloxy-2-methylpropane-2-isocyanate was obtained (33.5 g, 0.14 mol, yield 74%).

Purification Step

To the filtrate were added 0.05 g of phenothiazine and 0.05 g of 2,6-bis-t-butylhydroxy toluene. The pressure was reduced by a vacuum pump to 0.7 kPa, and the solvent was removed by evaporation. Subsequently, the pressure was reduced to 0.3 kPa, followed by distillation to collect a distillate of 105 to 110° C. As a result, it was found that 1,3-bisacryloyloxy-2-methylpropane-2-isocyanate was obtained (25.8 g, 0.11 mol, yield 57%).

Example 4

First Step

2-Amino-2-methyl-1,3-propanediol (30.0 g, 0.29 mol) and 300 ml of dioxane were charged into a 500-ml four-necked flask equipped with a stirrer, a thermometer, a dropping funnel, and a reflux condenser under a nitrogen atmosphere. Hydrogen chloride gas was fed into the flask at a flow rate of 100 ml/min over a period of one hr.

Second Step

The solution prepared in the first step was heated to 95° C. 3-Chloropropionic acid chloride (90.5 g, 0.71 mol) was fed to the solution over a period of one hr, and heating was then continued at 95° C. for additional one hr.

Third Step

Carbonyl chloride (82.5 g, 0.83 mol) was fed to the solution prepared in the second step over a period of 6 hr while maintaining the temperature of the solution at 90° C., and heating was continued at 90° C. for additional one hr. Thereafter, carbonyl chloride remaining dissolved in the reaction solution was removed by introducing nitrogen. The solution was then analyzed by gas chromatography. As a result, it was found that 1,3-bis-3-chloropropionyloxy-2-methylpropane-2-isocyanate was obtained (53.6 g, 0.17 mol, yield 90%).

Fourth Step

The solution obtained in the third step was analyzed for alkali decomposable chlorine. As a result, it was found that the concentration of the alkali decomposable chlorine in the solution obtained in the third step was 8.1% and 353.5 g of the solution contained 28.6 g (0.81 mol) of alkali decomposable chlorine. This solution was charged into a 500-ml flask, and 0.20 g of phenothiazine and 0.20 g of 2,6-bis-t-butylhydroxy toluene were added to the solution. Thereafter, 80.0 g (0.79 mol) of triethylamine was added dropwise thereto over a period of 1.5 hr. After the completion of the dropwise addition, stirring with heating was continued at 50° C. for 5 hr and was then cooled to room temperature. The resultant solid matter was collected by filtration and was washed with toluene. The weight of the filtrate thus obtained was 383.5 g. The filtrate was analyzed by gas chromatography. As a result, it was found that 1,3-bisacryloyloxy-2-methylpropane-2-isocyanate was obtained (35.6 g, 0.15 mol, yield 78%).

Purification Step

To the filtrate were added 0.20 g of phenothiazine and 0.20 g of 2,6-bis-t-butylhydroxy toluene. The pressure was reduced by a vacuum pump to 0.7 kPa, and the solvent was removed by evaporation. Subsequently, the pressure was reduced to 0.3 kPa, followed by distillation to collect a distillate of 105 to 110° C. As a result, it was found that 1,3-bisacryloyloxy-2-methylpropane-2-isocyanate was obtained (26.2 g, 0.11 mol, yield 58%).

Example 5

First Step

1-Amino-2,3-propanediol (20.0 g, 0.22 mol) and 200 ml of toluene were charged into a 500-ml four-necked flask equipped with a stirrer, a thermometer, a dropping funnel, and a reflux condenser under a nitrogen atmosphere. Hydrogen chloride gas was fed into the flask at a flow rate of 100 ml/min over a period of one hr.

Second Step

The solution prepared in the first step was heated to 95° C. 3-Chloropropionic acid chloride (70.4 g, 0.55 mol) was fed to the solution over a period of 1.5 hr, and heating was then continued at 95° C. for additional 3 hr.

Third Step

Carbonyl chloride (50.8 g, 0.51 mol) was fed to the solution prepared in the second step over a period of 4.5 hr while maintaining the temperature of the solution at 90° C., and heating was continued at 90° C. for additional one hr. Thereafter, carbonyl chloride remaining dissolved in the reaction solution was removed by introducing nitrogen. The solution was then analyzed by gas chromatography. As a result, it was found that 1,2-bis-3-chloropropionyloxypropane-1-isocyanate was obtained (52.2 g, 0.18 mol, yield 80%).

Fourth Step

The alkali decomposition concentration of the solution obtained in the third step was 9.2% and 216 g of the solution contained 19.9 g (0.56 mol) of alkali decomposable chlorine. This solution was charged into a 500-ml flask, and 0.05 g of phenothiazine as a polymerization inhibitor and 0.05 g of 2,6-bis-t-butylhydroxy toluene were added to the solution. Thereafter, 55.6 g (0.55 mol) of triethylamine was added dropwise thereto over a period of 1 hr. When the dropwise addition was initiated, the temperature of the solution was 25° C. The dropwise addition caused heat generation of the solution, resulting in a temperature rise to 60° C. The solution was heated to 70° C., and stirring with heating was continued for 5 hr and was then cooled to room temperature. The resultant solid matter was collected by filtration and was washed with toluene. The weight of the filtrate thus obtained was 220 g. The filtrate was analyzed by gas chromatography. As a result, it was found that 1,2-bisacryloyloxypropane-1-isocyanate was obtained (30.2 g, 0.13 mol, yield 61%).

Purification Step

To the filtrate were added 0.05 g of phenothiazine and 0.05 g of 2,6-bis-t-butylhydroxy toluene. The pressure was reduced by a vacuum pump to 0.7 kPa, and the solvent was removed by evaporation. Subsequently, the pressure was reduced to 0.5 kPa, followed by distillation to collect a distillate of 114 to 122° C. As a result, it was found that 1,2-bisacryloyloxypropane-1-isocyanate was obtained (25.4 g, 0.11 mol, yield 50%).

Example 6

First Step

2-Amino-1,3-propanediol (20.0 g, 0.22 mol) and 200 ml of toluene were charged into a 500-ml four-necked flask equipped with a stirrer, a thermometer, a dropping funnel, and a reflux condenser under a nitrogen atmosphere. Hydrogen chloride gas was fed into the flask at a flow rate of 100 ml/min over a period of one hr.

Second Step

The solution prepared in the first step was heated to 90° C. Methacrylic acid chloride (49.2 g, 0.47 mol) was fed to the solution over a period of 1.5 hr, and heating was continued at 90° C. for additional 2 hr.

Third Step

Carbonyl chloride (61.1 g, 0.62 mol) was fed to the solution prepared in the second step over a period of 4 hr while maintaining the temperature of the solution at 90° C., and heating was continued at 90° C. for additional one hr. Thereafter, carbonyl chloride remaining dissolved in the reaction solution was removed by introducing nitrogen. The solution was then analyzed by gas chromatography. As a result, it was found that 1,3-bis-methacryloyloxypropane-2-isocyanate was obtained (38.1 g, 0.15 mol, yield 68%).

Purification Step

To the solution prepared in the third step were added 0.05 g of phenothiazine and 0.05 g of 2,6-bis-t-butylhydroxy toluene. The pressure was reduced by a vacuum pump to 0.7 kPa, and the solvent was removed by evaporation. Subsequently, the pressure was reduced to 0.3 kPa, followed by distillation to collect a distillate of 133 to 140° C. As a result, it was found that 1,3-bismethacryloyloxypropane-2-isocyanate was obtained (29.0 g, 0.11 mol, yield 52%).

Examples 7 to 22 and Comparative Examples 1 to 13

(1) Preparation of Curable Compositions and Preparation of Evaluation Samples

1-Hydroxy-cyclohexyl-phenyl-ketone (Irgacure 184 manufactured by Ciba Specialty Chemicals, K.K.) as a photopolymerization initiator for the reactive monomer (as described in Table 1 to Table 9) was mixed in the mixing amount as described in Tables 1 to 9 into 20 g of dichloromethane (manufactured by Junsei Chemical Corporation) with stirring at room temperature to give homogeneous curable composition solutions. Further, these curable composition solutions were coated onto a glass substrate (size 50 mm×50 mm) to a film thickness of about 200 Mm on a dry basis, the coated glass substrate was dried at 50° C. for 30 min to prepare evaluation samples of Examples 7 to 22, Comparative Examples 1 to 7 and Comparative Examples 9 to 13.

(2) Evaluation of Curable Composition

<Curability>

The evaluation samples of Examples 7 to 22, Comparative Examples 1 to 7, and Comparative Examples 9 to 13 prepared in the above (1) was exposed using an exposure system (MULTILIGHT ML-251A/B, Ushio Inc.) with a built-in ultrahigh pressure mercury lamp, and an ethylenically unsaturated group absorption peak (810 cm$^{-1}$) was measured with an infrared spectrophotometer (FT/IR7000 manufactured by Japan Spectroscopic Co., Ltd.). Exposure was carried out at such an exposure that the reaction was brought to a steady state (500 mj/cm$^2$). The conversion of the ethylenically unsaturated group was measured from the level of a change in the ethylenically unsaturated group absorption peak (absorption peak intensity after exposure)/absorption peak intensity before exposure×100: %) at that time. The results are shown in Tables 10 to 13.

<Change in Viscosity>

The curable composition solutions prepared in the above (1) as such were provided, and, in order to evaluate the curability as a function of a change in viscosity, measurement was carried out with a rheometer with an ultrahigh pressure mercury lamp for light irradiation. In this case, while conducting light irradiation, the exposure at which the viscosity begins to increase was measured at 25° C. The results are shown in Tables 10 to 13.

<Adhesive Strength>

Evaluation samples of Examples 7 to 22, Comparative Examples 1 to 7, and Comparative Examples 9 to 13 prepared in the above (1) were exposed at an exposure of 3 j/cm$^2$ using an exposure system with a built-in ultrahigh pressure mercury lamp. The surface of the cured film for each sample was polished with sandpaper. Further, a holding tool in an adhesion tester (Elcometor manufactured by Elcometer Instrument Ltd) was cured with an epoxy adhesive (HC-1210 manufactured by Mitsui Chemicals Inc.), and the adhesive strength was measured with an adhesion tester. The results are shown in Tables 10 to 13.

<Transmittance>

Evaluation samples of Examples 7 to 22, Comparative Examples 1 to 7, and Comparative Examples 9 and 10 prepared in the above (1) were exposed at an exposure of 3 j/cm$^2$ using an exposure system with a built-in ultrahigh pressure mercury lamp. For each of the cured samples, the transmittance at 550 nm was measured with a spectrophotometer (UV3100, manufactured by Japan Spectroscopic Co., Ltd.). The results are shown in Tables 10 to 13.

<Heat Resistance>

Evaluation samples of Examples 7 to 22, Comparative Examples 1 to 7, and Comparative Examples 9 to 13 prepared in the above (1) were exposed at an exposure of 3 j/cm$^2$ using an exposure system with a built-in ultrahigh pressure mercury lamp. For each of the cured samples, the decomposition temperature was measured with a differential scanning calorimeter (EXSTAR6000, manufactured by Seiko Instrument Inc.) for comparison about the heat resistance among the samples. The results are shown in Tables 10 to 13.

<Refractive Index>

Each of the curable composition solutions prepared in the above (1) was coated onto a PET film to a film thickness of about 200 µm on a dry basis. The coating was dried at 50° C. for 30 min to prepare evaluation samples of Examples 7 to 14 and Comparative Examples 1 to 7. Each of the samples thus obtained was exposed at an exposure of 3 j/cm² using an exposure system with a built-in ultrahigh pressure mercury lamp. Each of the cured samples was peeled off as a film, and the refractive index of each of the cured films was measured with an Abbe's refractometer. The results are shown in Tables 10 and 12.

<X-Ray Analysis>

Evaluation samples of Example 7 and Comparative Example 8 were prepared, and each of the samples thus obtained was exposed at an exposure of 3 j/cm² using an exposure system with a built-in ultrahigh pressure mercury lamp. Each of the cured samples were measured with an X-ray analyzer (RU-200B, manufactured by Rigaku International Corporation). The results are shown in FIG. 1.

Production Example 1

Synthesis of urethane(meth)acrylate (UB-1)

Polycaprolactonediol (PLACCEL 212, molecular weight 1,250, manufactured by Daicel Chemical Industries, Ltd.) (625 g, 0.5 mol) as a polyester polyol and BEI (239 g, 1.0 mol), a compound listed in Table 14 were introduced into a reaction vessel equipped with a stirrer, a thermometer, and a condenser. p-Methoxyphenol and di-t-butyl-hydroxytoluene (each 1.0 g) were introduced thereinto. The mixture was heated to 60° C. with stirring. Thereafter, heating was stopped, and 0.2 g of dibutyltin dilaurate was added thereto. When the temperature within the reaction vessel began to drop, heating was again carried out. Stirring was continued at 80° C., and the reaction was terminated when the infrared absorption spectrum showed substantial disappearance of an absorption spectrum (2280 cm$^{-1}$) attributable to an isocyanate group. Thus, a urethane(meth)acrylate polymer (UB-1) as a viscose liquid was prepared. The urethane(meth)acrylate had an average molecular weight of 1,800.

Production Example 2

Synthesis of urethane(meth)acrylate (UB-2)

A urethane(meth)acrylate polymer (UB-2) was synthesized in the same manner as in Production Example 1, except that polycarbonatediol (PLACCEL CD 210PL (tradename), average molecular weight 1,000, manufactured by Daicel Chemical Industries, Ltd.) (500 g, 0.5 mol) was used instead of polycaprolactonediol. The urethane(meth)acrylate had a number average molecular weight of 1,500.

Production Example 3

Synthesis of urethane(meth)acrylate (UB-3)

A urethane(meth)acrylate polymer (UB-3) was synthesized in the same manner as in Production Example 1, except that polytetramethylene glycol (PTMG-850, molecular weight of 850, manufactured by Hodogaya Chemical Co., Ltd.) (425 g, 0.5 mol) was used instead of polycaprolactonediol. The urethane acrylate had a number average molecular weight of 1,350.

Production Example 4

Synthesis of urethane(meth)acrylate (UB-4)

Polytetramethylene glycol (PTMG-850, molecular weight of 850, manufactured by Hodogaya Chemical Co., Ltd.) (255 g, 0.3 mol), dimethylolpropionic acid (67 g, 0.5 mol), isophorone diisocyanate (133 g, 0.6 mol), BEI, a compound listed in Table 14 (95.6 g, 0.4 mol), 0.1 g of p-methoxyphenol and 0.1 g of di-t-butyl-hydroxytoluene were introduced thereinto. The mixture was heated to 60° C. with stirring. Thereafter, heating was stopped, and 0.1 g of dibutyltin dilaurate was added thereto. When the temperature within the reaction vessel began to drop, heating was again carried out. Stirring was continued at 80° C., and the reaction was terminated when the infrared absorption spectrum showed substantial disappearance of an absorption spectrum (2280 cm$^{-1}$) attributable to an isocyanate group. Thus, a urethane(meth)acrylate polymer (UB-4) as a viscose liquid was prepared. The urethane acrylate had a number average molecular weight of 23,000 and an acid value of 45 mgKOH/g.

Production Example 5

Synthesis of urethane(meth)acrylate (UB-5)

A urethane(meth)acrylate polymer (UB-5) was synthesized in the same manner as in Production Example 1, except that polycarbonatediol (PLACCEL CD 210PL (tradename), average molecular weight 1,000, manufactured by Daicel Chemical Industries, Ltd.) (500 g, 0.5 mol) and BMI, a compound listed in Table 14 (225 g, 1.0 mol) were used instead of polycaprolactonediol. The urethane acrylate had a number average molecular weight of 1,500.

Production Example 6

Synthesis of urethane(meth)acrylate (UB-6)

Methacrylic acid (12.0 g), 2-hydroxyethylacrylate (6.0 g), and propylene glycol monomethyl ether acetate (225.0 g) were charged into a four-necked flask equipped with a dropping funnel, a thermometer, a cooling pipe, and a stirrer, and the air in the four-necked flask was replaced by nitrogen for one hr. The flask was heated to 90° C. on an oil bath, and a mixed liquid composed of methacrylic acid (12.0 g), methyl methacrylate (14.0 g), butyl methacrylate (43.0 g), 2-hydroxyethylacrylate (6.0 g), propylene glycol monomethyl ether acetate (225.0 g), and azobisisobutyronitrile (3.2 g) was then added dropwise thereto over a period of one hr. After polymerization for 3 hr, a mixed liquid composed of azobisisobutyronitrile (1.0 g) and propylene glycol monomethyl ether acetate (15.0 g) was added thereto. The mixture was heated to 100° C., polymerization was allowed to proceed for 1.5 hr, and the reaction solution was then allowed to cool. BEI (20.3 g) listed in Table 14 was gradually added to the solution, and the mixture was stirred at 80° C. for 4 hr to synthesize a copolymer (UB-6). The copolymer thus obtained had an acid value of 90 mgKOH/g and a mass average molecular weight of 25,000 in terms of polystyrene as measured by GPC.

Comparative Production Example 1

Synthesis of urethane(meth)acrylate (UA-1)

A urethane(meth)acrylate polymer (UA-1) was prepared in the same manner as in Production Example 1, except that 2-acryloyloxyethyl isocyanate (142 g, 1.0 mol) was used instead of the compound BEI listed in Table 14 for the reaction. The urethane acrylate thus obtained had an average molecular weight of 1,600.

Comparative Production Example 2

Synthesis of urethane(meth)acrylate (UA-2)

A urethane(meth)acrylate polymer (UA-2) was prepared in the same manner as in Production Example 2, except that 2-acryloyloxyethyl isocyanate (142 g, 1.0 mol) was used instead of the compound BEI listed in Table 14 for the reaction. The urethane acrylate thus obtained had an average molecular weight of 1,300.

Example 23

UB-1 (30.0 g, solid content 7.0 g) produced in Production Example 1, propylene glycol monomethyl ether acetate (5.0 g), a dispersant (Flowlen DOPA-33, solid content 30%, manufactured by Kyoeisha Chemical Co., Ltd.) (3.5 g), and carbon black (Special Black 4, manufactured by Degussa) (7.0 g) were mixed together, and the mixture was then allowed to stand overnight. Next, this mixture was stirred for one hr and was passed through a three-roll mill (R III-1 RM-2, manufactured by Kodaira Seisakusho Co., Ltd.) four times. Cyclohexanone was added to the black mixture thus obtained for concentration adjustment to prepare a black colored composition having a solid content of 18.0%.

The colored composition prepared above and other ingredients were mixed together in a mixing ratio as described in Table 2 to prepare a black curable composition which was then filtered through a filter with a pore diameter of 0.8 μm (Kiriyama filter paper for GFP). The filtrate was evaluated for photosensitivity and resist properties (OD value (optical density), reflectance, and pencil hardness) by the following methods.

Evaluation of Photosensitivity

The curable composition was spin coated onto a glass substrate (size: 100×100 mm), and the coating was dried at room temperature for 30 min and was then prebaked at 70° C. for 20 min. The film thickness of the resist was previously measured with a film thickness meter (SURFCOM 130A, manufactured by TOKYO SEIMITSU), and the resist was photocured with an exposure system with an ultrahigh pressure mercury lamp incorporated therein (MULTILIGHT ML-251 A/B (tradename), manufactured by Ushio Inc.) with varied exposure. Further, the resist was developed with an alkali developing agent (a 0.1% aqueous potassium carbonate solution, Developer 9033, manufactured by Shipley Far East Ltd.) at 25° C. for a predetermined period of time. After alkali development, the coated glass substrate was washed with water and was dried by air spraying, and the film thickness of the remaining resist was measured. The exposure at which the value (remaining film sensitivity) calculated by the following equation:

Remaining film sensitivity %="(film thickness after alkali development)/(film thickness before alkali development)"×100 was not less than 95% was regarded as the photosensitivity of the curable composition. The results are shown in Table 16.

Evaluation of Resist Properties

The curable composition was spin coated onto a glass substrate (size: 100×100 mm), and the coating was dried at room temperature for 30 min and was then prebaked at 70° C. for 20 min. The coating was then photocured using an ultrahigh pressure mercury lamp at an exposure of twice the photosensitivity of the composition and was then post-baked at 200° C. for 30 min. The resist coated glass substrate thus obtained was used for the following evaluation.

OD value (Optical Density)

A calibration curve was prepared by measuring the transmittance at 550 nm with a standard plate having a known OD value. Next, the transmittance at 550 nm of the resist-coated glass substrate prepared in each of the Examples and Comparative Examples was measured to determine the OD value. The results are shown in Table 16.

Reflectance

For each of the resists, the reflectance at 550 nm was measured with a spectrophotometer (UV-3100 PC, manufactured by Shimadzu Seisakusho Ltd.), and the pencil hardness was measured according to JIS K 5400. The results are shown in Table 16.

Examples 24 to 28 and Comparative Examples 14 and 15

Evaluation was carried out in the same manner as in Example 23, except that the ingredients were used according to formulations shown in Table 15. The results are shown in Table 16.

Examples 29 to 34 and Comparative Examples 16 and 17

The ingredients were mixed together according to formulations (parts by mass) shown in Table 17 to prepare compositions. A bisphenol A-type epoxy resin EPICLON 860 (manufactured by Dainippon Ink and Chemicals, Inc.) was used as a heat-curable resin (C). 2,4,6-Trimethyl benzoyl phenyl phosphine oxide TPO (manufactured by BASF) and 4,4'-bis(diethylamino)benzophenone EAB-F (manufactured by Hodogaya Chemical Co., Ltd.) were used as a photopolymerization initiator (D). Melamine PC-1 (manufactured by Nissan Chemical Industries Ltd.) was used as a thermal polymerization catalyst (E).

(Preparation of Curable Composition Coating Film)

The viscosity of each of the curable compositions prepared according to the formulations shown in Table 4 was modified to 5,000 mPa·s by the addition of methyl cellosolve acetate, and each of the viscosity modified curable compositions was screen printed to a thickness of 30 Mm onto a printed board comprising a 35 μm-thick copper foil stacked onto one side of a 50 μm-thick polyimide film (UPISEL (registered trademark) N, manufactured by UBE Industries, Ltd. which had been washed with a 1% aqueous sulfuric acid solution, was washed with water, and was dried with an air stream), and the coating was dried at 70° C. to prepare a substrate.

(Exposure and Development)

A test piece of each of the laminates thus obtained was exposed at 500 mJ/cm$^2$ with an exposure system equipped with a metal halide lamp (HMW-680 GW, manufactured by Orc manufacturing Corporation) through a negative pattern having squares of 1 cm×1 cm in an area of 4 cm×6 cm. Next, the exposed laminates were developed by spraying 1 mass % aqueous sodium carbonate solution at 30° C. for 60 sec to remove unexposed areas. The developed laminates were then heat treated at 150° C. for 30 min. Thus, copper-clad laminates with a copper foil of 1 cm×1 cm square exposed thereon were prepared.

(Gold Plating Resistance)

Electroless gold plating was carried out using the copper-clad laminates prepared above by the following step. For the test pieces, a change in appearance was judged, and the state of peeling of the resist was judged by a peeling test using Cello-Tape®. The results are shown in Table 17.

◯ . . . Neither change in appearance nor resist peeling was observed at all.

Δ . . . Slight peeling of resist was observed although no change in appearance was observed.

X . . . Lifting of resist was observed, plating got in between resist and copper foil, and resist peeling was significant in peeling test.

(Step of Electroless Gold Plating)

Degreasing: The test piece was immersed in an acidic degreasing liquid (20 vol % aqueous solution of Metex L-5B, manufactured by MacDermid Japan) of 30° C. for 3 min.

Water washing: The test piece was immersed in running water for 3 min.

Soft etching: The test piece was immersed in a 14.3 wt % aqueous ammonium persulfate solution at room temperature for one min.

Water washing: The test piece was immersed in running water for 3 min.

Immersion in acid: The test piece was immersed in a 10 vol % aqueous sulfuric acid solution at room temperature for one min.

Water washing: The test piece was immersed in running water for 30 sec to one min.

Application of catalyst: The test piece was immersed in a catalyst liquid (10 vol % aqueous solution of Melplate Activator 350, manufactured by Meltex Inc.) of 30° C. for 7 min.

Water washing: The test piece was immersed in running water for 3 min.

Electroless nickel plating (gold plating substrate layer): The test piece was immersed in a nickel plating solution (85° C., pH=4.6) (20 vol % aqueous solution of Melplate Ni-865 M, manufactured by Meltex Inc.) for 20 min.

Immersion in acid: The test piece was immersed in a 10 vol % aqueous sulfuric acid solution at room temperature for one min.

Water washing: The test piece was immersed in running water for 30 sec to one min.

Electroless gold plating: The test piece was immersed in a gold plating solution (95° C., pH=6) (aqueous solution containing 15 vol % Aurolectroless UP, manufactured by Meltex Inc., and 3 vol % of aqueous gold potassium cyanide solution) for 10 min.

Water washing: The test piece was immersed in running water for 3 min.

Hot-water washing: The test piece was immersed in hot water of 60° C., thoroughly washed with water for 3 min, was then satisfactorily dehydrated and was dried to prepare an electroless gold plated test piece.

TABLE 1

| Reactive urethane compound | Reactive urethane compound, g | Polymerization initiator (Irgacure 184), g |
|---|---|---|
| Ex. 7 $C_8F_{17}$—structure with —OCOCH=CH$_2$ groups | 10 | 0.10 |
| Ex. 8 structure with —OCOCH=CH$_2$ groups | 10 | 0.10 |
| Ex. 9 structure with $C_6F_{12}$ and —OCOCH=CH$_2$ groups | 10 | 0.10 |

TABLE 2

| Reactive urethane compound | Reactive urethane compound, g | Polymerization initiator (Irgacure 184), g |
|---|---|---|
| Ex. 10 structure with —OCOCH=CH$_2$ groups | 10 | 0.10 |

TABLE 2-continued
| Reactive urethane compound | Reactive urethane compound, g | Polymerization initiator (Irgacure 184), g |
|---|---|---|
| Ex. 11 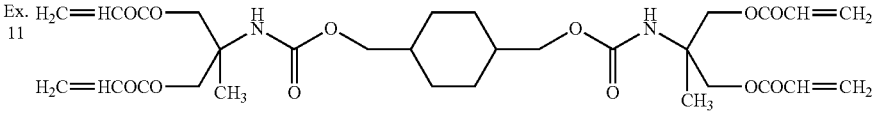 | 10 | 0.10 |
| Ex. 12 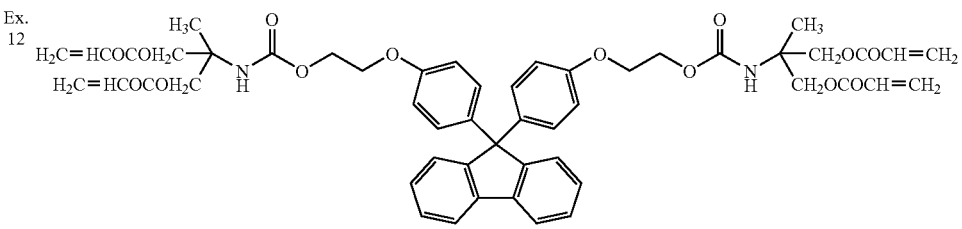 | 10 | 0.10 |
TABLE 3
| Reactive urethane compound | Reactive urethane compound, g | Polymerization initiator (Irgacure 184), g |
|---|---|---|
| Ex. 13 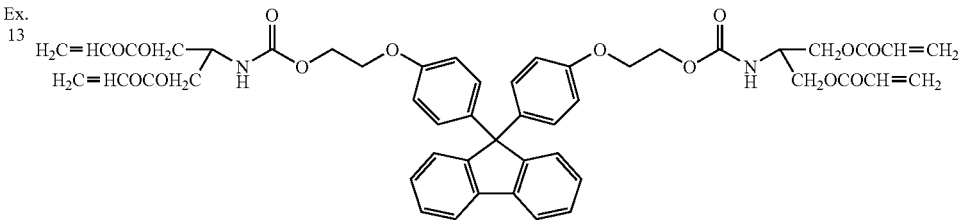 | 10 | 0.10 |
| Ex. 14 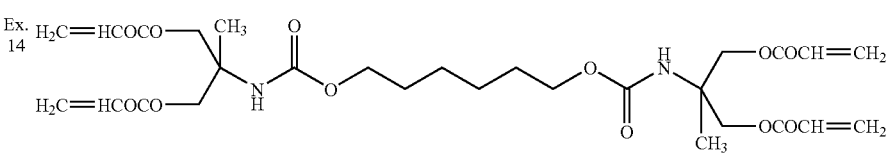 | 10 | 0.10 |
| Ex. 15 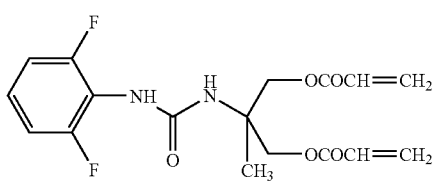 | 10 | 0.10 |

TABLE 4
| Reactive urethane compound | Reactive urethane compound, g | Polymerization initiator (Irgacure 184), g |
|---|---|---|
| Ex. 16 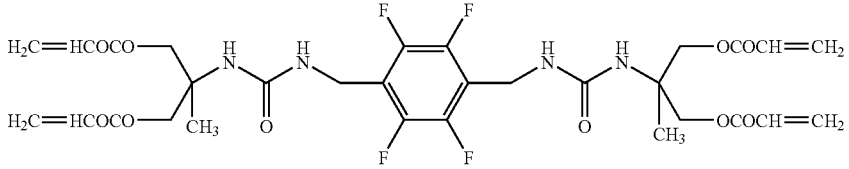 | 10 | 0.10 |
| Ex. 17 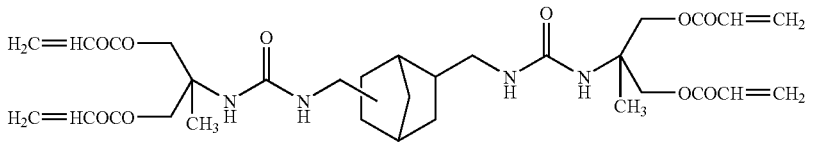 | 10 | 0.10 |
| Ex. 18 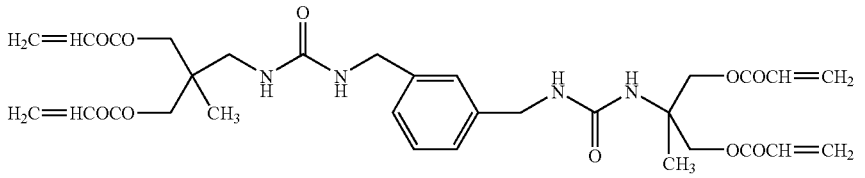 | 10 | 0.10 |
TABLE 5
| Reactive urethane compound | Reactive urethane compound, g | Polymerization initiator (Irgacure 184), g |
|---|---|---|
| Ex. 19 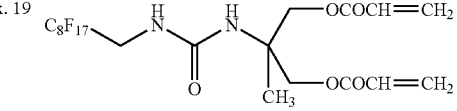 | 10 | 0.10 |
| Ex. 20 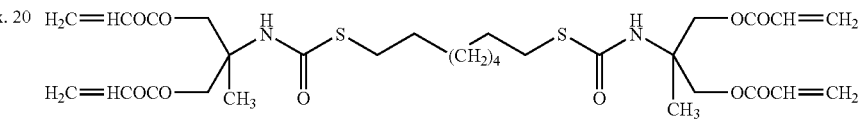 | 10 | 0.10 |
| Ex. 21 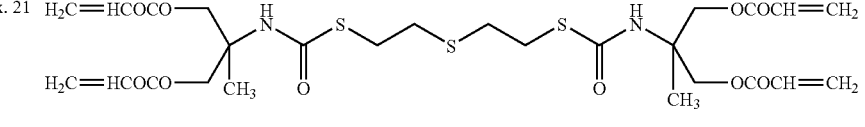 | 10 | 0.10 |
| Ex. 22 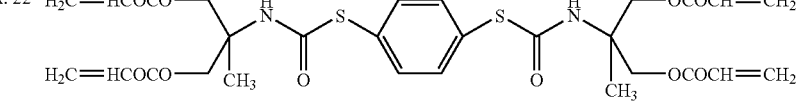 | 10 | 0.10 |
TABLE 6
| Reactive urethane compound | Reactive urethane compound, g | Polymerization initiator (Irgacure 184), g |
|---|---|---|
| Comp. Ex. 1 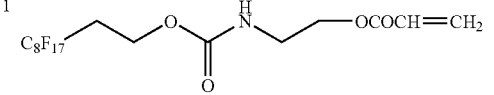 | 10 | 0.10 |

TABLE 6-continued

| Reactive urethane compound | | Reactive urethane compound, g | Polymerization initiator (Irgacure 184), g |
|---|---|---|---|
| Comp. Ex. 2 | H$_2$C=HCOCO—⟨⟩—N(H)—C(O)—O—⟨⟩—C$_6$F$_{12}$—⟨⟩—O—C(O)—N(H)—⟨⟩—OCOCH=CH$_2$ | 10 | 0.10 |
| Comp. Ex. 3 | H$_2$C=HCOCO—⟨⟩—N(H)—C(O)—O—⟨cyclohexyl⟩—O—C(O)—N(H)—⟨⟩—OCOCH=CH$_2$ | 10 | 0.10 |

TABLE 7

| Reactive urethane compound | | Reactive urethane compound, g | Polymerization initiator (Irgacure 184), g |
|---|---|---|---|
| Comp. Ex. 4 | H$_2$C=HCOCO—⟨⟩—N(H)—C(O)—O—⟨cyclohexyl⟩—O—C(O)—N(H)—⟨⟩—OCOCH=CH$_2$ | 10 | 0.10 |
| Comp. Ex. 5 | H$_2$C=HCOCO—⟨⟩—N(H)—C(O)—O—⟨⟩—O—⟨phenyl⟩—⟨9,9-fluorenyl⟩—⟨phenyl⟩—O—⟨⟩—O—C(O)—N(H)—⟨⟩—OCOCH=CH$_2$ | 10 | 0.10 |
| Comp. Ex. 6 | C$_8$H$_{17}$—⟨⟩—O—C(O)—N(H)—⟨⟩—OCOC(CH$_3$)=CH$_2$ | 10 | 0.10 |

TABLE 8

| Reactive urethane compound | | Reactive urethane compound, g | Polymerization initiator (Irgacure 184), g |
|---|---|---|---|
| Comp. Ex. 7 | H$_2$C=HCOCO—⟨⟩—N(H)—C(O)—O—(CH$_2$)$_5$—O—C(O)—N(H)—⟨⟩—OCOCH=CH$_2$ | 10 | 0.10 |
| Comp. Ex. 8 | H$_2$C=C(H)—C(O)—O—CH$_2$CH$_2$—(CF$_2$)$_8$—F | 10 | 0.10 |

TABLE 8-continued

| | Reactive urethane compound | Reactive urethane compound, g | Polymerization initiator (Irgacure 184), g |
|---|---|---|---|
| Comp. Ex. 9 | 2,6-difluorophenyl-NH-C(=O)-NH-CH₂CH₂-OCOCH=CH₂ | 10 | 0.10 |

TABLE 9

| | Reactive urethane compound | Reactive urethane compound, g | Polymerization initiator (Irgacure 184), g |
|---|---|---|---|
| Comp. Ex. 10 | H₂C=HCOCO-CH₂CH₂-NH-C(=O)-NH-CH₂-[norbornane]-CH₂-NH-C(=O)-NH-CH₂CH₂-OCOCH=CH₂ | 10 | 0.10 |
| Comp. Ex. 11 | C₈F₁₇-CH₂-NH-C(=O)-NH-CH₂CH₂-OCOCH=CH₂ | 10 | 0.10 |
| Comp. Ex. 12 | H₂C=HCOCO-CH₂CH₂-NH-C(=O)-S-CH₂CH₂CH₂-(CH₂)₄-CH₂CH₂-S-C(=O)-NH-CH₂CH₂-OCOCH=CH₂ | 10 | 0.10 |
| Comp. Ex. 13 | H₂C=HCOCO-CH₂CH₂-NH-C(=O)-S-CH₂CH₂-S-CH₂CH₂-S-C(=O)-NH-CH₂CH₂-OCOCH=CH₂ | 10 | 0.10 |

TABLE 10

| | Ex. 7 | Ex. 8 | Ex. 9 | Ex. 10 | Ex. 11 | Ex. 12 | Ex. 13 | Ex. 14 |
|---|---|---|---|---|---|---|---|---|
| Double bond conversion, % | 70 | 76 | 74 | 75 | 70 | 60 | 72 | 78 |
| Viscosity change, mj/cm² | 80 | 60 | 60 | 50 | 50 | 50 | 80 | 60 |
| Adhesive strength, N/mm² | 0.70 | 0.80 | 0.80 | 0.70 | 0.80 | 1.00 | 0.75 | 0.80 |
| Decomposition temp., °C | 355 | 350 | 350 | 355 | 350 | 360 | 355 | 360 |
| Transmittance, % | 98 | 97 | 98 | 97 | 98 | 99 | 99 | 98 |
| Refractive index | 1.418 | 1.49 | 1.45 | 1.52 | 1.5 | 1.58 | 1.52 | 1.49 |

TABLE 11

| | Ex. 15 | Ex. 16 | Ex. 17 | Ex. 18 | Ex. 19 | Ex. 20 | Ex. 21 | Ex. 22 |
|---|---|---|---|---|---|---|---|---|
| Double bond conversion, % | 90 | 78 | 75 | 80 | 82 | 90 | 91 | 90 |
| Viscosity change, mj/cm² | 110 | 90 | 80 | 100 | 80 | 50 | 60 | 50 |
| Adhesive strength, N/mm² | 0.80 | 1.00 | 0.95 | 0.80 | 0.80 | 1.10 | 1.20 | 1.10 |

TABLE 11-continued

|  | Ex. 15 | Ex. 16 | Ex. 17 | Ex. 18 | Ex. 19 | Ex. 20 | Ex. 21 | Ex. 22 |
|---|---|---|---|---|---|---|---|---|
| Decomposition temp., °C. | 350 | 360 | 350 | 350 | 340 | 350 | 360 | 360 |
| Transmittance, % | 97 | 97 | 98 | 96 | 98 | 99 | 99 | 98 |

① Double bond conversion: A change in infrared absorption peak intensity of double bond (after exposure/before exposure * 100)
② Viscosity change: Exposure necessary for an increase in viscosity of curable composition solution (33%) by exposure to light
③ Adhesive strength: Adhesive strength on glass substrate
④ Transmittance: Transmittance at 550 nm
⑤ Decomposition temp.: Decomposition temp. as measured with differential scanning calorimeter
⑥ Refractive index: Refractive index of cured film

TABLE 12

|  | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| Double bond conversion, % | 86 | 85 | 85 | 80 | 70 | 84 | 85 |
| Viscosity change, mj/cm$^2$ | 300 | 250 | 220 | 250 | 160 | 330 | 200 |
| Adhesive strength, N/mm$^2$ | 0.3 | 0.4 | 0.4 | 0.4 | 0.7 | 0.3 | 0.4 |
| Decomposition temp., °C. | 310 | 340 | 345 | 340 | 345 | 310 | 340 |
| Transmittance, % | 94 | 95 | 96 | 95 | 95 | 94 | 95 |
| Refractive index | 1.4 | 1.43 | 1.5 | 1.49 | 1.58 | 1.4 | 1.5 |

TABLE 13

|  | Comp. Ex. 9 | Comp. Ex. 10 | Comp. Ex. 11 | Comp. Ex. 12 | Comp. Ex. 13 |
|---|---|---|---|---|---|
| Double bond conversion, % | 86 | 85 | 88 | 94 | 93 |
| Viscosity change, mj/cm$^2$ | 300 | 220 | 160 | 140 | 150 |
| Adhesive strength, N/mm$^2$ | 0.45 | 0.50 | 0.5 | 0.7 | 0.8 |
| Decomposition temp. °C. | 320 | 340 | 320 | 330 | 330 |
| Transmittance, % | 93 | 95 | 95 | 96 | 95 |

TABLE 14

| BEI | BMI |
|---|---|

TABLE 15

|  |  | Ex. 23 | Ex. 24 | Ex. 25 | Ex. 26 | Ex. 27 | Ex. 28 | Comp. Ex. 14 | Comp. Ex. 15 |
|---|---|---|---|---|---|---|---|---|---|
| (A) | UB-1 | 28 | 0 | 0 | 0 | 0 | 0 | 0 | 0 |
|  | UB-2 | 0 | 28 | 0 | 0 | 0 | 0 | 0 | 0 |
|  | UB-3 | 0 | 0 | 28 | 0 | 0 | 0 | 0 | 0 |
|  | UB-4 | 0 | 0 | 0 | 28 | 0 | 0 | 0 | 0 |
|  | UB-5 | 0 | 0 | 0 | 0 | 28 | 0 | 0 | 0 |
|  | UB-6 | 0 | 0 | 0 | 0 | 0 | 28 | 0 | 0 |
|  | UA-1 | 0 | 0 | 0 | 0 | 0 | 0 | 28 | 0 |
|  | UA-2 | 0 | 0 | 0 | 0 | 0 | 0 | 0 | 28 |
| (B) | CB *1 | 42 | 42 | 42 | 42 | 42 | 42 | 42 | 42 |
| (D) | HABI *2 | 3 | 3 | 3 | 3 | 3 | 3 | 3 | 3 |
|  | EMK *3 | 0.5 | 0.5 | 0.5 | 0.5 | 0.5 | 0.5 | 0.5 | 0.5 |
| (F) | TMPT *4 | 3 | 3 | 3 | 3 | 3 | 3 | 3 | 3 |
| (G) | PMA *5 | 170 | 170 | 170 | 170 | 170 | 170 | 170 | 170 |
|  | CH *6 | 80 | 80 | 80 | 80 | 80 | 80 | 80 | 80 |

TABLE 15-continued

|  | Ex. 23 | Ex. 24 | Ex. 25 | Ex. 26 | Ex. 27 | Ex. 28 | Comp. Ex. 14 | Comp. Ex. 15 |
|---|---|---|---|---|---|---|---|---|
| (H) TPMB *7 | 2 | 2 | 2 | 2 | 2 | 2 | 2 | 2 |
| Dispersant | 4.2 | 4.2 | 4.2 | 4.2 | 4.2 | 4.2 | 4.2 | 4.2 |

*1 carbon black
*2 2,2'-bis(o-chlorophenyl)-4,4',5,5'-tetraphenyl-1,2'-bisimidazole
*3 4,4'-bis(diethylamino)benzophenone
*4 trimethylolpropane triacrylate
*5 propylene glycol monomethyl ether acetate
*6 cyclohexanone
*7 trimethylolpropane tris-3-mercapto-butyrate

TABLE 16

|  | Ex. 23 | Ex. 24 | Ex. 25 | Ex. 26 | Ex. 27 | Ex. 28 | Comp. Ex. 14 | Comp. Ex. 15 |
|---|---|---|---|---|---|---|---|---|
| Sensitivity | 40 | 50 | 70 | 70 | 50 | 40 | 120 | 100 |
| OD value | 3.1 | 3.0 | 3.0 | 3.0 | 3.2 | 3.2 | 3.0 | 3.0 |
| Reflectance | 1.8 | 1.7 | 2.0 | 1.8 | 2.0 | 1.9 | 2.3 | 2.4 |
| Pencil hardness | 4H | 4H | 4H | 4H | 4H | 4H | 3H | 3H |

TABLE 17

(parts by weight)

|  |  | Ex. 29 | Ex. 30 | Ex. 31 | Ex. 32 | Ex. 33 | Ex. 34 | Comp. Ex. 16 | Comp. Ex. 17 |
|---|---|---|---|---|---|---|---|---|---|
| (A) | UB-1 | 80 | 0 | 0 | 0 | 0 | 0 | 0 | 0 |
|  | UB-2 | 0 | 80 | 0 | 0 | 0 | 0 | 0 | 0 |
|  | UB-3 | 0 | 0 | 80 | 0 | 0 | 0 | 0 | 0 |
|  | UB-4 | 0 | 0 | 0 | 80 | 0 | 0 | 0 | 0 |
|  | UB-5 | 0 | 0 | 0 | 0 | 80 | 0 | 0 | 0 |
|  | UB-6 | 0 | 0 | 0 | 0 | 0 | 80 | 0 | 0 |
|  | UA-1 | 0 | 0 | 0 | 0 | 0 | 0 | 80 | 0 |
|  | UA-2 | 0 | 0 | 0 | 0 | 0 | 0 | 0 | 80 |
| (C) | EPICON 860 | 14 | 14 | 14 | 14 | 14 | 14 | 14 | 14 |
| (D) | TPO | 2 | 2 | 2 | 2 | 2 | 2 | 2 | 2 |
|  | EMK | 2 | 2 | 2 | 2 | 2 | 2 | 2 | 2 |
| (E) | PC-1 | 2 | 2 | 2 | 2 | 2 | 2 | 2 | 2 |
| Plating resistance |  | ○ | ○ | ○ | ○ | ○ | ○ | Δ | Δ |

As shown in Tables 1 to 9, Examples 7 to 22 have the same structure as Comparative Examples 1 to 7 and 9 to 13, except for the presence of an ethylenically unsaturated group-containing urethane bond, thiourethane bond, or urea bond. Further, in Tables 10 to 13, the polymerization initiator is incorporated in an amount of 0.1% by weight. Since, however, the number of ethylenically unsaturated groups in the compounds of Examples 7 to 22 is large and, thus, as compared with the Comparative Examples, the amount of the polymerization initiator based on one ethylenically unsaturated group is so small that this influence is considered to be negligible.

Accordingly, Examples 7 to 22 will be compared with Comparative Examples 1 to 7 and 9 to 13. For the conversion of the ethylenically unsaturated group, the Examples are lower than the Comparative Examples, whereas, for the exposure necessary for an increase in viscosity, an increase in viscosity was observed at a lower exposure for the Examples. The reason for this is believed to reside in that the presence of ethylenically unsaturated groups adjacent to each other in the reactive monomer used in the Examples causes an accelerated curing speed and increased viscosity which suppress radical mobility and inhibits the conversion of the ethylenically unsaturated group.

For the adhesive strength, Examples 7 to 22 had higher adhesive strength than Comparative Examples 1 to 7 and 9 to 13. Further, for the deposition temperature as measured with a differential scanning calorimeter, due to different structures of the compounds of the Examples and Comparative Examples, the Examples had somewhat higher values. As with the above case, this is also considered attributable to the effect of the adjacent ethylenically unsaturated group in the reactive monomer.

In the X-ray analysis, as a result of a comparison of the compound prepared in Example 7 with the compound prepared in Comparative Example 8, it was found that, for the compound prepared in Comparative Example 8, a crystalline region was observed for the cured sample, whereas, for the compound prepared in Example 7, a crystalline region was not observed, indicating that, for Example 7, curing proceeds in an amorphous manner.

For the transmittance, Examples 7 to 22 were higher than Comparative Examples 1 to 7 and 9 to 13. The reason for this is believed to reside in that, as is apparent from the results of X-ray analysis of Example 7 and Comparative Example 8, the crystallization is suppressed in Examples 7 to 22.

It is apparent that the refractive index depends upon the structure of the fluorourethane compound used in Examples 1 to 14 and Comparative Example 1 to 7 and further depends upon the fluorine content.

As is apparent from the above Examples, the reactive monomer obtained by reacting the isocyanate compound containing two adjacent ethylenically unsaturated groups in its molecule with a compound containing a hydroxyl, mercapto, or amino group is excellent in curability, adhesive strength to the substrate, heat resistance, and transparency and can be used as the reactive monomer useful in the curable composition.

Further, as a result of a comparison of Examples 23 to 28 with Comparative Examples 14 and 15, it was found that the incorporation of the reactive (meth)acrylate polymer produced from the ethylenically unsaturated group-containing isocyanate compound according to the present invention can increase the sensitivity and pencil hardness and can lower the reflectance. Furthermore, a comparison of Examples 29 to 34 with Comparative Examples 16 and 17 shows that the incorporation of the reactive (meth)acrylate can improve chemical resistance.

The invention claimed is:

1. An ethylenically unsaturated group-containing isocyanate compound represented by formula (I)

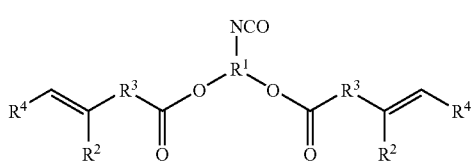

(I)

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; and $R^4$ represents a hydrogen atom, a straight-chain or branched-chain alkyl group having 1 to 6 carbon atoms, or an aryl group.

2. The ethylenically unsaturated group-containing isocyanate compound according to claim 1, characterized in that $R^1$ in formula (I) is a straight-chain or branched-chain saturated aliphatic group having 1 to 5 carbon atoms.

3. The ethylenically unsaturated group-containing isocyanate compound according to claim 1, characterized in that $R^3$ in formula (I) is a straight-chain or branched-chain alkylene group having 0 to 3 carbon atoms.

4. The ethylenically unsaturated group-containing isocyanate compound according to claim 1, characterized in that $R^4$ in formula (I) is a hydrogen atom or a methyl or aryl group.

5. The ethylenically unsaturated group-containing isocyanate compound according to claim 1, characterized by being represented by formula (II)

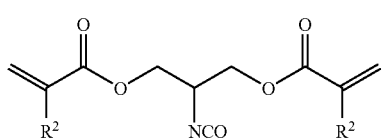

(II)

wherein $R^2$ represents a hydrogen atom or a methyl group.

6. The ethylenically unsaturated group-containing isocyanate compound according to claim 1, characterized by being represented by formula (III)

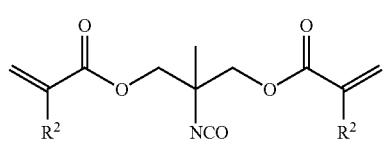

(III)

wherein $R^2$ represents a hydrogen atom or a methyl group.

7. The ethylenically unsaturated group-containing isocyanate compound according to claim 1, characterized by being represented by formula (IV)

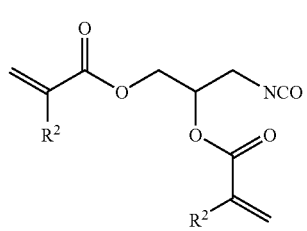

(IV)

wherein $R^2$ represents a hydrogen atom or a methyl group.

8. A process for producing an ethylenically unsaturated group-containing isocyanate compound characterized by comprising the steps of:

preparing a dihydroxyamine mineral acid salt compound represented by formula (VI)

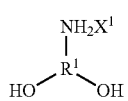

(VI)

wherein $R^1$ is as defined below, and $X^1$ represents a mineral acid, from a dihydroxyamine compound represented by formula (V)

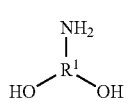

(V)

wherein $R^1$ represents a straight-chain or branched-chain saturated aliphatic group having 1 to 10 carbon atoms, and a mineral acid;

preparing an ester compound represented by formula (VIII)

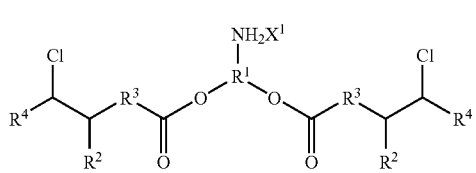

(VIII)

wherein $R^1$ and $X^1$ are as defined above and $R^2$ to $R^4$ are as defined below, from the dihydroxyamine mineral acid salt compound and a compound represented by formula (VII)

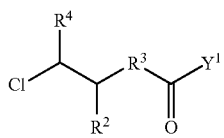

(VII)

wherein $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms;

preparing an isocyanate compound represented by formula (X)

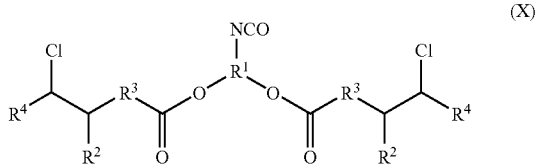

(X)

wherein $R^1$ to $R^4$ are as defined above, from the ester compound and a compound represented by general formula (IX)

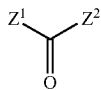

(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles; and dehydrochlorinating the isocyanate compound in the presence of a basic nitrogen compound to give an ethylenically unsaturated group-containing isocyanate compound represented by formula (I)

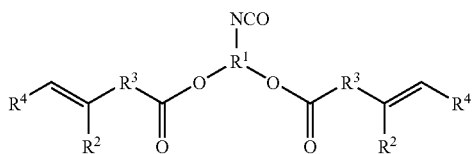

(I)

wherein $R^1$ to $R^4$ are as defined above.

9. The process for producing the ethylenically unsaturated group-containing isocyanate compound according to claim 8, characterized in that the mineral acid reacted with the dihydroxyamine compound represented by formula (V) is sulfuric acid, nitric acid, hydrochloric acid, carbonic acid, or phosphoric acid.

10. The process for producing an ethylenically unsaturated group-containing isocyanate compound according to claim 8, characterized in that the reaction in each of the steps is carried out in a solvent.

11. The process for producing an ethylenically unsaturated group-containing isocyanate compound according to claim 8, characterized in that the reaction in the step of preparing the dihydroxyamine mineral acid salt compound represented by formula (VI) from the dihydroxyamine compound represented by formula (V) and the mineral acid is carried out in a solvent selected from water, alcohols, esters, ethers, aromatic hydrocarbons, aliphatic hydrocarbons, and halogenated hydrocarbons.

12. The process for producing an ethylenically unsaturated group-containing isocyanate compound according to claim 8, characterized in that the reaction in the step of preparing the ester compound represented by formula (VIII), the reaction in the step of preparing the isocyanate compound represented by formula (X), and the reaction in the step of preparing the ethylenically unsaturated group-containing isocyanate compound represented by formula (I) are carried out in a solvent selected from esters, ethers, aromatic hydrocarbons, aliphatic hydrocarbons, and halogenated hydrocarbons.

13. The process for producing an ethylenically unsaturated group-containing isocyanate compound according to claim 8, characterized in that, after the dihydroxyamine compound represented by formula (V) is reacted with the mineral acid in the solvent to give the dihydroxyamine mineral acid salt compound represented by formula (VI), the reaction solvent is removed by evaporation and the next step of carrying out the reaction for preparing the ester compound represented by formula (VIII) is carried out.

14. The process for producing an ethylenically unsaturated group-containing isocyanate compound according to claim 8, characterized in that the reaction in the step of dehydrochlorinating the isocyanate compound represented by formula (X) in the presence of a basic nitrogen compound to give the ethyleneically unsaturated group-containing isocyanate compound represented by formula (I) is carried out at a temperature of 0° C. to 150° C.

15. The process for producing an ethylenically unsaturated group-containing isocyanate compound according to claim 8, characterized in that basic nitrogen compound used in the step of dehydrochlorinating the isocyanate compound represented by formula (X) in the presence of a basic nitrogen compound to give the ethyleneically unsaturated group-containing isocyanate compound represented by formula (I) is triethylamine.

16. A process for producing an ethylenically unsaturated group-containing isocyanate compound characterized by comprising the steps of:

preparing a dihydroxyamine mineral acid salt compound represented by formula (VI)

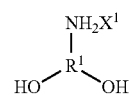

(VI)

wherein $R^1$ is as defined below, and $X^1$ represents a mineral acid, from a dihydroxyamine compound represented by formula (V)

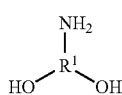

wherein $R^1$ represents a straight-chain or branched-chain saturated aliphatic group having 1 to 10 carbon atoms, and a mineral acid;

preparing an ester compound represented by formula (XII)

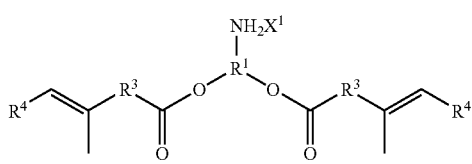

(XII)

wherein $R^1$ and $X^1$ are as defined above and $R^3$ and $R^4$ are as defined below, from the dihydroxyamine mineral acid salt compound and a compound represented by formula (XI)

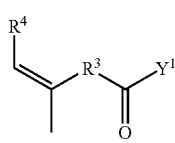

(XI)

wherein $R^3$ represents a straight-chain or branched-chain alkylene group having 0 to 5 carbon atoms; $R^4$ represents a hydrogen atom, a straight-chain or branched-chain alkyl group having 1 to 6 carbon atoms or an aryl group; and $Y^1$ represents a hydroxyl group, a chlorine atom, or $R^6O$— wherein $R^6$ represents an alkyl group having 1 to 6 carbon atoms; and preparing an ethylenically unsaturated group-containing isocyanate compound represented by formula (XIII)

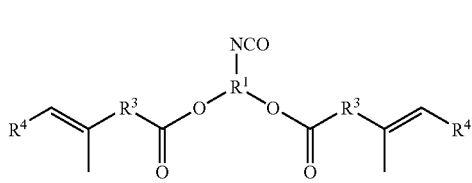

(XIII)

wherein $R^1$, $R^3$, and $R^4$ are as defined above, from the ester compound and a compound represented by general formula (IX)

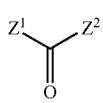

(IX)

wherein $Z^1$ and $Z^2$ each independently represent a chlorine atom; a bromine atom; $R^7O$— wherein $R^7$ represents a straight-chain or branched-chain alkyl group having 1 to 6 carbon atoms, a straight-chain or branched-chain alkenyl group having 1 to 6 carbon atoms, or an optionally substituted aryl group; a residue of imidazoles; or a residue of pyrazoles.

17. The process for producing the ethylenically unsaturated group-containing isocyanate compound according to claim 16, characterized in that the mineral acid reacted with the dihydroxyamine compound represented by formula (V) is sulfuric acid, nitric acid, hydrochloric acid, carbonic acid, or phosphoric acid.

18. The process for producing an ethylenically unsaturated group-containing isocyanate compound according to claim 16, characterized in that the reaction in each of the steps is carried out in a solvent.

19. The process for producing an ethylenically unsaturated group-containing isocyanate compound according to claim 16, characterized in that the reaction in the step of preparing the dihydroxyamine mineral acid salt compound represented by formula (VI) from the dihydroxyamine compound represented by formula (V) and the mineral acid is carried out in a solvent selected from water, alcohols, esters, ethers, aromatic hydrocarbons, aliphatic hydrocarbons, and halogenated hydrocarbons.

20. The process for producing an ethylenically unsaturated group-containing isocyanate compound according to claim 16, characterized in that the reaction in the step of preparing the ester compound represented by formula (XII) and the reaction in the step of preparing the ethylenically unsaturated group-containing isocyanate compound represented by formula (XIII) are carried out in a solvent selected from esters, ethers, aromatic hydrocarbons, aliphatic hydrocarbons, and halogenated hydrocarbons.

21. The process for producing an ethylenically unsaturated group-containing isocyanate compound according to claim 16, characterized in that, after the dihydroxyamine compound represented by formula (V) is reacted with the mineral acid in the solvent to give the dihydroxyamine mineral acid salt compound represented by formula (VI), the reaction solvent is removed by evaporation and the next step of carrying out the reaction for preparing the ester compound represented by formula (XII) is carried out.

22. A reactive monomer represented by formula (Ia)

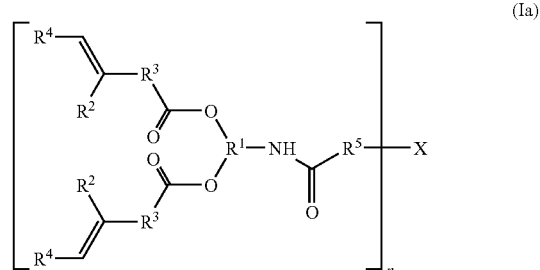

(Ia)

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms, or an aryl group; $R^5$ represents an ether, thioether, or NH group; X represents an aliphatic, aromatic, or heterocyclic group; and n is an integer of 1 to 4.

23. The reactive monomer according to claim 22, characterized by being represented by formula (IIa)

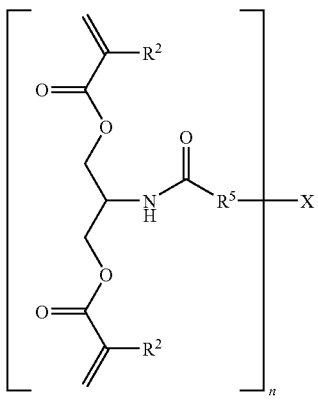

wherein $R^2$, $R^5$, and X are as defined above.

24. The reactive monomer according to claim 22, characterized by being represented by formula (IIIa)

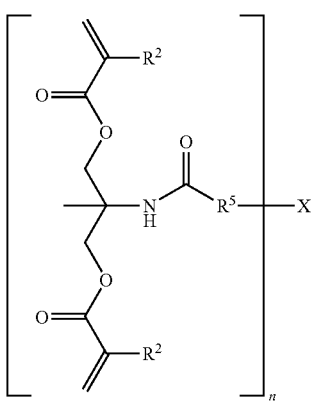

wherein $R^2$, $R^5$, and X are as defined above.

25. The reactive monomer according to claim 22, characterized by being represented by formula (IVa)

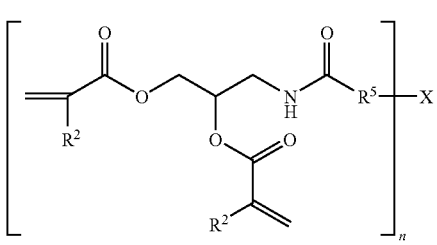

wherein $R^2$, $R^5$, and X are as defined above.

26. The reactive monomer according to claim 22, characterized in that $R^5$ in formula (Ia) is an ether group, X represents a fluorine-containing group, and n=1.

27. The fluorine-containing reactive monomer according to claim 26, characterized in that X in formula (Ia) is a group represented by $-(CH_2)_m(CF_2)_lF$ wherein m is an integer of 0 to 2 and l is an integer of 0 to 8, provided that m and l are not simultaneously 0.

28. The reactive monomer according to claim 22, characterized in that $R^5$ in formula (Ia) is an ether group, X represents a fluorine-containing group, and n=2.

29. The reactive monomer according to claim 22, characterized in that $R^5$ in formula (Ia) is an ether group, X represents a group having a fluorene skeleton, and n=2.

30. The reactive monomer according to claim 29, characterized in that X in formula (Ia) is a group represented by formula (XVI)

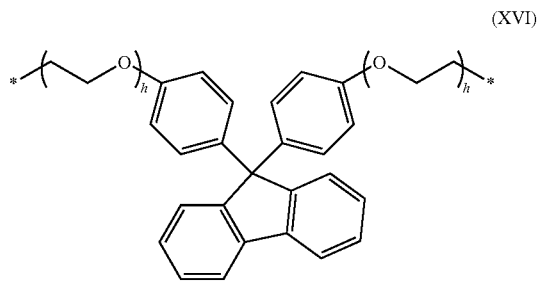

wherein h is an integer of 1 to 4.

31. The reactive monomer according to claim 22, characterized in that $R^5$ in formula (Ia) is group NH, X represents a fluorine-containing group, and n=1.

32. The reactive monomer according to claim 31, characterized in that X in formula (Ia) represents a group represented by $F(CF_2)_8CH_2-$, or $X-R^5$ represents a residue of 2,6-difluoroaniline.

33. The reactive monomer according to claim 22, characterized in that $R^5$ in formula (Ia) is group NH, X represents an alkyl, xylylene, or norbornane group, and n=2.

34. The reactive monomer according to claim 33, characterized in that $X-R^5$ in formula (Ia) represents a residue of m-xylylenediamine or a residue of 2,3,5,6-tetrafluoro-1,4-xylylenediamine, or X is represented by formula (XVII)

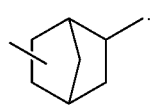

35. The reactive monomer according to claim 22, characterized in that $R^5$ in formula (Ia) represents a thioether group, X represents a straight-chain or branched-chain saturated aliphatic group, or a phenyl group.

36. A process for producing a reactive (meth)acrylate polymer, characterized in that an ethylenically unsaturated group-containing isocyanate compound represented by formula (I)

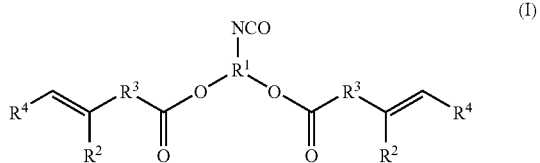

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; and $R^4$ represents a hydrogen atom, a straight-chain or branched-chain alkyl group having 1 to 6 carbon atoms, or an aryl group, is reacted with a polymer compound comprising repeating units to which an active hydrogen-containing functional group is attached.

37. The process for producing a reactive (meth)acrylate polymer according to claim 36, characterized in that said polymer compound is a polyhydroxy compound comprising repeating units.

38. The process for producing a reactive (meth)acrylate polymer according to claim 36, characterized in that said ethylenically unsaturated group-containing isocyanate compound is represented by formula (II)

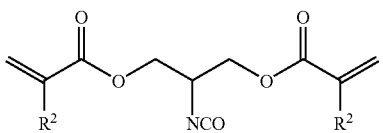

(II)

wherein $R^2$ represents a hydrogen atom or a methyl group.

39. The process for producing a reactive (meth)acrylate polymer according to claim 36, characterized in that said ethylenically unsaturated group-containing isocyanate compound is represented by formula (III)

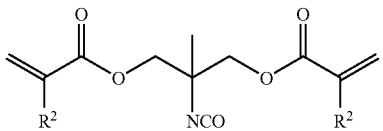

(III)

wherein $R^2$ represents a hydrogen atom or a methyl group.

40. The process for producing a reactive (meth)acrylate polymer according to claim 37, characterized in that said repeating unit-containing polyhydroxy compound is a polyester polyol compound, a polycarbonate polyol compound, a polyether polyol compound, a polyurethane polyol compound, a homo- or copolymer of hydroxyalkyl(meth)acrylate, or an epoxy(meth)acrylate compound.

41. The process for producing a reactive (meth)acrylate polymer according to claim 37, characterized in that said repeating unit-containing polyhydroxy compound contains a carboxyl group.

42. A reactive (meth)acrylate polymer produced in that an ethylenically unsaturated group-containing isocyanate compound represented by formula (I)

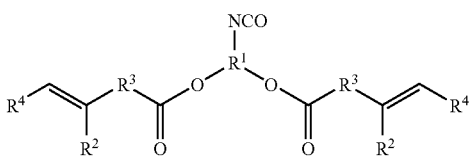

(I)

wherein $R^1$ represents a straight-chain or branched-chain saturated aliphatic group having 1 to 10 carbon atoms; $R^2$ represents a hydrogen atom or a methyl group; $R^3$ represents a straight-chain or branched-chain alkylene group having 0 to 5 carbon atoms; $R^4$ represents a hydrogen atom, a straight-chain or branched-chain alkyl group having 1 to 6 carbon atoms, or an aryl group, is reacted with a polymer compound comprising repeating units to which an active hydrogen-containing functional group is attached.

43. The reactive (meth)acrylate polymer according to claim 42, characterized in that said polymer compound is a repeating unit-containing polyhydroxy compound.

44. The reactive (meth)acrylate polymer according to claim 42, characterized in that said ethylenically unsaturated group-containing isocyanate compound is represented by formula (II)

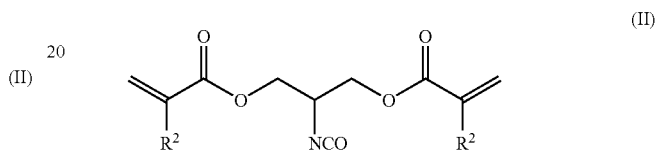

(II)

wherein $R^2$ represents a hydrogen atom or a methyl group.

45. The reactive (meth)acrylate polymer according to claim 42, characterized in that said ethylenically unsaturated group-containing isocyanate compound is represented by formula (III)

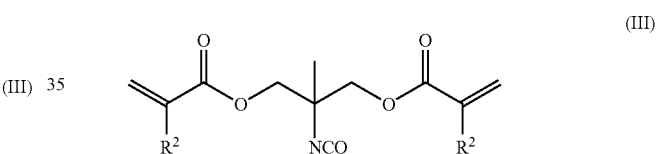

(III)

wherein $R^2$ represents a hydrogen atom or a methyl group.

46. The reactive (meth)acrylate polymer according to claim 43, characterized in that said repeating unit-containing polyhydroxy compound is a polyester polyol compound, a polycarbonate polyol compound, a polyether polyol compound, a polyurethane polyol compound, a homo- or copolymer of a hydroxyalkyl(meth)acrylate, or an epoxy(meth)acrylate compound.

47. The reactive (meth)acrylate polymer according to claim 43, characterized in that said repeating unit-containing polyhydroxy compound contains a carboxyl group.

48. A curable composition characterized by comprising the reactive monomer according to claim 22 and a polymerization initiator.

49. A cured product produced by curing the curable composition according to claim 48.

50. A curable composition characterized by comprising a reactive (meth)acrylate polymer (A) according to claim 43 and a pigment (B).

51. The curable composition according to claim 50, characterized by further comprising a photopolymerization initiator (D).

52. The curable composition according to claim 51, characterized by further comprising an ethylenically unsaturated monomer (F).

53. The curable composition according to claim 52, characterized by comprising 10 to 40% by mass of the reactive (meth)acrylate polymer (A), 25 to 60% by mass of the pigment (B), 2 to 25% by mass of the photopolymerization initiator (D), 5 to 20% by mass of the ethylenically unsaturated monomer (F), and an organic solvent (G).

54. The curable composition according to claim 52, characterized by comprising 10 to 40% by mass of the reactive (meth)acrylate polymer (A), 25 to 60% by mass of the pigment (B), 2 to 20% by mass of the photopolymerization initiator (D), 5 to 20% by mass of the ethylenically unsaturated monomer (F), the organic solvent (G), and 2 to 20% by mass of a polyfunctional thiol (H).

55. The curable composition according to claim 52, characterized in that said curable composition is used for color filter formation.

56. The curable composition according to claim 55, characterized in that the pigment (B) is carbon black.

57. A curable composition characterized by comprising the reactive (meth)acrylate polymer (A) according to claim 43, a heat-curable polymer (C), a photopolymerization initiator (D), and a thermal polymerization catalyst (E).

58. The curable composition according to claim 57, characterized in that said curable composition is used as a solder resist.

59. An insulating protective film having been formed using the curable composition according to claim 58.

60. A printed wiring board comprising the insulating protective film according to claim 59.

* * * * *